US008445240B2

(12) United States Patent
Scharf et al.

(10) Patent No.: US 8,445,240 B2
(45) Date of Patent: May 21, 2013

(54) TERMITE ENZYMES AND USES THEREOF FOR IN VITRO CONVERSION OF LIGNIN-CONTAINING MATERIALS TO FERMENTABLE PRODUCTS

(75) Inventors: Michael E. Scharf, Battle Ground, IN (US); Drion G. Boucias, Gainesville, FL (US); Aurelien Tartar, Cooper City, FL (US); Monique R. Coy, Gainville, FL (US); Xuguo Zhou, Lexington, KY (US); Tamer Ibrahim Zaki Salem, East Lansing, MI (US); Sanjay B. Jadhao, Gainesville, FL (US); Marsha M. Wheeler, Urbana, IL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 31 days.

(21) Appl. No.: 13/263,107

(22) PCT Filed: Mar. 31, 2010

(86) PCT No.: PCT/US2010/029342
§ 371 (c)(1),
(2), (4) Date: Oct. 6, 2011

(87) PCT Pub. No.: WO2010/117843
PCT Pub. Date: Oct. 14, 2010

(65) Prior Publication Data
US 2012/0064580 A1 Mar. 15, 2012

Related U.S. Application Data

(60) Provisional application No. 61/168,275, filed on Apr. 10, 2009.

(51) Int. Cl.
C12P 19/02 (2006.01)
C12N 9/00 (2006.01)
C12P 7/06 (2006.01)
C07H 21/02 (2006.01)

(52) U.S. Cl.
USPC ........... 435/105; 435/183; 435/161; 536/23.1

(58) Field of Classification Search
None
See application file for complete search history.

(56) References Cited

U.S. PATENT DOCUMENTS
2008/0118954 A1 5/2008 Sticklen

FOREIGN PATENT DOCUMENTS
WO WO 2010/005551 * 1/2010

OTHER PUBLICATIONS

International Search Report and Written Opinion dated Mar. 14, 2011.

NCBI Accession No. AAU20853, Aug. 8, 2005.
Nakashima, et al., Distribution and Properties of Endo-β-1, 4-glucanase from a Lower Termite, *Coptotermes formosanus* (Shiraki), Biosco. Biotechnol. Biochem, (2000) vol. 64, pp. 1500-1506.
Tokuda, et al., "Hidden Cellulases in Termites: Revision of an Old Hypothesis," Bio. Lett. (2007) vol. 3, pp. 336-339.
Belles, X., et al., 2005, "The Mevalonate Pathway and the Synthesis of Juvenile Hormone in Insects," Annu. Rev. Entomol. 50, pp. 181-199.
Breznak, et al., 1995, "Role of Microorganisms in the Digestion of Lignocellulose by Termites," Annu. Rev. Entomol., 39, pp. 453-487.
Brune, et al., 1995, "The Termite Gut Microflora as an Oxygen Sink: Microelectrode Determination of Oxygen and pH Gradients in Guts of Lower and Higher Termites," Appl. Env. Microbiol. 61, pp. 2681-2687.
Cornette, et al., 2008, Juvenile Hormone Titers and Caste Differentiation in the Damp-Wood *Termite Hodotermopsis sjostedti* (Isoptera, Termopsidae), J. Insect. Physiol. 54, pp. 922-930.
Davis, et al., 1995, "Characterization of General Esterases in Workers of the Eastern Subterranean Termite (Isoptera: Rhinotermitidae), " J. Econ. Entomol. 88, pp. 574-578.
Elliott, et al., 2007, "Juvenile Hormone Synthesis as Related to Egg Development in Neotenic Reproductives of the Termite *Reticulitermes flavipes*, with Observations on Urates in the Fat Body." Gen. Comp. Endocrinol. 152, pp. 102-110.
Fisher, et al., 2007, "Diversity of Gut Bacteria of *Reticulitermes flavipes* as Examined by 16S rRNA Gene Sequencing and Amplified rDNA Restriction Analysis," Curr. Microbiol. 55, pp. 254-259.
Keeling, et al., 2006, "Effect of Juvenile Hormone on Gene Expression in the Pheromone-Producing Midgut of the Pine Engraver Beetle, *Ips pini*," Insect. Mol. Biol. 15. pp. 207-216.
Lange, J.P. 2007, "Lignocellulose Conversion: an Introduction to Chemistry, Process and Economics," Biofuels Bioprod. Bioref. 1, pp. 39-48.

(Continued)

*Primary Examiner* — Suzanne M Noakes
(74) *Attorney, Agent, or Firm* — Thomas Horstemeyer, LLP

(57) ABSTRACT

The disclosure provides isolated nucleic acid molecules derived from the gut of the termite *R flavipes*, recombinant nucleic acid molecules comprising a vector and an isolated heterologous nucleic acid molecule operably inserted therein, whereby, when transformed into an appropriate host cell system, the heterologous nucleic acid sequence is expressed as a polypeptide having an activity similar to that when expressed in the gut of the termite *R. flavipes*. The recombinant nucleic acid molecules can comprise more than one heterologous nucleic acid molecule such that more than one polypeptide may be expressed by the host system. The expressed polypeptides may be substantially purified, or used in a substantially unpurified form, to be admixed with a lignocellulose source to be converted to a fermentable product such as a sugar or a mixture of sugars. One aspect of the present disclosure, therefore, encompasses methods of converting a lignified plant material to a fermentable product, the method comprising obtaining a series of isolated polypeptides of a termite, wherein the series of polypeptides cooperate to convert a plant lignocellulose to a fermentable product; and incubating the series of polypeptides with a source of lignified plant material, under conditions allowing the polypeptides to cooperatively produce a fermentable product from the lignified plant material.

19 Claims, 14 Drawing Sheets

OTHER PUBLICATIONS

Ohkuma, M., 2003, "Termite Symbiotic Systems: Efficient Bio-Recycling of Lignocellulose," Appl. Microbiol. Biotechnol. 61, pp. 1-9.

Ruvolo-Takasusuki, et al., 2000, "Characterization of *Nasutitermes globiceps* (Isoptera: Termitidae) Esterases," Biochem. Genet. 38, pp. 367-375.

Saha, B.C., 2003, "Hemicellulose Bioconversion," J. Indust. Microbiol. Biotechnol. 30, pp. 279-291.

Scharf, et al., 1998, "Changes of Insecticide Resistance Levels and Detoxification Enzymes Following Insecticide Selection in the German Cockroach, *Blattella germanica* (L.)," Pestic. Biochem. Physiol. 59, pp. 67-79.

Scharf, et al., 2005, "Effects of Juvenile Hormone III on *Reticulitermes flavipes*: Changes in Hemolymph Protein Composition and Gene Expression," Insect. Biochem. Molec. Bio. 35, pp. 207-215.

\* cited by examiner

```
            10         20         30         40         50         60         70         80
RfEst-1    MAETVTVTVAQGELRGKKMTAKTGTTYFSFQGIPYCQPPVGPLREKAPQPPDSWKGIRDALNEGSVAPQIDDFVADAYLG
RfEst-2    --------------------------------------------------------------------------------
RfEst-3    --------------------------------------------------------------------------------
RfEst-4    --------------------------------------------------------------------------------

90        100        110        120        130        140        150        160
RfEst-1    EEDCLYLNVYTPKVPARSGDDLKAVMWIHGGGFYMGSGNTQINGPDYLLAADVVVVTLNYRLGALGFLSTEDPETSSNN
RfEst-2    --------------------------------------------------------------------------------
RfEst-3    --------------------------------------------------------------------------------
RfEst-4    --------------------------------------------------------------------------------

170        180        190        200        210        220        230        240
RfEst-1    GLKDQVMALRWVQQNIKQFGGDPGNVTIFGVSAGGASVHYHMLSPMSEGLFCRAIAQSGCALNPWAFHAASTARRRAFRF
RfEst-2    --------------------------------------------------------------------------------
RfEst-3    --------------------------------------------------------------------------------
RfEst-4    --------------------------------------------------------------------------------

250        260        270        280        290        300        310        320
RfEst-1    GEVLGCKTDDSKELAEFLSTVPAQQLVEVVSKAMTEEELDLGTVFFRPTVEAENRQEELFLPADPIDLITEGKFHKVPFL
RfEst-2    --------------------------------------------------------------------------------
RfEst-3    --------------------------------------------------------------------------------
RfEst-4    --------------------------------------------------------------------------------

330        340        350        360        370        380        390        400
RfEst-1    TGINSSEGLLCVREVMAKPAVLKKYDSDFELLVPTNLGVEKNTPKSKEVAQKIKSFYFGDKPVSQETLFLYVDLSSDMWF
RfEst-2    -----------------MDARFEDVAPVASAYDT-SPRKNEISRLIRKFYFGDRHIDNDTTTSVVNMLTDGWF
RfEst-3    -------------------------------------------------------------------MQHN-
RfEst-4    -------------------------------------------------------------------MAGDRHF
```

*Fig. 1A*

```
              410         420         430         440         450         460         470         480
RfEst-1  VTDVHRTAKLQAARSSAPLFFYQFSFDGELGFM--KRIIGACRFPGVCHADELGYILIFSPHLDVELDGTP-EEKVRSQLV
RfEst-2  LQGADPAVSLHALRGPAPVFYHFTYRGSVSFI---TLFGNATESHGVSHGDDLIYLFPSESISPGTKLTAKDERVVDIMT
RfEst-3  ---IQKSVELHLQSGHDTVYLYNLGYRGKYSLLPKARYGNTRYDLGVAHVDELEFILSSAFTADRWEPGHPDLETVEDLV
RfEst-4  VVEMERAARIQAAVNSAPVTVYQFGYRGKHSLS--EEISGTNIDFGAAHADDAAFVLQIHYHNT--EETQQDKDMSKVLV
                                                     ↑           ↑
              490         500         510         520         530         540         550         560
RfEst-1  RMWTNFAKTGNPSLS---DVK-----CESMTES--NPSYLDIGTE--FTMQQHLMKDRMAFWDDLRQFVKI
RfEst-2  TVWTNFARTGNPNLSPDNAVQ------WRPVSSSH-DKEYVQIDSEG-LTPKKGLLEERANFWNSLPLKSSHSGSATSEL
RfEst-3  TLWTNFATHGNPTPEAETPTPQGVWPTAGANKDAITTYYVFDHS--PPPAEPI-YGVRPLRISVVPDKFKDRMDLWDSLPL
RfEst-4  DIWSSFSRNGNPNPDAPTFT-----WEPVTPNGAELAYLYIANSSHFEMRSSLDLGHREFWDSLPINEPQINVNVRNIRQS
         ↑ ↑↑↑
         565
RfEst-3  KENQ
RfEst-4  TREEL
```

Fig. 1B

TERMITE ENZYMES AND USES THEREOF FOR IN VITRO CONVERSION OF LIGNIN-CONTAINING MATERIALS TO FERMENTABLE PRODUCTS

CROSS REFERENCE TO RELATED APPLICATION

This application is the 35 U.S.C. §371 national stage of PCT application which claims priority to "TERMITE ENZYMES AND USES THEREOF FOR IN VITRO CONVERSION OF LIGNIN-CONTAINING MATERIALS TO FERMENTABLE PRODUCTS," having serial number PCT/US2010/029342, filed on Mar. 31, 2010. This application also claims priority to and benefit of U.S. Provisional Application No. 61/168,275 filed on Apr. 10, 2009, which is incorporated by reference in its entirety.

STATEMENT REGARDING FEDERALLY SPONSORED RESEARCH OR DEVELOPMENT

This invention was made with government support under Grant No. DE-FG36-02G012026 awarded by the Consortium for Plant Biotechnology Research/Department of Energy of the United States government DE-FG36-02G012026 awarded by the Consortium for Plant Biotechnology Research/Department of Energy of the United States government; CSREES-NRI 2007-35607-17777 awarded by the Department of Agriculture of the United States government; DE-FG02-08ER85063 awarded by the Department of Energy of the United States government; and 2009-05245 awarded by the Department of Agriculture of the United States government. The government has certain rights in the invention.

TECHNICAL FIELD

The present disclosure is generally related to enzymes, and to recombinant nucleic acid molecules encoding and/or expressing said enzymes, of the gut of the termite *Reticulitermes flavipes*. The disclosure further relates to a system combining said enzymes for substantially converting a plant lignocellulose to a fermentable sugar-based product.

BACKGROUND

Termites are social insects that subsist on sugars and other micronutrients obtained from nutritionally poor lignocellulose diets (Ohkuma M., (2006) *Appl. Microbiol. Biotechnol.* 61: 1-9; Scharf & Tartar (2008) *Biofuels Bioprod. Birefin.* 2: 540-552). Lignocellulose is a natural complex of the three biopolymers cellulose, hemicellulose and lignin. Cellulose is composed of long β-1,4-linked polymers of glucose that are held together in bundles by hemicellulose (Ljungdahl & Erickson (1985) *Adv. Micro. Ecol.* 8: 237-299; Lange J. P. (2007) *Biofuels Bioprod. Bioref.* 1: 39-48). Hemicellulose is composed of shorter β-1,4-linked polymers of mixed sugars such as mannose, xylose, galactose, rhamnose, arabinose, glucuronic acid, mannuronic acid, and galacturonic acid (Saha B. C., (2003) *J. Indust. Microbiol. Biotechnol.* 30: 279-291). Lignin is a 3-dimensional polymer of phenolic compounds that are linked to each other and to hemicellulose by ester bonds. Lignin is composed of three "mono-lignol" monomers (p-coumaryl alcohol, coniferyl alcohol, and sinapyl alcohol), which are combined in different ratios depending on the plant species. Another important characteristic of hemicellulose is its esterification with monomers and dimers of phenolic acid esters, which are identical to the mono-lignols that compose lignin (Saha B. C., (2003) *J. Indust. Microbiol. Biotechnol.* 30: 279-291; Crepin et al., (2004) *Appl. Microbiol. Biotechnol.* 63, 647-652; Benoit et al., (2008) *Biotechnol. Letters* 30, 387-396).

Termites digest lignocellulose with the assistance of endogenous and symbiont-produced digestive enzymes and co-factors (Breznak and Brune (1995) *Appl. Env. Microbiol.* 61: 2681-2687; Watanabe et al., (1998) Nature 394: 330-331; Ohkuma et al., (2006) *Appl. Microbiol. Biotechnol.* 61: 1-9; Scharf & Tartar (2008) *Biofuels Bioprod. Birefin.* 2: 540-552). Termite gut endosymbionts include a diversity of microorganisms that include protozoa, bacteria, spirochetes, fungi, and yeast, among others (Breznak and Brune (1995) *Appl. Env. Microbiol.* 61: 2681-2687; Warnecke et al., (2007) Nature 450, 560-565). The order Isoptera is divided into the higher and lower termites based mostly on symbiont composition. Lower termites, including *Reticulitermes flavipes*, possess cellulolytic protozoa in addition to a host of hydrogenic, methanogenic, and nitrogen fixing bacteria and spirochetes. Higher termites lack protozoa altogether, but instead possess cellulolytic bacteria. The roles of endosymbiotic fungi in higher and lower termites are not well defined; however, some higher termites cultivate fungus gardens in their nests that assist in lignocellulose digestion by producing cellulases, hemicellulases and lignases (Taprab et al., (2005) *Appl. Env. Microbiol.* 71: 7696-7704; Okhuma M., (2006) Appl Microbiol Biotechnol 61, 1-9).

Esterases are hydrolytic enzymes that cleave ester bonds in a diversity of biomolecules (Oakeshott et al. (2005) in Gilbert, L. I., Iatrou, K., Gill, S. S. (eds.) Comprehensive molecular insect science, Vol. 5, Elsevier-Pergamon, New York, pp. 309-382). Some insect esterases have very well defined biological functions, such as those involved in xenobiotic, lipid, acetylcholine, and juvenile hormone metabolism. However, many other insect esterases have largely undefined functions, yet are extremely efficient at metabolizing model substrates such as naphthyl and p-nitrophenyl esters. This latter category of esterases is referred to as the "general esterases". Because of the highly esterified structure of lignin, it is possible that some general esterases may also contribute to lignin depolymerization in wood feeding insects such as termites.

Lignocellulose is a sustainable global resource with a great deal of relevance to renewable energy production. It is a naturally occurring complex of plant derived materials that includes the β-1,4-linked sugar polymers cellulose and hemicellulose, and the phenolic polymer lignin. In plants, lignocellulose provides key structural support for cell walls. Because it is plant-derived, lignocellulose is the most abundant and widespread bioenergy feedstock available on Earth. However, a major limitation in plant biomass utilization as a renewable energy source is the inefficiency of industrial lignocellulose depolymerization. This inefficiency increases energy inputs, reduces product yields, drives production costs higher, encourages political skepticism, and ultimately limits acceptance of cellulose-based renewable bioenergy. With respect to the problem of lignocellulose recalcitrance, it is germane that a number of invertebrate animals, and to some extent, their symbiotic gut fauna, have evolved specialized enzymes that cooperate in lignocellulose processing. In particular, endogenous lignocellulases encoded in marine and terrestrial invertebrate genomes can often confer high degrees of digestion capabilities to these organisms. When endogenous insect lignocellulases work synergistically with symbiont-derived enzymes, this can confer extremely high efficiency in lignocellulose processing. Termites (order Isoptera) are one of the most well recognized examples of an organism that subsists on lignocellulose; and thus, lignocellulase enzymes from termites and their gut symbionts have many potential bioenergy applications that warrant consideration.

SUMMARY

Briefly described, embodiments of this disclosure, among others, encompass the use of polypeptides derived from the termite *R. flavipes* alone, or in combination, in systems for the in vitro reduction of biomaterial containing a lignin component to a product that may be fermented to provide a source of a biofuel. The present disclosure provides data that support that a wood (lignocellulose) source can provide glucose moieties when treated in vitro with a combination of termite-derived enzyme such as, but not limited to, an endoglucanase, an exoglucanase, a laccase, and a β-glucosidase. It is well known that free glucose may be fermented to such as ethanol for use as a bio-fuel.

Accordingly, the present disclosure provides isolated nucleic acid molecules derived from the gut of the termite *R. flavipes*, recombinant nucleic acid molecules comprising a vector and an isolated heterologous nucleic acid molecule operably inserted therein, whereby, when transformed into an appropriate host cell system, the heterologous nucleic acid sequence is expressed as a polypeptide having an activity similar to that when expressed in the gut of the termite *R. flavipes*. It is within the scope of the disclosure for the recombinant nucleic acid molecules to comprise more than one heterologous nucleic acid molecule such that more than one polypeptide may be expressed by the host system. The expressed polypeptides may be substantially purified, or used in a substantially unpurified form, to be admixed with a lignocellulose source to be converted to a fermentable product such as a sugar or a mixture of sugars.

One aspect of the present disclosure, therefore, encompasses methods of converting a lignified plant material to a fermentable product, the method comprising the steps of: (a) obtaining a series of isolated polypeptides of a termite, wherein the series of polypeptides cooperate to convert a plant lignocellulose to a fermentable product; and (b) incubating the series of polypeptides with a source of lignified plant material, under conditions allowing the polypeptides to cooperatively produce a fermentable product from the lignified plant material.

In embodiments of this aspect of the disclosure, the isolated polypeptides can be derived from the termite *Reticulitermes flavipes*.

In the various embodiments of this aspect of the disclosure, the isolated polypeptides of the series of isolated polypeptides can be recombinant polypeptides, where each polypeptide is expressed from an expression vector of a recombinant expression system, and wherein the recombinant expression system is selected from a eukaryotic cell-based system and a prokaryotic cell-based system.

In one embodiment of the disclosure, the expression vector is a baculovirus expression vector and the recombinant expression system is a eukaryotic cell-based system.

In the various embodiments of the disclosure, the series of isolated polypeptides comprise an endoglucanase having an amino acid sequence having about 75% sequence identity with the amino acid sequence SEQ ID NO.: 2.

In one embodiment of the disclosure, the endoglucanase can comprise the amino acid sequence SEQ ID NO.: 2.

In the various embodiments of the disclosure, the series of isolated polypeptides comprises an exoglucanase having an amino acid sequence having about 75% sequence identity with the amino acid sequence SEQ ID NO.: 4.

In one embodiment of the disclosure, the series of isolated polypeptides comprises an exoglucanase having the amino acid sequence SEQ ID NO.: 4.

In the various embodiments of the disclosure, the series of isolated polypeptides comprises a laccase having an amino acid sequence having about 75% sequence identity with an amino acid sequence selected from the group consisting of: SEQ ID NOs.: 8, 10, 12, 15, 17, 19, 21, and 23.

In one embodiment of the disclosure, the series of isolated polypeptides comprises a laccase having the amino acid sequence selected from the group consisting of: SEQ ID NOs.: 8, 10, 12, 15, 17, 19, 21, and 23.

In the various embodiments of the disclosure, the series of isolated polypeptides comprises an esterase having an amino acid sequence having about 75% sequence identity with the amino acid sequence selected from the group consisting of: SEQ ID NOs.: 27, 29, 31, and 33.

In one embodiment of the disclosure, the series of isolated polypeptides comprises an esterase having the amino acid sequence selected from the group consisting of: SEQ ID NOs.: 27, 29, 31, and 33.

In one embodiment of the disclosure, the series of isolated polypeptides comprises a glucosidase having the amino acid sequence SEQ ID NO.: 6.

Another aspect of the present disclosure encompasses systems for producing a fermentable product from a lignified plant material, wherein the system may comprise at least two isolated polypeptides selected from the group consisting of: an endoglucanase, an exoglucanase, a laccase, an esterase, and a glucosidase of the termite *Reticulitermes flavipes* and wherein two or more isolated polypeptides can cooperate to convert a constituent of the lignified plant material to a fermentable product or a precursor thereof.

In embodiments of this aspect of the disclosure, the nucleotide sequence encoding the endoglucanase may hybridize under high stringency conditions to a nucleotide sequence according to SEQ ID NO.: 1, the nucleotide sequence encoding the exoglucanase may hybridize under high stringency conditions to a nucleotide sequence according to SEQ ID NO.: 3, the nucleic acid molecule encoding the laccase may hybridize under high stringency conditions to a nucleotide sequence selected from the group consisting of: SEQ ID NOS.: 7, 9, 11, 13, 14, 16, 18, 20, and 22, the nucleic acid molecule encoding the esterase may hybridize under high stringency conditions to a nucleotide sequence selected from the group consisting of: SEQ ID NOS.: 26, 28, 30, and 32, and the nucleotide sequence encoding the glucosidase may hybridize under high stringency conditions to SEQ ID NO.: 5.

In embodiments of this aspect of the disclosure, each of the isolated nucleic acid molecules thereof may be operably inserted into an expression vector.

Still another aspect of the disclosure encompasses a recombinant cell comprising an isolated nucleic acid molecule hybridizing under high stringency conditions to a nucleotide sequence encoding a polypeptide selected from the group consisting of: an endoglucanase, an exoglucanase, a laccase, an esterase, and a glucosidase of the termite *Reticulitermes flavipes*, wherein the nucleotide sequence encoding the endoglucanase is according to SEQ ID NO.: 1, the nucleotide sequence encoding the exoglucanase is according to SEQ ID NOS.: 3, the nucleic acid molecule encoding the laccase is selected from the group consisting of: SEQ ID NOS.: 7, 9, 11, 13, 14, 16, 18, 20, and 22, the nucleic acid molecule encoding the esterase is selected from the group consisting of: SEQ ID NOS.: 26, 28, 30, and 32, and the nucleotide sequence encoding the glucosidase is according to SEQ ID NO.: 5.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1A and 1B illustrate a Clustal W alignment of translated termite gut esterases RfEst 1, 2, 3 and 4 (SEQ ID NOs.: 27, 29, 31, and 33). Boxes denote conserved esterase catalytic site and substrate recognition motifs. Arrows indicate amino acid residues that are 100% conserved across all proteins.

(FIG. 8, Left) pH dependence of CMC activity at 30° C. in sodium acetate buffer, pH 3.0-6.5. (Right) pH dependence of CMC activity at 30° C. in sodium phosphate buffer, pH 7.0-10.5.

(FIG. 9A) CMC activity after pre-incubation at 25° C. for 0 through 5 days with buffer alone (sodium phosphate, pH 7), buffer+5 mM EDTA, or buffer+30 mM calcium chloride. (FIG. 9B and FIG. 9C) CMC activity after pre-incubation at 60° C. or 70° C., respectively, for 0 through 60 min with buffer alone, buffer+5 mM EDTA, or buffer+30 mM calcium chloride. All assays were conducted at 25° C. Results shown are the average of three independent replicates is a graph of data showing that the presence of calcium improves Cell-1 temperature stability, while the calcium chelator EDTA reduces temperature stability.

(FIG. 13A) EDTA, (FIG. 13B) sodium cyanide, (FIG. 13C) thioglycolic acid, (FIG. 13D) sodium azide. Bars with different letters are significantly different at $p<0.05$.

Figure 2:
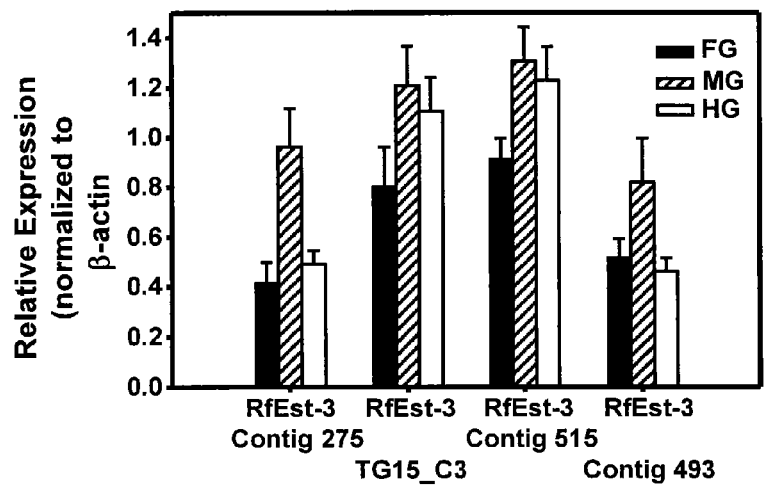
FIG. 2 illustrates a graph showing the average±std. error band intensities determined from densitometric analyses of five replicate gels from workers of two termite colonies (30 cycles of amplification). Bars for individual genes with the same letter are not significantly different by LSD t-tests ($p<0.05$). Abbreviations: FG (foregut/salivary gland), MG (midgut), HG (hindgut), bp (nucleotide base pairs).

The details of some exemplary embodiments of the methods and systems of the present disclosure are set forth in the description below. Other features, objects, and advantages of the disclosure will be apparent to one of skill in the art upon examination of the following description, drawings, examples and embodiments. It is intended that all such additional systems, methods, features, and advantages be included within this description, be within the scope of the present disclosure.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

In describing the disclosed subject matter, the following terminology will be used in accordance with the definitions set forth below.

The term "termite gut" as used herein refers to the gut of R. flavipes workers. The gut of R. flavipes workers is composed of three main regions: foregut, midgut, and hindgut. The foregut region includes the esophagus, crop, and attached salivary gland. The salivary glands secrete endogenous (termite-derived) digestive factors and enzymes into the digestive tract. The midgut is a slender, tubular region that secretes a peritrophic matrix around food materials and, presumably, is a location where some lignocellulose degradation occurs. The Malpighian tubules connect at the junction of the midgut and hindgut and participate in waste excretion. The hindgut includes a fermentation chamber that is generally anaerobic in its core, but it does possess a micro-oxic zone around its periphery. The hindgut houses gut symbionts, and it is the location where most lignocellulose degradation, as well as fermentation and nutrient assimilation, are thought to occur.

The fermentation chamber of the hindgut is a source of microbial diversity. Microorganisms from various taxa present in the termite gut include bacteria/spirochetes and protozoans. In lower termites such as R. flavipes, protozoan symbionts are considered to be primarily involved in cellulose/hemicellulose degradation, while bacteria are considered important to nitrogen economy and simple sugar fermentation. Spirochetes, which are difficult to culture, are found in the hindguts of all termites. Spirochetes play roles in acetogenesis and nitrogen fixation, and they and other endomicrobionts also occur as cytoplasmic symbionts of hindgut protozoa.

The term "lignocellulose" as used herein refers to a natural complex of the three biopolymers: cellulose, hemicellulose and lignin. Cellulose is composed of rigid, high-molecular-weight, β-1,4-linked polymers of glucose that are held together in bundles by hemicellulose. Hemicellulose is composed of shorter β-1,4-linked polymers of mixed sugars. Mannose is usually the dominant sugar present in hemicelluloses of softwoods fed upon by termites, with lesser amounts of xylose, galactose, rhamnose, arabinose, glucuronic acid, mannuronic acid and galacturonic acid.

The term "lignin" as used herein refers to a 3-dimensional polymer of phenolic compounds that are linked to each other and to hemicellulose by ester bonds. Lignin is composed of the three mono-lignol monomers p-coumaryl alcohol, coniferyl alcohol, and sinapyl alcohol combined in different ratios depending on the plant species. Another noteworthy aspect of hemicellulose is its high degree of esterification with monomers and dimers of phenolic acid esters, which are analogous to the mono-lignols noted above. Phenolic acid esters are derived mostly from the mono-lignols p-coumaryl and coniferyl alcohol (i.e., coumaric acid and ferulic acid). The three individual lignocellulose components, cellulose, hemicellulose and lignin, compose approximately 40%, 25%, and 20%, respectively, of lignocellulose (Lange 2007).

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present disclosure include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, insect viruses (baculovirus), and the like, vectors derived from bacteriophage nucleic acid, and synthetic oligonucleotides like chemically synthesized DNA or RNA. The term "nucleic acid" further includes modified or derivatized nucleotides and nucleosides such as, but not limited to, halogenated nucleotides such as, but not only, 5-bromouracil, and derivatized nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

The term "enriched" as used herein in reference to nucleic acid is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased. The other DNA may, for example, be derived from a yeast or bacterial genome, or a cloning vector, such as a plasmid or a viral vector. The term "significant" as used herein is used to indicate that the level of increase is useful to the person making such an increase.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide, or a portion or fragment thereof.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "transcription regulatory sequences" and "gene expression control regions" as used herein refer to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter" as used herein refers to the DNA sequence that determines the site of transcription initiation from an RNA polymerase. A "promoter-proximal element" may be a regulatory sequence within about 200 base pairs of the transcription start site.

The term "coding region" as used herein refers to a continuous linear arrangement of nucleotides that may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, chemiluminescent moieties, biotin, and the like that are well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of an gene expression control region or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g., low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° Celsius. Formulae to calculate appropriate hybridization and wash conditions to achieve hybridization permitting 30% or less mismatch between two nucleic acid molecules are disclosed, for example, in Meinkoth et al., 1984, Anal. Biochem. 138: 267-284; the contents of which is incorporated herein by reference in its entirety. Protocols for hybridization techniques are well known to those of skill in the art and standard molecular biology manuals may be consulted to select a suitable hybridization protocol without undue experimentation. See, for example, Sambrook et al., 1989, "Molecular Cloning: A Laboratory Manual," 2nd ed., Cold Spring Harbor Press: the contents of which is incorporated herein by reference in its entirety.

Typically, stringent conditions will be those in which the salt concentration is less than about 1.5 M Na ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° Celsius for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius and a wash in 1-2×SSC at 50 to 55° Celsius. Exemplary moderate stringency conditions include hybridization in 40 to 45% formamide, 1 M NaCl, 1% SDS at 37° Celsius and a wash in 0.5-1×SSC at 55 to 60° Celsius. Exemplary high stringency conditions include hybridization in 50% formamide, 1 M NaCl, 1% SDS at 37° C., and a wash in 0.1×SSC at 60 to 65° Celsius.

The terms "unique nucleic acid region" and "unique protein (polypeptide) region" as used herein refer to sequences present in a nucleic acid or protein (polypeptide) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The term "sense strand" as used herein refers to a single stranded DNA molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

The term "nucleic acid vector" as used herein refers to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises a gene expression control region operably linked to a nucleotide sequence coding at least one polypeptide. As used herein, the term "regulatory sequences" includes promoters, enhancers, and other elements that may control gene expression. Standard molecular biology textbooks (for example, Sambrook et al., eds., 1989, "Molecular Cloning: A Laboratory Manual," 2nd ed., Cold Spring Harbor Press) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell including, but not limited to, an insect host cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. Other preferred transfecting agents include, but are not limited to, lipofectin, lipofectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, poly(ethylenimine) (PEI) and the like.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term intragenomic defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell. The nucleic acid sequences include, but are not limited to, nucleic acid vectors, gene expression regulatory elements, origins of replication, suitable gene sequences that when expressed confer antibiotic resistance, protein-encoding sequences, and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

The techniques used to isolate and characterize the nucleic acids and proteins of the present disclosure are well known to those of skill in the art and standard molecular biology and biochemical manuals may be consulted to select suitable protocols without undue experimentation (see, for example, Sambrook et al., "Molecular Cloning: A Laboratory Manual," 2nd ed., 1989, Cold Spring Harbor Press; the contents of which is incorporated herein by reference in its entirety).

The term "glycosylation site" as used herein refers to a location on a polypeptide that has a glycosylation chain attached thereto. The "site" may be an amino acid side-chain, or a plurality of side-chains (either contiguous in the amino acid sequence or in cooperative vicinity to one another to define a specific site associated with at least one glycosylation chain).

Many cell surface and secretory proteins produced by eukaryotic cells are modified with one or more oligosaccharide groups. This modification, referred to as "glycosylation" can dramatically affect the physical properties of proteins and can also be important in protein stability, secretion, and subcellular localization. Proper glycosylation can be essential for biological activity. In fact, some genes from eukaryotic organisms, when expressed in bacteria (e.g., E. coli) which lack cellular processes for glycosylating proteins, yield proteins that are recovered with little or no activity by virtue of their lack of glycosylation.

Glycosylation occurs at specific locations along the polypeptide backbone and is usually of two types: O-linked oligosaccharides are attached to serine or threonine residues while N-linked oligosaccharides are attached to asparagine residues when they are part of the sequence Asn-X-Ser/Thr, where X can be any amino acid except proline. The structures of N-linked and O-linked oligosaccharides and the sugar residues found in each type are different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein.

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

"Denaturation" of a template molecule refers to the unfolding or other alteration of the structure of a template so as to make the template accessible to duplication. In the case of DNA, "denaturation" refers to the separation of the two complementary strands of the double helix, thereby creating two complementary, single stranded template molecules. "Denaturation" can be accomplished in any of a variety of ways, including by heat or by treatment of the DNA with a base or other denaturant.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR), which is defined and described in later sections below. The PCR process of Mullis is described in U.S. Pat. Nos. 4,683,195 and 4,683,202. PCR involves the use of a thermostable DNA polymerase, known sequences as primers, and heating cycles, which separate the replicating deoxyribonucleic acid (DNA), strands and exponentially amplify a gene of interest.

Any type of PCR, such as quantitative PCR, RT-PCR, hot start PCR, LAPCR, multiplex PCR, touchdown PCR, etc., may be used. Advantageously, real-time PCR is used. In general, the PCR amplification process involves an enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

"DNA" refers to the polymeric form of deoxyribonucleotides (adenine, guanine, thymine, or cytosine) in either single stranded form, or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

By the terms "enzymatically amplify" or "amplify" is meant, for the purposes of the specification or embodiments, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme Qβ replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, a patient's genetic characteristics, as defined by the nucleotide sequence of its genome, are known as its "genotype," while the patient's physical traits are described as its "phenotype."

The term "polymerase chain reaction" or "PCR" refers to a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and in distinct temporal steps. In many embodiments, however, the hybridization and primer extension processes can be performed concurrently. The nucleotide sample to be analyzed may be PCR amplification products provided using the rapid cycling techniques described in U.S. Pat. Nos. 6,569,672; 6,569,627; 6,562,298; 6,556,940; 6,569,672; 6,569,627; 6,562,298; 6,556,940; 6,489,112; 6,482,615; 6,472,156; 6,413,766; 6,387,621; 6,300,124; 6,270,723; 6,245,514; 6,232,079; 6,228,634; 6,218,193; 6,210,882; 6,197,520; 6,174,670; 6,132,996; 6,126,899; 6,124,138; 6,074,868; 6,036,923; 5,985,651; 5,958,763; 5,942,432; 5,935,522; 5,897,842; 5,882,918; 5,840,573; 5,795,784; 5,795,547; 5,785,926; 5,783,439; 5,736,106; 5,720,923; 5,720,406; 5,675,700; 5,616,301; 5,576,218 and 5,455,175, the disclosures of which are incorporated by reference in their entireties. Other methods of amplification include, without limitation, NASBR, SDA, 3SR, TSA and rolling circle replication. It is understood that, in any method for producing a polynucleotide containing given modified nucleotides, one or several polymerases or amplification methods may be used. The selection of optimal polymerization conditions depends on the application.

A "polymerase" is an enzyme that catalyzes the sequential addition of monomeric units to a polymeric chain, or links two or more monomeric units to initiate a polymeric chain. In advantageous embodiments of this disclosure, the "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers.

A "primer" is an oligonucleotide, the sequence of at least a portion of which is complementary to a segment of a template DNA which to be amplified or replicated. Typically primers are used in performing the polymerase chain reaction (PCR). A primer hybridizes with (or "anneals" to) the template DNA and is used by the polymerase enzyme as the starting point for the replication/amplification process. By "complementary" is meant that the nucleotide sequence of a primer is such that the primer can form a stable hydrogen bond complex with the template; i.e., the primer can hybridize or anneal to the template by virtue of the formation of base-pairs over a length of at least ten consecutive base pairs.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the term "protein" refers to a large molecule composed of one or more chains of amino acids in a specific order. The order is determined by the base sequence of nucleotides in the gene coding for the protein. Proteins are required for the structure, function, and regulation of the body's cells, tissues, and organs. Each protein has a unique function.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such DNA strand may be single-stranded or it may be part of a double-stranded DNA template. In applications of the present disclosure requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UITma, and variations and derivatives thereof.

Typically, the annealing of the primers to the target DNA sequence is carried out for about 2 minutes at about 37-55° C., extension of the primer sequence by the polymerase enzyme (such as Taq polymerase) in the presence of nucleoside triphosphates is carried out for about 3 minutes at about 70-75° C., and the denaturing step to release the extended primer is carried out for about 1 minute at about 90-95° C. However, these parameters can be varied, and one of skill in the art would readily know how to adjust the temperature and time parameters of the reaction to achieve the desired results. For example, cycles may be as short as 10, 8, 6, 5, 4.5, 4, 2, 1, 0.5 minutes or less.

Also, "two temperature" techniques can be used where the annealing and extension steps may both be carried out at the same temperature, typically between about 60-65° C., thus reducing the length of each amplification cycle and resulting in a shorter assay time.

Typically, the reactions described herein are repeated until a detectable amount of product is generated. Often, such detectable amounts of product are between about 10 ng and about 100 ng, although larger quantities, e.g. 200 ng, 500 ng, 1 mg or more can also, of course, be detected. In terms of concentration, the amount of detectable product can be from about 0.01 pmol, 0.1 pmol, 1 pmol, 10 pmol, or more. Thus, the number of cycles of the reaction that are performed can be varied, the more cycles are performed, the more amplified product is produced. In certain embodiments, the reaction comprises 2, 5, 10, 15, 20, 30, 40, 50, or more cycles.

For example, the PCR reaction may be carried out using about 25-50 μl samples containing about 0.01 to 1.0 ng of template amplification sequence, about 10 to 100 pmol of each generic primer, about 1.5 units of Taq DNA polymerase (Promega Corp.), about 0.2 mM dDATP, about 0.2 mM dCTP, about 0.2 mM dGTP, about 0.2 mM dTTP, about 15 mM $MgCl_2$ about 10 mM Tris-HCl (pH 9.0), about 50 mM KCl, about 1 μg/ml gelatin, and about 10 μl/ml Triton X-100 (Saiki, 1988).

Those of skill in the art are aware of the variety of nucleotides available for use in the cyclic polymerase mediated reactions. Typically, the nucleotides will consist at least in part of deoxynucleotide triphosphates (dNTPs), which are readily commercially available. Parameters for optimal use of dNTPs are also known to those of skill, and are described in the literature. In addition, a large number of nucleotide derivatives are known to those of skill and can be used in the present reaction. Such derivatives include fluorescently labeled nucleotides, allowing the detection of the product including such labeled nucleotides, as described below. Also included in this group are nucleotides that allow the sequencing of nucleic acids including such nucleotides, such as chain-terminating nucleotides, dideoxynucleotides and boronated nuclease-resistant nucleotides. Commercial kits containing the reagents most typically used for these methods of DNA sequencing are available and widely used. Other nucleotide analogs include nucleotides with bromo-, iodo-, or other modifying groups, which affect numerous properties of resulting nucleic acids including their antigenicity, their replicatability, their melting temperatures, their binding properties, etc. In addition, certain nucleotides include reactive side groups, such as sulfhydryl groups, amino groups, or N-hydroxysuccinimidyl groups, that allow the further modification of nucleic acids comprising them.

For the purposes of the present disclosure, sequence identity or homology is determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, (1990) *Proc. Natl. Acad. Sci. USA* 87: 2264-2268, modified as in Karlin & Altschul, (1993) *Proc. Natl. Acad. Sci. USA* 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, (1988) *Proc. Natl. Acad. Sci. USA* 85: 2444-2448.

Advantageous for use according to the present disclosure is the WU-BLAST (Washington University BLAST) version 2.0 software. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., (1990) *J. Mol. Biol.* 215: 403-410; Gish & States (1993); *Nature Genetics* 3: 266-272; Karlin & Altschul, (1993) *Proc. Natl. Acad. Sci. USA* 90: 5873-5877; all of which are incorporated by reference herein).

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$). "Homology" or "identity" can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, (1983) *Proc Natl Acad Sci USA* 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the disclosure and can be derived from DNA sequences, by thymidine (T) in the DNA sequence being considered equal to uracil (U) in RNA sequences. Without undue experimentation, the skilled artisan can consult with many other programs or references for determining percent homology.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Producing the Primers and Probes of the Disclosure

The primers and probes described herein may be readily prepared by, for example, directly synthesizing the fragment by chemical means or by introducing selected sequences into recombinant vectors for recombinant production. Methods for making a vector or recombinants or plasmid for amplification of the fragment either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6; 312,683; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Feigner et al., J. Biol. Chem. 1994; 269:2550-2561; Frolov et al., Proc. Natl. Acad. Sci. USA 1996; 93:11371-11377; Graham, Tibtech 1990; 8:85-

87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312.

DISCUSSION

The embodiments of the present disclosure encompass the use of isolated polypeptides derived from the termite R. flavipes alone, or in combination, in systems for the in vitro conversion of biomaterial containing a lignin component to a fermentable product useful as a source of a biofuel. Accordingly, the embodiments of the present disclosure encompass compositions comprising combinations of termite-derived enzymes, such as but not limited to, an endoglucanase, an exoglucanase, a laccase, and a β-glucosidase and/or expressible nucleic acid elements encoding such enzymes, and in vitro methods of use thereof for converting a wood (lignocellulose) source to sugar and other moieties. It is well known that free glucose may then, for example, be fermented to ethanol for use as a bio-fuel.

Lignocellulose Processing by Termites

The biologically mediated degradation of lignocellulose into fermentable or otherwise utilizable sugars is a multistep process that requires many types of enzymes. The first step of lignin depolymerization enables hemicellulose degradation. Lignin breakdown requires oxygen, which is supported by evidence that termite guts are not completely anaerobic environments. Lignin degradation and/or modification have been documented in termite guts (see, for example: Esenther & Kirk (1974) Ann. Entom. Soc. Am. 67: 989-991; Breznak & Brune (1994) Ann. Rev. Entomol. 39: 453-487; Brune et al., (1995) Appl. Environ. Microbiol. 61: 2681-2687). Although no enzymes responsible for termite lignin oxidation have been conclusively identified, enzymes such as the laccases and peroxidases are known to degrade lignin in fungi. Other relevant enzymes may include, but are not limited to, those involved in xenobiotic detoxification, such as alcohol dehydrogenase, catalase, superoxide dismutase, cytochrome P450, epoxide hydrolase, reductase, glutathione-S-transferase, esterase, and the like. Over 25 candidate termite genes associated with lignin degradation encoding for such as a salivary laccase, have been identified from R. flavipes through the sequencing work as encompassed in the present disclosure.

The second step in the conversion of wood to a fermentable product is hemicellulose degradation, is important for making cellulose accessible for depolymerization. Complete biodegradation of hemicellulose requires the combined activity of endo- and exo-β-1,4-xylanases, β-xylosidases, α-arabinofuranosidases, α-uronidases, and esterases such as acetylxylan esterase, ferulic acid esterase, and p-coumaric acid esterase. Specific enzymatic conversions are recognized as follows: (1) endo-xylanases hydrolyze the β-1,4-xylose linkages in the xylan backbone; (2) exo-xylanases hydrolyze reduced β-1,4-xylan linkages releasing xylobiose; (3) β-xylosidases act on xylobiose to liberate xylose and other short-chain oligosaccharides; (4) α-arabinofuranosidases hydrolyze terminal non-reducing α-arabinofuranose from arabinoxylans; (5) α-uronidases release α-glucuronic, α-mannuronic and α-galacturonic acids; and (6) esterases hydrolyze phenolic ester bonds, namely those associated with acetyl xylans, ferulic acid xylans and p-coumaric xylans. Several esterases and over 50 candidate termite and symbiont hemicellulase genes from glycosyl hydrolase families 2, 3, 5, 10, 11, 26, and 43 have been identified from R. flavipes through the screening of libraries, as described in the present disclosure.

The third step, cellulose depolymerization, requires the action of three primary enzymes: endo-β-1,4-glucanases, exo-β-1,4-glucanases, and β-glucosidases. Complete or nearly complete hydrolysis of cellulose typically requires synergistic collaboration by each of these three types of cellulases. Specific enzymatic conversions include: (1) endoglucanases that hydrolyze β-1,4-glycosyl linkages in the primary cellulose backbone, releasing glucose, cellobiose, cellotriose or other longer oligomers, (2) exoglucanases or "cellobiohydrolases" that target the terminal regions of polymeric chains to liberate either glucose or cellobiose, and (3) β-glucosidases hydrolyze cellobiose and cellotriose to liberate glucose monomers. In R. flavipes, over 55 candidate termite and symbiont cellulase genes from glycosyl hydrolase families 1, 7, 9, and 45 have been identified from R. flavipes through sequencing of the EST libraries of the present disclosure. The biological degradation/depolymerization of lignocellulose, therefore, is a highly complex process that involves many diverse enzymes. Because of the complexity of these enzyme systems, it has generally been considered impractical to characterize lignocellulose degradation from termites by enzyme biochemistry alone.

cDNA Libraries and Sequence Statistics

Two R. flavipes cDNA libraries were initially created, one representing symbiont-free termite gut tissue, and the other a combination of prokaryotic and eukaryotic hindgut symbionts. A total of 10,610 high-quality Expressed Sequence Tags (ESTs) were generated from the two libraries. The 5,871 ESTs produced from the termite gut library were assembled into 875 contigs and 2,169 singlets to produce 3,044 putatively unique transcripts. In the symbiont EST database, a contig assembly performed using the same parameters identified 358 contigs and 3,153 singlets (for a total of 3,511 putative transcripts). Similarity searches showed that a high proportion of the transcripts from both libraries (38% and 48%, respectively) did not produce significant matches in the NCBI nr database The majority of the sequences generated from the termite gut tissue libraries had sequence similarity to genes previously identified from insects or from other invertebrates. The analysis also revealed a number of gut library sequences that may be attributed to residual endosymbiotic protists within the guts that had not been completely cleared during the dissection and cleaning process.

Similarly, the symbiont-specific library contained a small fraction of transcripts matching insect and invertebrate sequences. Despite this contamination, more than 80% of the annotated sequences from the symbiont-specific EST library were found to be most similar to predicted proteins from microbes. BLAST analyses demonstrated a significant difference between the two libraries and emphasized the utility of the two libraries for novel gene discovery.

Glycosyl Hydrolase Sequence Composition

The EST databases described in the preceding section were searched for cellulases, hemicellulases, β-glucosidases, and all other carbohydrate-active, enzyme-coding sequences as listed in the CAZy database. The CAZy database maintained by the CNRS-Universites Aix-Marseilles 1 & 11 describes the families of structurally-related catalytic and carbohydrate-binding modules (or functional domains) of enzymes that degrade, modify, or create glycosidic bonds.

For the termite gut library, 298 total clones were compiled that corresponded to 127 potential transcripts and 42 different carbohydrate-active domains. The symbiont library revealed 261 clones associated with carbohydrate catabolism, composing 116 unique sequences that included 26 different carbohydrate-active domains. In the host and symbiont databases, the majority of recognized protein domains corresponded to glycoside hydrolase families (GHFs), including various cellulases, hemicellulases, α-carbohydrolases, and chitinases.

Regarding cellulases, over 55 candidate termite and symbiont cellulase genes from GHF 1 (β-glucosidase), 7 (exoglucanase), 9 and 45 (endoglucanase) have been identified. With respect to hemicellulases, over 50 candidate termite and symbiont hemicellulase genes from glycosyl hydrolase families 2 (β-1,4-galactosidase/mannosidase/glucuronidase), 3 (β-1,4-xylosidase), 5 (β-1,4-endoxylosidase), 10 (β-1,3-endoxylanase), 11 (β-1,4-xylanase), 26 (β-1,3-xylanase), and 43 (β-1,3-endoxylosidase) now have been identified.

Lignase, Antioxidant, and Detoxification Genes

For the termite gut library, a total of 49 enzyme-coding genes were identified that could have a role in lignin degradation and/or possibly protection from toxic lignin degradation products. The putative lignases identified include laccases, peroxidases, and glutathione peroxidases. This identification of candidate lignase genes also agrees with earlier biochemical findings showing various degrees of modification of lignin, mono-lignol, and/or phenolic compounds in the guts of diverse termites, including R. flavipes. Also, numerous genes encoding detoxification and antioxidant enzymes (cytochrome P450, esterases/carboxylesterases, glutathione-S-transferase, alcohol dehydrogenases, epoxide hydrolase, glutathione transferase, superoxide dismutase, catalase, and alcohol dehydrogenase) were identified from sequencing of the EST libraries of the present disclosure. Because lignin degradation is known to result in free radical generation, the expression of antioxidant enzymes in the R. flavipes gut provides supporting evidence of lignin degradation.

Production and Characterization of Recombinant Lignocellulases

Three recombinant digestive enzymes were obtained from cloned R. flavipes genes. These enzymes include three salivary gland-expressed genes identified through cDNA library sequencing. The first protein, Cell-1, is an endoglucanase; it was produced in both baculovirus-infected moth larvae (C-PERL™ system) and E. coli (PET™ system; Novagen). The recombinant Cell-1 enzyme is more active toward the model substrate carboxy-methyl (CM) cellulose when the enzyme is expressed using the baculovirus/insect-expressed form than when in the E. coli-expressed form, as shown in FIG. 33A. While not wishing to be bound by any one theory, the greater Cell-1 activity of the enzyme expressed in the baculovirus system is likely attributable to more correct post-translational processing of the protein, including the glycosylation state thereof, by insect cells. The second protein, a β-glucosidase, shows very strong activity toward its natural substrate cellobiose, as shown in FIG. 33B. The third recombinant protein, a salivary laccase potentially involved in lignin degradation, showed strong activity toward the model laccase substrates pyrogallol, as shown in FIG. 33C, guaiacol, dimethoxyphenol, and syringaldazine, and ABTS.

Four esterase genes were characterized for esterase gene expression, isoform composition, subcellular distribution, and activity across the gut of a lower termite. Analyses of translated amino acid sequences revealed one sequence (RfEst1) with significant sequence similarity to insect juvenile hormone (JH) esterases, and three esterases (RfEst2, RfEst 3 and RfEst 4) with similarities to fungal phenolic acid esterases. Gene expression studies revealed ubiquitous midgut expression for all four genes, significant hindgut expression for RfEst1 and RfEst4, and generally lowest overall expression in the foregut/salivary gland.

Non-denaturing PAGE of the esterases revealed that, in relation to isoform composition outside the gut, there is greater isoform diversity inside the gut. Moreover, in agreement with gene expression findings, highest isoform diversity and total esterase activity both occurred in the midgut. With respect to substrate specificity, α-naphthyl esters with aliphatic chain lengths of three (propionate) and four (butyrate) carbons were metabolized at the greatest rates, followed by the two carbon (acetate) ester. Additionally, of the three subcellular fractions investigated by esterase native PAGE (mitochondrial, cytosolic and microsomal), all showed expression of a number of isoforms. Finally, a substantial band of soluble esterase activity was observed in hindgut lumen supernatant, suggesting that esterases and other enzymes can be readily transferred from donor to recipient termites by proctodeal trophallaxis.

These findings indicate that the esterase genes of the present disclosure, and corresponding enzyme activities, are encoded in the termite genome, and are specifically expressed by gut and/or salivary gland tissue, rather than being derived from gut endosymbionts. The results further suggest hormone and hemicellulose hydrolysis occurs in the termite gut.

Juvenile Hormone (JH) Esterases and Semiochemical/Hormone Processing.

JH esterases are members of the carboxylesterase family. They are typically synthesized in the fat body and secreted into hemolymph where they catabolize JH with high affinity (Goodman & Granger, 2005 (eds.) Comprehensive molecular insect science, Vol. 3, Elsevier-Pergamon, New York, pp. 319-408). In termites, JH has established links to worker-to-soldier caste differentiation (Park & Raina (2004) J. Insect Physiol. 50: 561-566; Park & Raina (2005) J. Insect Physiol. 51: 385-391; Mao et al., (2005) Ann. Entomol. Soc. Am. 98: 340-345; Elliott & Stay (2008) Gen. Comp. Endocrinol. 152: 102-110; Cornette et al., (2008) J. Insect Physiol. 54: 922-930) and vitellogenesis in adult female reproductives (Elliott & Stay (2007) Gen. Comp. Endocrinol. 152: 102-110; Cornette et al., (2008) J. Insect Physiol. 54: 922-930).

With respect to hormonal processing and caste regulation, previous sequencing from an R. flavipes gut library revealed a number of endogenous (i.e. termite-derived) genes encoding enzymes that participate in both JH biosynthesis and degradation. JH biosynthetic genes have been identified from the R. flavipes digestive tract. JH degradation genes, also from the gut, include P450s, epoxide hydrolases, and the putative JH esterase RfEst1.

The RfEst1 nucleotide sequence (SEQ ID NO.: 26) provided by the present disclosure shares significant translated identity across its entire length with several putative insect JH esterases, including an RNAi-validated JH esterase from the honey bee A. mellifera (Mackert et al., (2008) Comp. Biochem. Physiol. B Biochem. Mol. Bio. 150: 33-44). The RfEst1 protein shares several sequence features in common with other putative JH esterases. These common features include a signal peptide (MAETVTVTVAQ (SEQ ID NO.: 44), distinct JH esterase catalytic esterase motifs, such as a catalytic triad (G-SAG, E/D, and G-H-D-), and two putative substrate recognition motifs (RF, DQ) (Campbell et al., 2001 Insect Biochem. Mol. Bio. 31, 513-20; Goodman and Granger, 2005 in Gilbert et al., (eds.) Comprehensive molecular insect science, Vol. 3, Elsevier-Pergamon, New York, pp. 319-408, Munyiri & Ishikawa, (2007) Insect Biochem. Mol. Bio. 37: 497-505; Mackert et al., (2008) Comp. Biochem. Physiol. B Biochem. Mol. Bio. 150: 33-44).

Phenolic Acid Esterases

Phenolic acid esterases, also known as feruloyl, coumaryl or cinnamoyl esterases play roles in hemicellulose and pectin depolymerization by cleaving ester bonds that connect ferulic and coumaric acids to hemicellulose and pectin sugar monomers (Saha (2003) J. Indust. Microbiol. Biotechnol. 30: 279-291; Crepin et al., (2004) Appl. Microbiol. Biotechnol. 63: 647-652; Anderson & Akin (2008) J. Ind. Microbiol. Biotechnol. 35: 355-366, 2008; Benoit et al., (2008) Biotechnol. Letters 30: 387-396). Of these two potential substrates, hemicellulose is a significant component of the termite diet. Hemicellulose, also referred to as xylan, is a complex β-linked sugar polymer that composes approximately 25% of lignocellulose and represents a significant obstacle to cellulose digestion by cellulolytic organisms. Phenolic acid esterases catalyze a critical step in cellulose and hemicellulose depolymerization by dissociating both polymers from each other and lignin, making each polymer more accessible to hemicellulase and cellulase enzymes.

"General" esterases are a large group of insect esterases that are typically active toward naphthyl ester substrates. Accordingly, the isoforms identified by native PAGE analysis of the present disclosure can be classified as general esterases (Oakeshott et al., (2005) in Gilbert et al., (eds.) Comp. Mol. Insect. Sci. Vol. 5, Elsevier-Pergamon, New York, pp. 309-382), and possibly permethrin esterases (Valles et al., (2001) Insect Biochem. Mol. Biol. 31: 715-725). Aside from roles in lipid and xenobiotic metabolism, the roles of insect general esterases remain mostly undefined (Oakeshott et al., 2005). While not wishing to be bound by any one theory, general esterases from the termite gut may participate in hemicellulose depolymerization by acting as phenolic acid esterases.

Little ferulic/phenolic acid esterase activity has been reported from animals and insects, although a large number of such activities have been identified previously from various microbial sources (reviewed by Crepin et al., (2004) Appl. Microbiol. Biotechnol. 63: 647-652; Benoit et al., (2008) Biotechnol. Letters 30: 387-396). In amino acid alignments of two A. niger fae with the four translated termite esterases RfEst1, RfEst2, RfEst3 and RfEst4 (SEQ ID NOs.: 27, 29, 31, and 33, respectively) of the present disclosure, none showed statistically significant Blast homology; however, faeA does align at key positions with the short 20-23 kDa peptides encoded by RfEst2, RfEst 3 and RfEst 4 (SEQ ID NOs.: 29, 31, and 33, respectively), as shown in FIGS. 1A and 1B. In particular, five amino acids show 100% conservation across the alignment, and there is some conservation around the faeA catalytic site.

The termite esterases RfEst2, RfEst3 and RfEst4 are smaller proteins and, based on their lack of N-terminal homology with faeA, they may be subunits of larger functional multimeric proteins. A. niger faeA shows preferential activity toward hemicellulose side-chain esters (de Vries et al., (2002) Biochem. J. 363: 377-386), the termite diet is largely composed of hemicellulose, and there is a large complement of hemicellulase genes encoded within the R. flavipes gut transcriptome. Additional information supporting that phenolic acid esterases exist in the R. flavipes gut is the significantly elevated esterase activity toward α-naphthyl butyrate, indicating that RfEst2, RfEst3 and RfEst4 (SEQ ID Nos.: 26, 28, 30, and 32, respectively) encode termite-derived phenolic acid esterases.

Phenolic acid esterases have been identified from gut symbiotic bacteria of higher termites including from Clostridium xylanolyticum, a bacterial gut symbiont of the grass feeding higher termite Tumilitermes pastinator. Clostridium bacteria have also been sampled from R. flavipes. However, there has been no evidence suggesting that symbiotic bacteria of lower termites possess lignocellulolytic abilities (Watanabe & Tokuda (2007) Nature 394: 330-331). Other termite fungal symbiont esterases have been identified (Sreerama & Veerabhadrappa, (1993) Int. J. Biochem. 25: 1637-1651); however, their actual substrates are unknown, and they represent less than 5% of total gut esterase activity from their host termite. The results of the present disclosure do not indicate microbial origins for the four R. flavipes esterase genes RfEst1, RfEst2, RfEst3 and RfEst4, based on: (1) the genes were identified from a termite gut library substantially free of symbiont-derived nucleic acid sequences, (2) the genes were not sampled from a hindgut symbiont library, and (3) esterase activity is clearly abundant in symbiont-free termite gut regions.

Cell-1 is a host-derived β-1,4-endoglucanase (Glycohydrolase Family 9 [GHF9]) from the lower termite Reticulitermes flavipes. Embodiments of the present disclosure provide the heterologous production of Cell-1 using eukaryotic (Baculovirus Expression Vector System; BEVS) and prokaryotic (E. coli) expression systems. The BEVS-expressed enzyme was more readily obtained in solubilized form and more active than the E. coli-expressed enzyme. $K_m$ and $V_{max}$ values for BEVS-expressed Cell-1 against the model substrate CMC were 1.496% w/v and 1.469 pmol/min/mg. The BEVS-expressed enzyme has activity comparable to the native enzyme, is optimally active around neutral pH and 50° C.-60° C., is inhibited by EDTA, and displays enhanced activity up to 70° C. in the presence of $CaCl_2$. It is contemplated that GHF9 or a variant thereof may be combined with enzymes such as, but not limited to, host and symbiont digestive enzymes from R. flavipes that include GHF7 exoglucanases, GHF1 β-glucosidases, phenol-oxidizing laccases, and others.

cDNAs encoding two gut laccase isoforms (RfLacA and RfLacB) were sequenced from the termite Reticulitermes flavipes. Alignments with crystallography-verified laccases confirmed that peptide motifs involved in metal binding are 100% conserved in both isoforms. Using a baculovirus-insect expression system, the two isoforms were functionally expressed and purified to near homogeneity. Both isoforms showed identically strong activity towards the lignin monomer sinapinic acid and four other phenolic substrates. By contrast, both isoforms displayed much lower or no activity against four melanin precursors, suggesting that neither isoform is involved in integument formation. Modification of lignin alkali by RfLacA was also observed. These findings provide evidence that R. flavipes gut laccases are host-derived, produced in the salivary gland, secreted into the foregut, and involved in lignocellulose digestion.

Two apparent laccase isoform-coding cDNAs were sequenced from the termite R. flavipes; they were greater than 99% similar at the nucleic and amino acid levels. Both translated amino acids contain secretory signal peptides. This finding, in combination with gene expression and phenoloxidase activity in salivary gland tissue, demonstrates that laccases are secreted from the salivary gland into the R. flavipes digestive tract.

Using a baculovirus-insect expression system, recombinant versions of the RfLacA and RfLacB isoforms were functionally expressed and purified to near homogeneity. While both isoforms are clearly laccases based upon sequence homology and activity profiles, they are also clearly distinct from other laccases. In particular, RfLacA and RfLacB both (i) have a higher optimal pH of 7.0-7.5 that is within the known pH range of the *R. flavipes* gut (Brune et al., (1995) *Appl. Environ. Microbiol.* 61: 2681-2687), and (ii) apparently lack a T1 copper, and (iii) require hydrogen peroxide for activity. In addition, both laccases were unable to oxidize the non-specific laccase substrate ABTS, and the diagnostic substrate syringaldazine (Harkin et al., (1974) *Mycologia* 66: 469-476). Finally, RfLacA responds differently than other laccases to known laccase inhibitors, showing greater EDTA inhibition than most laccases and also showing enhanced activity in the presence of other usual inhibitors.

Both laccases showed good catalytic activity against the lignin monomer sinapinic acid, and against the four phenolic substrates hydroquinone, pyrocatechol, 2,6-DMP, and pyrogallol. Finally, experimental results showing modification of lignin alkali by RfLacA provide a parallel line of evidence showing activity against lignin itself. These findings suggest that, unlike many known insect laccases, RfLacA and RfLacB are not involved in integument formation and support that the two laccase isoforms play a role in lignocellulose-related phenol oxidation in the termite gut.

The data of the present disclosure verify that *R. flavipes* laccases are polymorphic (exist in at least two isoforms), evolutionarily distinct, host-derived, produced in secretory tissue, active on lignin, and do not participate in integument formation. These data also support RfLacA and RfLacB isoforms as new types of copper-limited white laccases, and that they are involved in lignocellulose-related phenol oxidation in the termite gut.

Relation to Previous Studies on Termite Esterase Biochemistry

Esterase biochemistry has been studied in several termite species, including *R. flavipes*. Sreerama & Veerabhadrappa (1991) *Int. J. Biochem.* 21: 833-844; (1993) *Int. J. Biochem.* 25: 1637-1651) provided the evidence of esterase activity in the termite gut. These studies investigated midgut and fungal symbiont esterases from the higher termite *Odontotermes horni*. Two approximately 78 kDa midgut esterases were purified to homogeneity by column chromatography; upon treatment with β-mercaptoethanol, each protein was split into two subunits of approximately 40 kDa. Both termite midgut esterases showed optimal catalytic activity at pH 7, and greater activity toward α-naphthyl acetate than propionate or butyrate.

Sreerama & Veerabhadrappa also purified esterases from the *Odontotermes horni* fungal symbiont *Xylaria nigripes*. Here, four esterases ranging in size from about 85 kDa to about 88 kDa were purified to homogeneity and found to have considerably different biochemical and catalytic properties than the endogenous midgut esterases. Starvation studies revealed little impact on host and symbiont esterase activity, while distribution studies revealed that more than 98% of total esterase activity was host-derived. These studies suggested little importance for fungal symbionts in the hydrolytic metabolism of carboxylester substrates in *Odontotermes horni*, which agrees with the identification of esterase genes from a symbiont-free *R. flavipes* gut cDNA library, and identification of esterase gene expression and activity from gut regions that do not house symbionts.

Other studies have examined esterases in other termite species, from either the hemolymph or whole-body preparations. Wyss-Huber (1981) (*Insectes Soc.* 28: 71-86) investigated hemolymph-soluble esterases in the higher and a lower termite species *Macrotermes subhyalinus* and *Zootermopsis angusticollis*, and showed caste- and phenotype-specific native PAGE banding patterns in both species, supporting a role for possible hemolymph JH esterases in caste differentiation and/or caste homeostasis. Ruvolo-Takasusuki & Collett (2000) (*Biochem. Genet.* 38: 367-375) investigated esterases from whole-body preparations of different castes of the higher termite *Nasutitermes globiceps*. Since whole-body preparations were used, it was not possible to determine which *N. globiceps* esterases, if any, are expressed in the gut. However, a diversity of esterase isoforms was found by native PAGE.

The present disclosure, therefore, encompasses a series of isolated nucleic acid molecules, the nucleotide sequences of which encode for enzymes of the gut of the termite *R. flavipes* that probably are associated with the digestion of lignocellulose by the insect. The isolated nucleic acid molecules of the disclosure have been operably inserted into expression vector systems and expressed in two types of host, namely a prokaryotic (bacterial) cell system, and a eukaryotic (insect cell) system. The expressed polypeptide products were characterized as to their respective enzymic activities, the data of which further showed that, in the termite, these enzymes probably have a role in lignocellulose digestion. It is contemplated that the isolated enzymes of the disclosure may be expressed from expression vectors transfected into a host cell system, whereby their activity (as found in the gut of the parent termite) may be substantially replicated in an in vitro system. It is also contemplated that an operable system of the expressed enzymes may be reconstructed in vitro to provide a method of converting a lignocellulose-containing plant material to a fermentable breakdown product, and in particular to sugars such as, but not limited to, glucose.

The present disclosure, therefore, further encompasses the use of the isolated polypeptides from the termite *R. flavipes* alone, or in combination, in systems for the in vitro reduction of biomaterial containing a lignocellulose component to a product that may be fermented to provide a source of a biofuel. Accordingly, the present disclosure further includes data that shows that a wood (lignocellulose) source can provide glucose moieties when treated in vitro with a combination of an endoglucanase, an exoglucanase, a laccase, and a β-glucosidase. It is well known that free glucose may be fermented to such as ethanol for use as a bio-fuel.

Accordingly, the present disclosure provides isolated nucleic acid molecules derived from the gut of the termite *R flavipes*, recombinant nucleic acid molecules comprising a vector and an isolated heterologous nucleic acid molecule operably inserted therein, whereby, when transformed into an appropriate host cell system, the heterologous nucleic acid sequence is expressed as a polypeptide having an activity similar to that when expressed in the gut of the termite *R. flavipes*. It is within the scope of the disclosure for the recombinant nucleic acid molecules to comprise more than one heterologous nucleic acid molecule such that more than one polypeptide may be expressed by the host system. The expressed polypeptides may be substantially purified, or used in a substantially unpurified form, to be admixed with a lignocellulose source to be converted to a fermentable product such as a sugar or a mixture of sugars.

One aspect of the present disclosure, therefore, encompasses methods of converting a lignified plant material to a fermentable product, the method comprising the steps of: (a) obtaining a series of isolated polypeptides of a termite, wherein the series of polypeptides cooperate to convert a plant lignocellulose to a fermentable product; and (b) incubating the series of polypeptides with a source of lignified plant material, under conditions allowing the polypeptides to cooperatively produce a fermentable product from the lignified plant material.

In embodiments of this aspect of the disclosure, the isolated polypeptides can be derived from the termite *Reticulitermes flavipes*.

In embodiments of this aspect of the disclosure, the isolated polypeptides of the series of isolated polypeptides can be selected from the group consisting of: an endoglucanase, an exoglucanase, a laccase, an esterase, and a glucosidase. In one embodiment of this aspect of the disclosure, the series of the isolated polypeptides comprises an endoglucanase, an exoglucanase, a laccase, an esterase, and a glucosidase.

In the various embodiments of this aspect of the disclosure, the isolated polypeptides of the series of isolated polypeptides can be recombinant polypeptides, where each polypeptide is expressed from an expression vector of a recombinant expression system, and wherein the recombinant expression system is selected from a eukaryotic cell-based system and a prokaryotic cell-based system.

In one embodiment of the disclosure, the expression vector is a baculovirus expression vector and the recombinant expression system is a eukaryotic cell-based system.

In the various embodiments of the disclosure, the series of isolated polypeptides comprise an endoglucanase having an amino acid sequence having about 75% sequence identity with the amino acid sequence SEQ ID NO.: 2.

In one embodiment of the disclosure, the endoglucanase can comprise the amino acid sequence SEQ ID NO.: 2.

In the various embodiments of the disclosure, the series of isolated polypeptides comprises an exoglucanase having an amino acid sequence having about 75% sequence identity with the amino acid sequence SEQ ID NO.: 4.

In one embodiment of the disclosure, the series of isolated polypeptides comprises an exoglucanase having the amino acid sequence SEQ ID NO.: 4.

In the various embodiments of the disclosure, the series of isolated polypeptides comprises a laccase having an amino acid sequence having about 75% sequence identity with an amino acid sequence selected from the group consisting of: SEQ ID NOs.: 8, 10, 12, 15, 17, 19, 21, and 23.

In one embodiment of the disclosure, the series of isolated polypeptides comprises a laccase having the amino acid sequence selected from the group consisting of: SEQ ID NOs.: 8, 10, 12, 15, 17, 19, 21, and 23.

In the various embodiments of the disclosure, the series of isolated polypeptides comprises an esterase having an amino acid sequence having about 75% sequence identity with the amino acid sequence selected from the group consisting of: SEQ ID NOs.: 27, 29, 31, and 33.

In one embodiment of the disclosure, the series of isolated polypeptides comprises an esterase having the amino acid sequence selected from the group consisting of: SEQ ID NOs.: 27, 29, 31, and 33.

In one embodiment of the disclosure, the series of isolated polypeptides comprises a glucosidase having the amino acid sequence SEQ ID NO.: 6.

In the various embodiments of the disclosure, the fermentable product may comprise at least one carbohydrate selected from the group consisting of: a glucose, a mannose, a xylose, a galactose, a rhamnose, an arabinose, a glucuronic acid, a mannuronic acid, and a galacturonic acid.

In the various embodiments of the disclosure, the fermentable product may comprise glucose.

Another aspect of the present disclosure encompasses systems for producing a fermentable product from a lignified plant material, wherein the system may comprise at least two isolated polypeptides selected from the group consisting of: an endoglucanase, an exoglucanase, a laccase, an esterase, and a glucosidase of the termite *Reticulitermes flavipes* and wherein the at least two isolated polypeptides can cooperate to convert a constituent of the lignified plant material to a fermentable product or a precursor thereof.

In embodiments of this aspect of the disclosure, the nucleotide sequence encoding the endoglucanase may hybridize under high stringency conditions to a nucleotide sequence according to SEQ ID NO.: 1, the nucleotide sequence encoding the exoglucanase may hybridize under high stringency conditions to a nucleotide sequence according to SEQ ID NO.: 3, the nucleic acid molecule encoding the laccase may hybridize under high stringency conditions to a nucleotide sequence selected from the group consisting of: SEQ ID NOS.: 7, 9, 11, 13, 14, 16, 18, 20, and 22, the nucleic acid molecule encoding the esterase may hybridize under high stringency conditions to a nucleotide sequence selected from the group consisting of: SEQ ID NOS.: 26, 28, 30, and 32, and the nucleotide sequence encoding the glucosidase may hybridize under high stringency conditions to SEQ ID NO.: 5. In embodiments of this aspect of the disclosure, each of the isolated nucleic acid molecules thereof may be operably inserted into an expression vector.

Still another aspect of the disclosure encompasses a recombinant cell comprising an isolated nucleic acid molecule hybridizing under high stringency conditions to a nucleotide sequence encoding a polypeptide selected from the group consisting of: an endoglucanase, an exoglucanase, a laccase, an esterase, and a glucosidase of the termite *Reticulitermes flavipes*, wherein the nucleotide sequence encoding the endoglucanase is according to SEQ ID NO.: 1, the nucleotide sequence encoding the exoglucanase is according to SEQ ID NOS.: 3, the nucleic acid molecule encoding the laccase is selected from the group consisting of: SEQ ID NOS.: 7, 9, 11, 13, 14, 16, 18, 20, and 22, the nucleic acid molecule encoding the esterase is selected from the group consisting of: SEQ ID NOS.: 26, 28, 30, and 32, and the nucleotide sequence encoding the glucosidase is according to SEQ ID NO.: 5.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include±1%, ±2%, ±3%, ±4%, ±5%, ±6%, ±7%, ±8%, ±9%, or ±10%, or more of the numerical value(s) being modified.

EXAMPLES

Example 1

Termites: *Reticulitermes flavipes* colonies were collected from Gainesville, Fla., and maintained in sealed plastic boxes (30×24×10 cm) in complete darkness (L:D=0:24), at 22° C. and 69% relative humidity. Colonies were maintained without soil for more than six months and provisioned with moist brown paper towels and pine wood shims. The identity of colonies as *R. flavipes* was verified by a combination of soldier morphology and 16S-mt-rDNA gene sequencing. Worker termites were used in this study because of their significant lignocellulose digestion capability and developmental plasticity. Termites were considered workers if they did not possess any sign of wing buds or distended abdomens, and had pronotal widths wider than mesonotal widths (Laine et al., (2003) *Bull. Entomol. Res.* 93; 267-378).

Example 2

Esterase gene identification: A number of putative esterase genes were sequenced from a normalized *R. flavipes* gut cDNA library. Four esterase genes were deduced from three contigs (515, 493 and 275), as well as a single EST (TG_15_C3) representing a near full-length cDNA. The three contigs (515, 493 and 275) were assembled from 4, 4 and 3 individual EST sequences, respectively. The genes are referred to, respectively, as Rf (*R. flavipes*) Est (esterase) genes 1, 2, 3 and 4, and comprise the nucleotide sequences SEQ ID NOs.: 26, 28, 30, and 32, respectively. The ORF amino acid translations of the four genes RfEst1-4 have the amino acid sequences according to SEQ ID NOs.: 27, 29, 31, and 33, respectively.

Sequence alignments were made under default settings using MEGALIGN™ in the LASERGENE™ software package (Madison, Wis.). Signal peptides were determined using PROTEAN™ in the Lasergene software package. Glycosylation sites in translated proteins were predicted using an online prediction tool available at (Hamby & Hirst (2008) BMC *Bioinformatics* 9: 500). The sequence identities of the open reading frames of the four genes are less than 25%, and non-overlapping in their sequence composition, as shown in FIGS. 1A and 1B.

The deduced protein sequences (SEQ ID NOs.: 27, 29, 31, and 33) encoded by the four esterase genes segregate into two groups that include longer (i.e., RfEst1) and shorter open reading frames (i.e., RfEst2, RfEst 3 and RfEst 4). The alignment reveals conserved N-terminal esterase motifs in RfEst1 that are absent in RfEst2, RfEst 3 and RfEst 4, but greater degrees of conservation in the region homologous to the C-terminal end of RfEst1. In particular, beginning at consensus residue 346 there are ten completely conserved amino acids and a conserved G-H-D-esterase catalytic motif across all four esterases.

This RfEst1 group is composed of larger proteins with predicted molecular masses of about 60 kDa. The predicted RfEst1 protein (SEQ ID NO.: 27) has a molecular mass of 59 kDa, an 11 amino acid signal peptide (MAETVTVTVAQ (SEQ ID NO.: 44)), 30 N-glycosylation sites, and shares significant amino acid identity across its entire length with a number of putative insect Juvenile Hormone (JH) esterases, including representatives from the longicorn beetle *Psacothea hilaris* (GenBank Accession No: BAE94685), the red flour beetle *Tribolium castaneum* (GenBank Accession No: XP_967137), the honeybee *Apis mellifera* (GenBank Accession No: AAU81605), and the saw fly *Athalia rosae* (GenBank Accession No: BAD91555).

The second esterase group comprises RfEst2, RfEst3 and RfEst4 (SEQ ID NOs.: 29, 31, and 33). The deduced amino acid sequences for these three genes are about 18 kDa to about 3 kDa and only share similarity with the JH esterase-like proteins described above at their C-terminal ends. Other than the carboxylesterases/JH esterases noted above, there were no other full-length translated database matches for RfEst2, RfEst 3 and RfEst 4 (SEQ ID NOs.: 29, 31, and 33).

The translated RfEst2, RfEst 3 and RfEst 4 sequences were also aligned with the translated faeA sequence of *Aspergillus niger*, a lignocellulose digester (GenBank Accession No: Y09330). The G-H-D-catalytic sites in faeA and RfEst2, RfEst 3 and RfEst 4 are 100% conserved. Additionally, there are 5 completely conserved residues among all five proteins, and many other similar regions. There is also a degree of conservation in the N-terminal regions of faeA and RfEst2.

Example 3

Esterases

Quantitative PCR

TABLE 1 qPCR primer sequences for the esterases RfEst1-4 and the control gene β-actin.

| Primer Name | Alternate Name | Sequence (5'-3') | SEQ ID NO.: |
|---|---|---|---|
| RfEst1 L | Contig515L-set 4 | ATGACAGAAGAGGAGCTTGACC | 34 |
| RfEst1 R | Contig515R-set4 | CAGGAGTTCAAAGTCACTGTCG | 35 |
| RfEst2 L | Contig493-1R | GGTTAGGCGTCATTTGTAGAGG | 36 |
| RfEst2 R | Contig493-1L | GGCTCATGGTCATCTAAGAACC | 37 |
| RfEst3 L | Contig275L-set5 | AGAGACGGTTGAAGACTTGGTC | 38 |
| RfEst3 R | Contig275R-set5 | ACTGATACGTAGTGGCCTGACA | 39 |

TABLE 1-continued qPCR primer sequences for the esterases
RfEst1-4 and the control gene β-actin.

| Primer Name | Alternate Name | Sequence (5'-3') | SEQ ID NO.: |
|---|---|---|---|
| RfEst4 L | TG_15_C3 1L | GCCAGAATTCAAGCTGCTGT | 40 |
| RfEst4 R | TG_15_C3 1R | TGTCCTTGTCTTGCTGTGTCTC | 41 |
| β-actin L | N/A | AGAGGGAAATCGTGCGTGAC | 42 |
| β-actin R | N/A | CAATAGTGATGACCTGGCCGT | 43 |

The stable expression of the reference gene β-actin across gut regions was validated previously (Zhou et al., (2007) Gene 395: 29-39). qPCR primers were designed with specificity to sequence-unique regions of the target genes, and to produce products in the 100-300 bp size range, were designed using PRIMER3™ (Rozen & Skaletsky (2000) in Krawetz & Misener (eds) Bioinformatics Methods and Protocols, Methods in Molecular Biology. Humana Press, Totowa, N.J., pp 365-386). cDNA from the foregut and salivary gland, the midgut and the hindgut regions served as templates for qPCR. Gut dissections were performed as described in Example 4, below, using RNA lysis buffer (Promega; Madison, Wis.) in place of potassium phosphate. cDNA was synthesized from the total RNA of 25 individual gut regions per experimental replicate. Total RNA and cDNA were obtained using the SV total RNA isolation kit (Promega) and the ISCRIPT™ cDNA Synthesis Kit (Bio-Rad; Hercules, Calif.), respectively, following manufacturer protocols. qPCR reactions contained equal template loadings and proceeded for 30-35 cycles. PCR products were viewed on 1.5% agarose gels, imaged, and the images analyzed densitometrically.

Pooled densitometric analyses from five replicate gels on two colonies, with statistical support ($p<0.05$), are shown in FIG. 2. All four esterases are expressed in the midgut. RfEst1 is most strongly expressed in midgut and hindgut tissues, but also has foregut/salivary gland expression. The RfEst2 and RfEst 3 esterases are predominantly expressed in the midgut. RfEst4 is expressed mainly in midgut and hindgut tissues, but also has significant foregut/salivary gland expression.

Example 4

Dissections, protein preparation, centrifugation protocols, and protein assays: All manipulations were performed on ice. For tissue localization studies, 25 termite worker guts were removed and dissected into the three regions of foregut/salivary gland, midgut and hindgut. Each gut region preparation was homogenized using a Tenbroeck glass homogenizer in potassium phosphate (0.1M, pH 7.6), and then centrifuged for 15 min at 14,000×g and 4° C. The supernatant was saved for assays and the pellet discarded.

For isolation of subcellular gut protein fractions, the protocol of Kupfer & Levin (1972) Biochem. Biophys. Res. Comm. 47: 611-618 was followed with minor modifications. Fifty whole worker termite guts were homogenized in potassium phosphate as above. The homogenate was centrifuged at 1,000×g and 4° C. for 5 min and the pellet discarded. The supernatant was transferred to a fresh tube and centrifuged at 10,000×g for 10 min and 4° C. A small aliquot of the supernatant was retained and the remainder transferred to a fresh tube. The resulting 10,000×g mitochondrial pellet was washed and re-spun three times in potassium phosphate buffer before being re-suspended in potassium phosphate/ 0.1% Triton X-100 (Valles et al., (2001) Insect Biochem. Mol. Biol. 31, 715-725). Next, a volume of calcium chloride was added to the post-mitochondrial supernatant to a final concentration of 8 mM. The mixture was inverted several times, left on ice for 5 min, and then centrifuged at 10,000×g for 10 min and 4° C. The resulting supernatant was transferred to a fresh tube and used as the soluble/cytosolic enzyme source. The resulting microsomal pellet was washed and re-spun three times in potassium phosphate buffer before being re-suspended in potassium phosphate/0.1° A Triton X-100 (Valles et al., (2001) Insect Biochem. Mol. Biol. 31, 715-725).

Gut luminal contents were isolated from 100 worker termites by first holding them by the abdomen with soft larval forceps and gentle squeezing to induce defecation. The termite abdomen was then lowered into potassium phosphate buffer, where the fecal material was collected. Symbiont cells and other debris were pelleted by centrifugation for 10 min at 14,000×g and 4° C. and the remaining supernatant used as the enzyme source.

Protein content of protein preparations was estimated by a microplate Bradford assay (Bio-Rad; Hercules, Calif.) using bovine serum albumin as a standard and corresponding buffers as blanks.

Example 5

Statistical analyses: Native PAGE and colorimetric esterase assays were performed on three replicate protein preparations from two termite colonies. qPCR analyses were performed on five replicate RNA isolations and cDNA syntheses from two termite colonies. Statistical analyses consisted of one-way ANOVA followed by Tukey's multiple range test for colorimetric enzyme data and LSD t-tests for quantitative PCR data. With the exception of hindgut colorimetric data, all variances were equal and ANOVAs were verified as being significant before conducting mean separation testing.

Example 6

Figure 3:
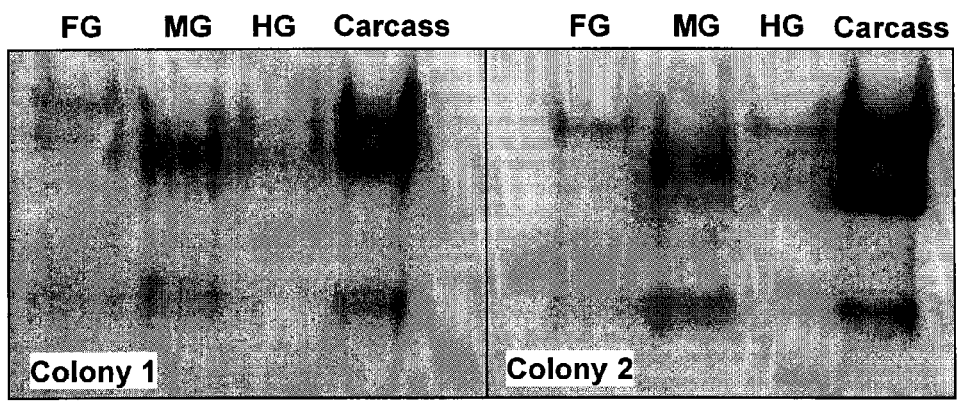
FIG. 3 is a digital image of an analysis of R. flavipes worker gut and carcass esterases by native (non-denaturing) polyacrylamide gel electrophoresis (PAGE) using $\alpha$-naphthyl acetate as a substrate. Two colonies were examined using 14,000×g supernatants from homogenized tissues of the foregut/salivary gland (FG), midgut (MG), hindgut (HG), and headless carcass that remained after gut removal (carcass).

Distribution of naphthyl acetate esterase activity: Native PAGE was used in combination with hydrolysis of the model esterase substrate α-naphthyl acetate, as shown in FIG. 3. Although a significant proportion of total esterase activity is located in the termite carcass, a diverse number of esterase isoforms and activity are also present in different gut regions. Within gut tissues, naphthyl acetate staining was strongest in the midgut, followed by the foregut/salivary gland, and the hindgut regions. Minor differences in banding patterns occurred between the two termite colonies that were investigated. However, results were consistent across the two colonies. Colony differences were most evident in the foregut/ salivary gland, the hindgut, and carcass, and may be the result of genetic variation between the two colonies.

Example 7

Figure 4:
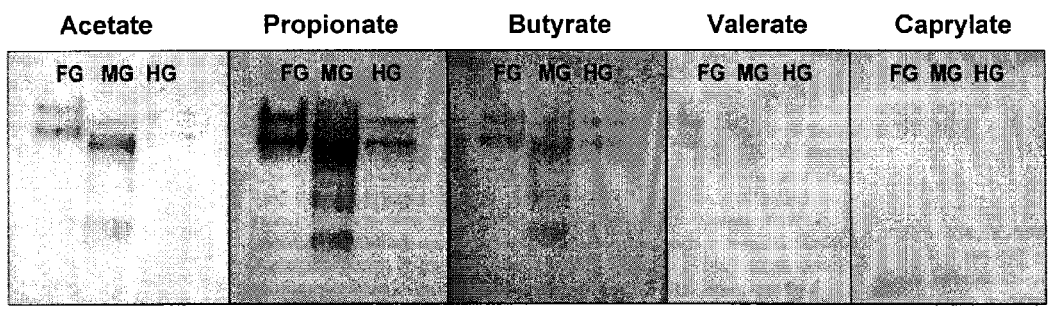
FIG. 4 illustrates the analysis of R. flavipes worker gut esterases by native PAGE.

Gut esterase activity toward naphthyl esters with varying carbon chain lengths: Activities toward different naphthyl ester substrates were investigated in different regions of the termite gut using native PAGE, as above, the results being shown in FIGS. 4 and 5. Gut esterases are most active toward substrates with side-chains of 3 (α-naphthyl propionate) and 4 (α-naphthyl butyrate) carbons, as well as the 2-carbon substrate α-naphthyl acetate. This result was consistent for all three termite gut tissues, with the exception of the foregut/salivary gland, which did not show strong differences between butyrate (C4) and valerate (C5) substrates (as shown in FIG. 40).

Figure 5:
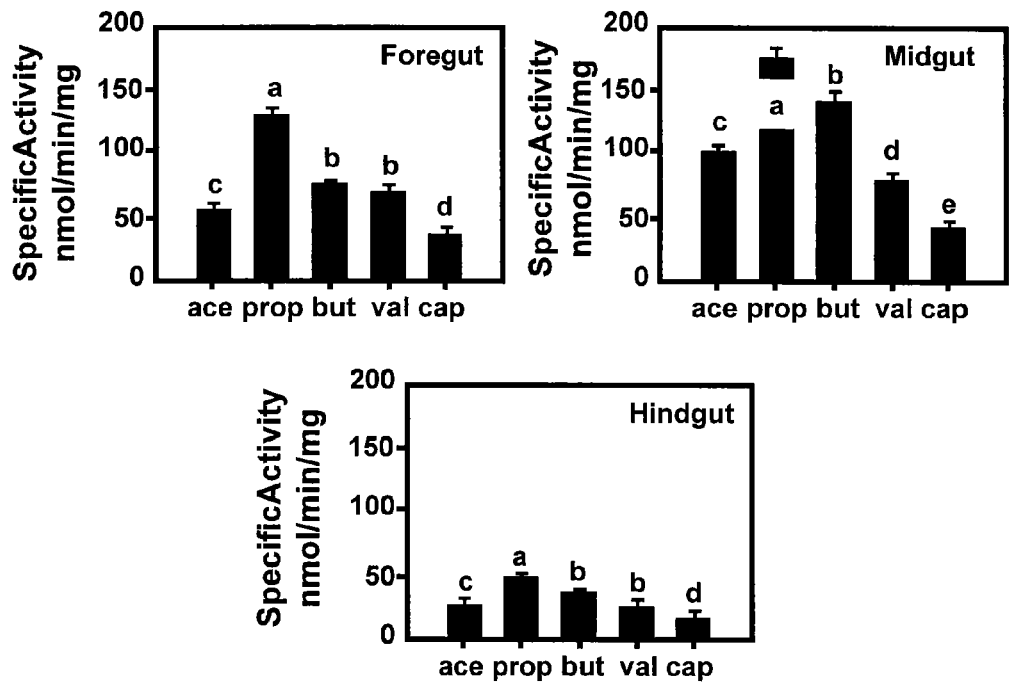
FIG. 5 shows a series of graphs illustrating the results of colorimetric microplate assays using various $\alpha$-naphthyl ester substrates. 14,000×g supernatants from homogenized tissues of the foregut/salivary gland (FG), midgut (MG), hindgut (HG) were examined. Substrates were naphthyl acetate (ace), propionate (prop), butyrate (but), valerate (val), and caprylate (cap). These substrates contain esteratic chain lengths of, respectively, 2, 3, 4, 5 and 6 carbon molecules. Bars within graphs with the same letter are not significantly different by LSD t-tests ($p<0.05$).
Figure 6:
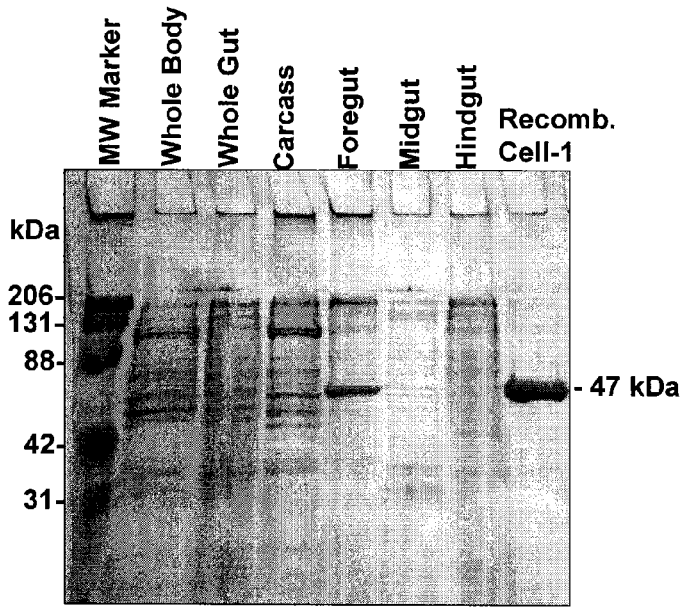
FIG. 6 is a digital image of a Coomassie-stained SDS PAGE gel showing the purified recombinant Cell-1 protein in relation to various endogenous protein fractions from R. flavipes termites.

For all three gut tissues, the lowest esterase staining activity occurred with α-naphthyl caprylate (C6). PAGE results were verified statistically using colorimetric microplate assays on the three gut regions, as shown in FIG. 5. Here, all three termite gut regions showed significantly greatest activity toward α-naphthyl propionate ($p<0.05$). Differences in activity between α-naphthyl butyrate and acetate were not as evident on native PAGE as in activity assays. Thus, the majority/greatest diversity of gut esterase activity in *R. flavipes* is located in the midgut, and that activity is greatest toward the 3-carbon ester naphthyl propionate. The results from using naphthyl propionate are similar to hemicellulose-degrading ferulic acid esterases that also show preferentially highest activity toward naphthyl propionate.

Example 8

Recombinant β-1,4-endoglucanase: protein expression: BEV system: The cDNA open-reading frame (GenBank Accession No.: AY572862; Zhou et al., (2007) *Gene* 395:29-39, SEQ ID NO.: 1 (encoding deduced amino acid sequence SEQ ID NO.: 2) was amplified without its signal sequence by PCR. Incorporated into the PCR amplicon were: (i) a heterologous signal sequence modeled after the *Bombyx mori* hormone bombyxin A-6 (GenBank Accession No.: 100169714 Bbx-a6), (ii) an XbaI restriction site, (iii) a C-terminal 6×His tag, and (iv) a NotI restriction site. These four features were incorporated into the amplicon via the primers: forward, 5'-CTAGTCTAGACTAGATGAAGATACTCCTTGCTATTG-CATTAATGTTGTCAACAGTAATGT GGGTGTCAA-CAGCTGCTTACGACTATAAG-3' (SEQ ID NO.: 45); reverse, 5'-TTTCCTTTTGCGGCCGCTTAGTGAT-GATGGTGATGATGCACGCCAGCCTTGAGGAG-3' (SEQ ID NO.: 46). The PCR amplicon was cloned into the XbaI-NotI sites of the pVL1393 transfer vector.

The resulting plasmid DNA was verified by sequencing and used for the co-transfection with linearized baculovirus DNA (BD Biosciences Pharmigen; San Diego, Calif.) into Sf9 cells. Cells were incubated at 27° C. for 4 days (Passage 0) and the supernatant was collected and used for virus amplification in fresh cell culture (Passage 1). The cell pellet from Passage 0 was tested by Western blotting with anti-His antibody to confirm expression of His-tagged protein. After 2 days, the recombinant virus from Passage 1 was harvested and injected to *T. ni* larvae as described previously (Liu et al., (2007) in: D. Murhammer (Ed.), Baculovirus and insect cell expression protocols, 2nd ed, Humana Press, Totowa, pp 267-280; Kovaleva et al., (2009) *Biotechnol Lett.* 31: 381-386). Larvae were orally infected with active pre-occluded baculovirus, harvested in large scale, and stored at –80° C. for later processing.

Recombinant protein was recovered from clarified *T. ni* homogenates by tandem Ni-IMAC (nickel-immobilized metal affinity chromatography) followed by buffer exchange with Sephadex G-25 chromatography. Protein storage buffer consisted of 0.1 M sodium acetate, 0.15M sodium chloride, 0.5M calcium chloride, and 0.5 mM copper sulfate (pH 5.8). Purity was assessed by SDS-PAGE with Coomassie staining and Western blotting with anti-His tag antibody.

Example 9

β-1,4-endoglucanase gel electrophoresis, deglycosylation assay, and Western blotting: For Coomassie-stained Native PAGE, volumes of supernatant containing 10 μg of total protein were diluted 1:1 with Native PAGE sample buffer (Bio-Rad) and loaded onto native PAGE gels prepared with 7.5% resolving gels and 4% stacking gels. Electrophoresis was conducted in a discontinuous Tris-Glycine running buffer for 1.5 hr at 4° C. Gels were stained as above. For CMC-native PAGE, gels were prepared and run as described above, except that carboxymethyl cellulose (CMC; Sigma) was incorporated into gels at 0.5%. After running, CMC gels were incubated in sodium acetate (0.05M, pH 5.0) and stained with Congo Red as described previously (Nakashima et al., (2002) *Cell Mol. Life. Sci.* 59: 1554-1560; Zhang et al., (2009) *Insect Biochem. Mol. Bio.* 39: 516-522).

An approximately 48 kDa band was present in baculovirus-infected larvae, but absent from uninfected and blank virus controls. Following purification and concentration the recombinant Cell-1 protein migrated as a single band at approximately 48 kDa. Preliminary stability tests conducted by incubating the protein at 65° C. or 26° C. for 65 hr revealed no protein degradation, indicating that it is stable in purified form. In addition to endoglucanase activity (the expected activity for Cell-1), exoglucanase and β-glucosidase activities were also investigated using the substrates pNPC and pNPG. All three activities were present in both uninfected and blank-virus-infected *T. ni* larvae, with exoglucanase and β-glucosidase activity being the strongest. However, only endoglucanase activity remained for purified Cell-1. In agreement with SDS-PAGE results, it was enriched at least 10-fold relative to clarified supernatants of infected larvae.

Analyses with and without the deglycosylation enzyme PNGase-F was negative (as shown in FIG. 5); they did not show changes in migration characteristics for the recombinant Cell-1 protein after PNGase-F treatment. Thus, the baculovirus/insect-expressed Cell-1 protein is properly assembled and retained the expected endoglucanase activity.

Example 10

Colorimetric β-1,4-endoglucanase enzyme assays: Six total substrates were tested: CMC (carboxymethyl cellulose), pNPG (p-nitrophenyl-beta-D-glucopyranoside), pNPC2 (p-nitrophenyl-beta-D-cellobioside), pNPC3 (p-nitrophenyl-beta-D-cellotrioside), pNPC4 (p-nitrophenyl-beta-D-cellotetraoside), and pNPC5 (p-nitrophenyl-beta-D-cellopentaoside). All assay methods were carried out under optimal conditions (Zhou et al., (2007) *Gene* 395:29-39).

Figure 7:
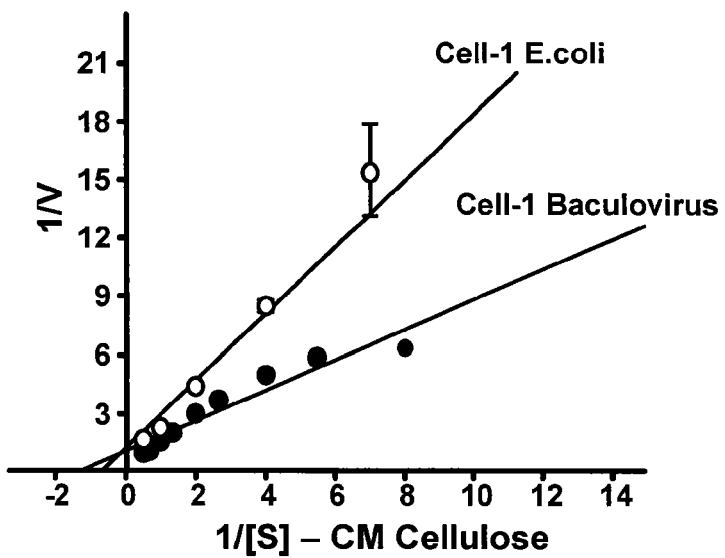
FIG. 7 is a graph illustrating Lineweaver-Burke kinetic plots comparing the relative activities of Cell-1 produced in a bacterial (E. coli) or a eukaryotic (insect) system.
Figure 8:
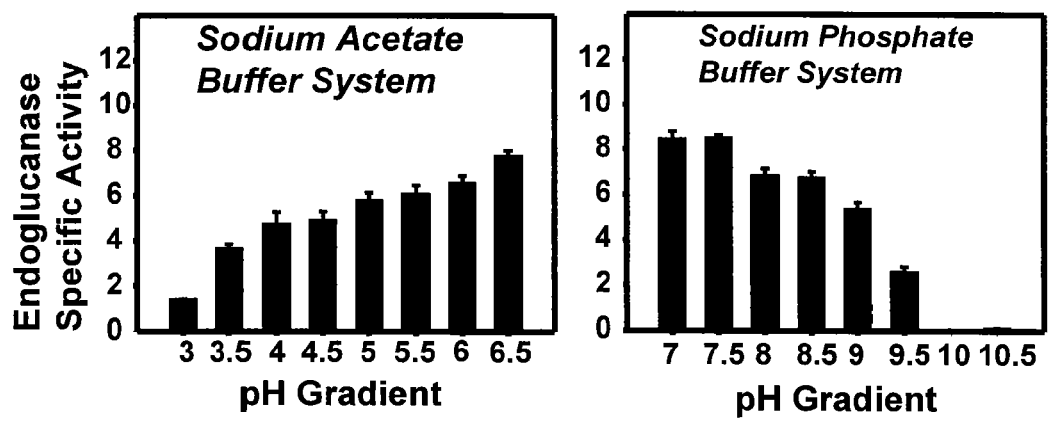
FIG. 8 shows a pair of graphs illustrating the determination of optimal pH for carboxymethyl cellulose digestion by the Cell-1 protein (optimal activity is about the known termite gut pH of approximately 7). Optimal pH and temperature stability for the purified BEVS-expressed Cell-1.
Figure 9A:
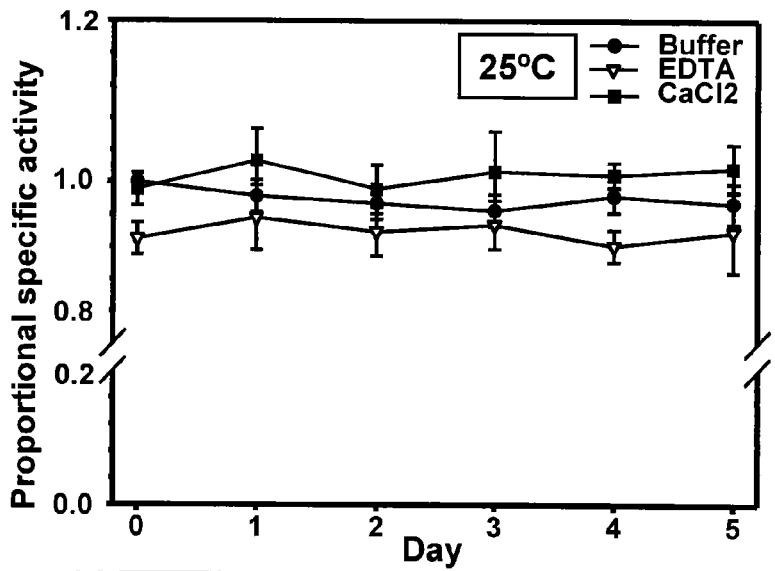
FIGS. 9A-9C show a series of graphs illustrating the impacts of EDTA and calcium chloride on temperature stability of the purified BEVS-expressed Cell-1.
Figure 9B:
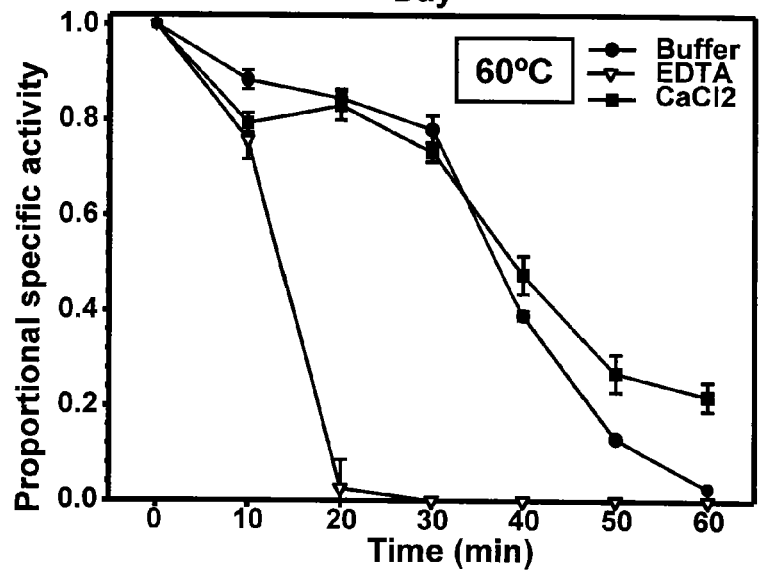
Figure 9C:
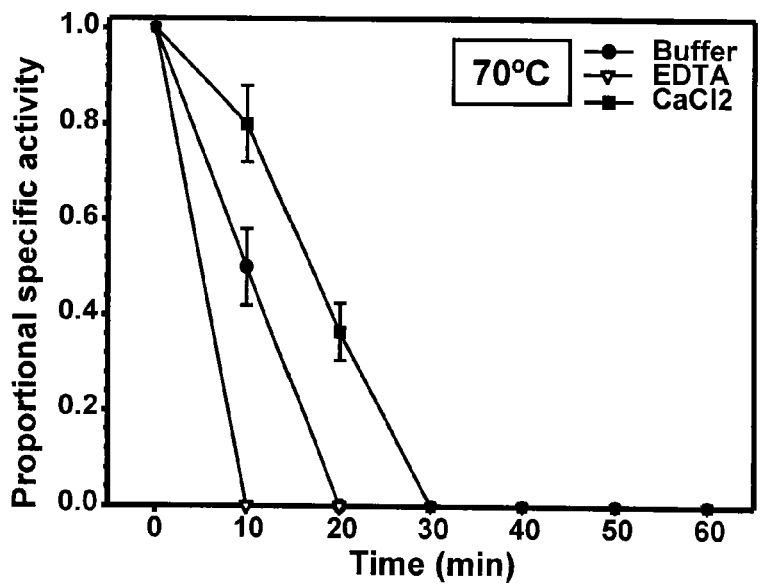

The kinetic constants $K_m$ and $V_{max}$ were determined in 100 mM sodium acetate buffer (pH 6.5) at 25° C. (FIG. 7). For subsequent characterizations, the 1.5% CMC concentration was used. pH studies were performed by dissolving 1.5% CMC in two different buffer systems: 100 mM sodium acetate (pH 3-6.5) and 100 mM sodium phosphate (pH 7-10.5), as shown in FIG. 8. Thermal stability tests were conducted using 1.5% CMC in 100 mM sodium phosphate at the optimal pH of 7. Temperature-cofactor studies were performed using 1.5% CMC dissolved in 100 mM sodium phosphate (pH 7) alone, plus 4 mM EDTA (final concentration), or plus 10 mM calcium chloride (final concentration). Pre-incubations took place for 0-5 days at 25° C. or 0-60 min at 60° C. or 70° C.; reactions were terminated by the combination of adding stop solution and boiling for 10 min, and then assays were read at 25° C. (FIG. 9). All reported activities are the average of 3-5 independent replicates.

Example 11

Production of Recombinant β-1,4-endoglucanase (Cell-1) in *E. coli*: *R. flavipes* Cell-1 was produced in *E. coli* to enable direct comparisons with the BEVS-expressed enzyme. Cell-1 was heterologously expressed with a heterologous signal peptide and C-terminal histidine tag in *E. coli* strain BL21 (DE3) pLysS, using the pET26 vector. IPTG induction of recombinant Cell-1 in *E. coli* at 37° C., 30° C., and 25° C. resulted in production of insoluble protein that readily precipitated after cell lysis and centrifugation. Recombinant Cell-1 was then partially solubilized with IPTG induction at 19° C.

Soluble fractions obtained after 19° C. IPTG induction were subjected to Ni-chromatography for purification. The His-tagged Cell-1 was retained on Ni columns and eluted in a single peak of CMC activity after the introduction of imidazole elution buffer. Active fractions also were assayed against the exoglucanase and β-glucosidase substrates pNPC and pNPG but showed no activity. After purification, pooling, and concentration the active Cell-1 fractions showed an enriched approximately 48 kDa protein band.

Figure 10:
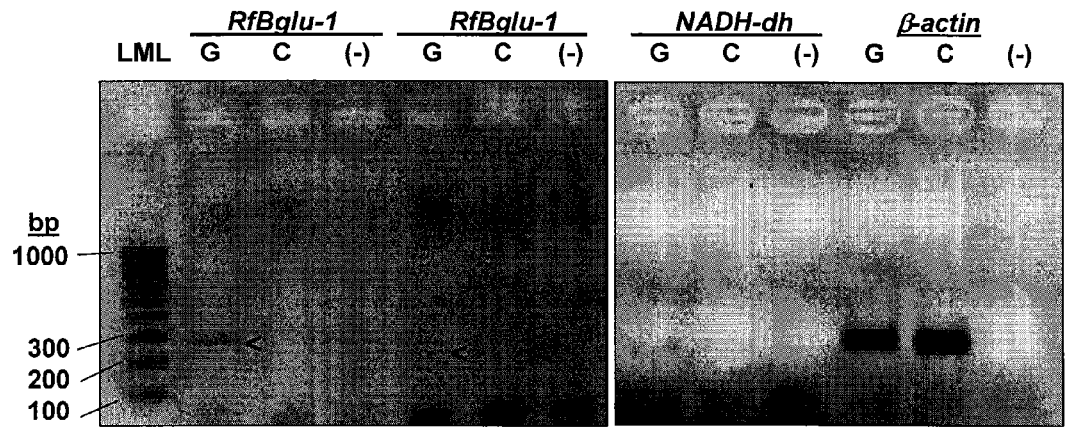
FIG. 10 shows a pair of digital images of agarose gels showing RfBGluc-1, RfBGluc-2, NADH-dehydrogenase, and $\beta$-actin relative transcript abundance after 35 cycles of conventional PCR amplification. G, whole gut; C, carcass; (-), negative control reaction conducted without template.

Example 12 pH and temperature stability of BEVS expressed β-1,4-endoglucanase Cell-1: Having thermostable enzymes for industrial lignocellulose processing is advantageous by enabling (i) greater activity with less enzyme, (ii) longer processing times due to higher stability, and (iii) increased flexibility for process configurations (Viikari et al., (2007) *Adv. Biochem. Eng. Biotechnol.* 108: 121-145). Maximal CMC activity was observed between pH 6.5 and 7.5 (FIG. 8). Temperature dependence of CMC activity in sodium phosphate buffer (pH 7) was maximal in the range of 50-60° C. but fairly constant across a wide temperature range (FIG. 10). There is, therefore, optimal activity toward the model substrate CMC around pH 7 and 50-60° C. BEVS-expressed recombinant Cell-1 shows slightly improved temperature stability at neutral pH relative to a number of other recombinant termite endoglucanases.

Example 13

Calcium as a cofactor in β-1,4-endoglucanase Cell-1 hydrolytic activity and temperature stability: The effects of calcium on recombinant Cell-1 activity were investigated using calcium chloride as a calcium source and EDTA as a potential calcium chelator. As determined from incubations conducted over a 5-day period at about 25° C. (FIG. 9), calcium chloride slightly enhanced CMC endoglucanase activity and EDTA was slightly inhibitory. With shorter incubations conducted at higher temperatures of 60° C. and 70° C., the same trends were apparent: calcium chloride stabilized/extended CMC hydrolysis activity over time, while EDTA rapidly reduced temperature stability (FIG. 9).

Example 14

β-glucosidase sequencing and sequence analyses: Original sequence tags were obtained by conventional Sanger sequencing from a host gut cDNA library as described in Tartar et al., ((2009) *Biotechnol. Biofuels* 2: 25). RfBGluc-1 was represented by eight library clones (GenBank Accession Nos. FL640173, FL639268, FL637619, FL637754, FL639498, FL636506, FL636125, FL635251) that aligned into a single contig ("Contig 771" having nucleotide sequence SEQ ID NO.: 5 comprising an ORF encoding the amino acid sequence SEQ ID NO.: 6). RfBGluc-2 was represented by one clone (GenBank Accession No. FL635576; having nucleotide sequence SEQ ID NO. 47).

The RfBGluc-1 cDNA nucleotide sequence SEQ ID NO.: 5 comprises 75 nucleotides of 5' untranslated region (UTR) ahead of the ATG start codon, a 1483 bp open reading frame (ORF), and a 3' UTR of 357 nucleotides after the "taa" termination codon. The 3' UTR contains a putative polyadenylation signal "aataa" and a terminal poly-A tail. The translated RfBGluc-1 amino acid sequence SEQ ID NO.: 6 comprises contains 495 amino acids and several identifiable motifs, including a 17-amino acid signal peptide MRLQTVCFV-IFVTAVFG (SEQ ID NO.: 48), indicating that the mature protein is soluble and secreted. Two motifs likely involved in substrate binding and catalysis are also present; "NEPL" with a GLU(E)$_{190}$ residue as a proton donor, and "TENG" with a GLU(E)$_{399}$ as a nucleophilic residue. Finally, two predicted N-glycosylation sites are $N_{259}$ and $N_{409}$.

The RfBGluc-2 partial cDNA sequence (GenBank Accession No.: FL635576 (SEQ ID NO.: 47)) is based on a single EST (Tartar et al., (2009) *Biotechnol. Biofuels* 2; 25)) composed of 496 nucleotides. It has no significant nucleotide identity with the full-length RfBGluc-1 cDNA; however, within a 165 amino acid residue overlap in the middle of their ORFs the translated RfBGluc-2 (SEQ ID NO.: 49) and RfBGluc-1 (SEQ ID NO.: 6) amino acid sequences share 53% identity. A proton donor component of the active site "TGNG" is included in the overlap region, as well as one N-glycosylation site (present in RfBGluc-1 but absent in RfBGluc-2).

Example 15

β-glucosidases-Quantitative PCR: RNA isolations were performed using the SV Total RNA kit (Promega; Madison, Wis.). Two replicate colonies were tested. RNA was isolated from whole gut, whole carcass (remaining body tissues after head and gut removal), and the four individual gut tissues foregut, salivary gland, midgut, and hindgut. cDNA was synthesized from total RNA using the iScript cDNA kit, which included a combination of oligo-dT and random hexamer primers (Bio-Rad; Hercules, Calif.). All PCR was performed in 20 µL volumes using SensiMix SYBR & Fluorescein one-step PCR reagent (Bioline; Taunton, Mass.), 1 µL cDNA template, and 0.5 µM primer concentrations. PCR primer sequences were as follows:

```
RfBGluc-1
                                    (SEQ ID NO.: 50)
("21C3 L" = TGCTTCTTCATGGCTCAGAGT;

(SEQ ID NO.: 51))
"21C3 R" = TGGTCTCCAGGTTGTGTATCC;

RfBGluc-2
                                    (SEQ ID NO.: 52)
("309K21 L" = GAGAGCTCCTCAACCAACGAT;

(SEQ ID NO.: 53))
"309K21 R" = CCTGTAACAAGCACCGGAGTA-3';

beta-actin
                                    (SEQ ID NO.: 42)
(Forward = AGAGGGAAATCGTGCGTGAC;

(SEQ ID NO.: 43))
Reverse = CAATAGTGATGACCTGGCCGT,
and

NADH-dh
                                    (SEQ ID NO.: 56)
(Forward = GCTGGGGGTGTTATTCATTCCTA;

(SEQ ID NO.: 57))
Reverse = GGCATACCACAAAGAGCAAAA.
```

Whole gut versus carcass comparisons were made by viewing reaction products after 35 cycles of amplification on 2% agarose gels. Relative expression within gut tissues was determined by quantitative real-time PCR (QRT-PCR), using NADH-dh as the reference gene. QRT-PCR data were analyzed by the $2^{-\Delta CT \Delta CT}$ method (Livak & Schmittgen (2001) *Methods* 25: 402-408), with normalization to the midgut. Statistical analysis of qRT-PCR data was performed by analyzing ΔCT data for all tissues. Mean separations were made using the Tukey HSD method (SAS software; Cary, N.C.).

Example 16

Recombinant β-glucosidase protein production and purification: Of three β-glucosidase-encoding cDNA clones, the entire RfBGluc-1 ORF was present in, and amplified from, clone TG_21_C3. Restriction sites and a C-terminal nucleotide sequence plus 6 histidine residues were introduced into the amplicon using the following primers: forward, 5'-GTC-GACATGAGGTTACAGACGGTTTGC-3' (SEQ ID NO.: 56); and reverse, 5'-CTGCAGTTAGTGATGATGGTGAT-GATGGTCTAGGAAGCGTTCTGGAA-3' (SEQ ID NO.: 57). This PCR amplicon, which encoded RfBGluc-1 ORF sequence (amino acids 1 to 495; SEQ ID NO.: 6)) and a hexahistamine tag at the C-terminus, was cloned into Sal1-Pst1 site of pFastBac1 transfer vector (Invitrogen; Carlsbad, Calif.).

Example 17

β-Glucosidaseenzyme Activity, Optimization, and Inhibition Assays

TABLE 3

Activity of recombinant RfBGluc-1 β-glucosidase towards natural substrates. Assays were read as endpoints at 505 nm using glucose detection reagent. Means ± standard errors are based on 3-5 independent replicates.

| Substrate | $r^2$* | $K_m$ [S] (mM) | $V_{max}$ (μmol/min/mg) | Activity (%)** |
|---|---|---|---|---|
| Cellobiose | 0.99 | 1.44 ± 0.14 | 638.0 ± 39.0 | 100 |
| Salicin | 0.99 | 34.30 ± 14.75 | 278.0 ± 11.00 | 44 |
| Laminaribose | 0.99 | 0.63 ± 0.02 | 218.1 ± 4.17 | 34 |
| Carboxymethyl cellulose | 0.99 | 52.58 ± 24.35 | 9.98 ± 4.70 | 2 |
| Microcrystalline cellulose | ND | ND | ND | 0 |
| Sucrose | ND | ND | ND | 0 |

*Correlation coefficients for Lineweaver-Burke plots;
**Percent activity rankings based on $V_{max}$;
ND, Activity not detectable.

All initial characterization assays took place in 0.1 M sodium acetate buffer (pH 6) using 2 μL of recombinant enzyme preparation (=1.58 μg protein per assay) in a total reaction volume of 250 μL. Synthetic p-nitrophenol substrates (Table 1) were tested in direct kinetic assays using a microplate reader. Reactions were initiated by adding 248 μL assay buffer to 2 μL protein. Assays were read at 420 nm every 20 sec for 5 min to yield mean velocity data in mOD/min. Specific activity was determined with the p-nitrophenol extinction coefficient of 0.6605 $mM^{-1}$ $cm^{-1}$. All results were averaged from three independent replicates, each conducted in triplicate.

TABLE 2

Activity of recombinant RfBGluc-1 β-glucosidase towards synthetic nitrophenol (NP) substrates. Assays were read kinetically at 420 nm. Means ± standard errors are based on 3-5 independent replicates.

| Substrate | Sugar Moiety/ Position | Linkage/ isomer | $r^2$* | $K_m$ [S] (mM) | $V_{max}$ (μmol/min/mg) | Activity (%)** |
|---|---|---|---|---|---|---|
| pNP-βD-Glucopyranoside | Glucose/p | β/D | 0.99 | 1.66 ± 0.07 | 22.92 ± 0.14 | 100 |
| pNP-βD-Cellotrioside | Cellotriose/p | β/D | 0.99 | 1.63 ± 0.50 | 22.56 ± 5.56 | 98 |
| pNP-βD-Cellotetraoside | Cellotetraose/p | β/D | 0.99 | 0.59 ± 0.01 | 16.64 ± 0.08 | 73 |
| pNP-βD-Cellobioside | Cellobiose/p | β/D | 0.99 | 1.56 ± 0.04 | 13.84 ± 0.35 | 60 |
| pNP-βD-Fucopyranoside | Fucose/p | β/D | 0.99 | 0.90 ± 0.07 | 12.56 ± 1.54 | 55 |
| oNP-βD-Xylopyranoside | Xylose/o | β/D | 0.99 | 7.57 ± 1.17 | 8.77 ± 1.35 | 38 |
| oNP-βD-Glucopyranoside | Glucose/o | β/D | 0.99 | 1.58 ± 0.19 | 4.20 ± 0.13 | 18 |
| mNP-αD-Galactopyranoside | Galactose/m | α/D | ND | ND | ND | 0 |
| pNP-αD-Galactopyranoside | Galactose/p | α/D | ND | ND | ND | 0 |
| pNP-βD-Galactopyranoside | Galactose/p | β/D | ND | ND | ND | 0 |
| pNP-βD-Xylopyranoside | Xylose/p | β/D | ND | ND | ND | 0 |
| pNP-βL-Arabinopyranoside | Arabinose/p | β/L | ND | ND | ND | 0 |
| pNP-βD-Glucuronide | glucuronic acid/p | β/D | ND | ND | ND | 0 |
| oNP-βD-Mannopyranoside | Mannose/o | β/D | ND | ND | ND | 0 |

*Correlation coefficients for Lineweaver-Burke plots;
**Percent activity rankings based on $V_{max}$;
ND, Activity not detectable.

Natural carbohydrate substrates (Table 2) were tested in endpoint assays in which color development was enabled using 439-90901 glucose-mutarose detection reagent (Wako Chemical; Richmond, Va.). Assays were conducted in 125 μL for 5 min at room temperature as described above and stopped with the addition of 125 μL glucose detection reagent. After 1 min, the absorbance was read at 505 nm.

Figure 11A:
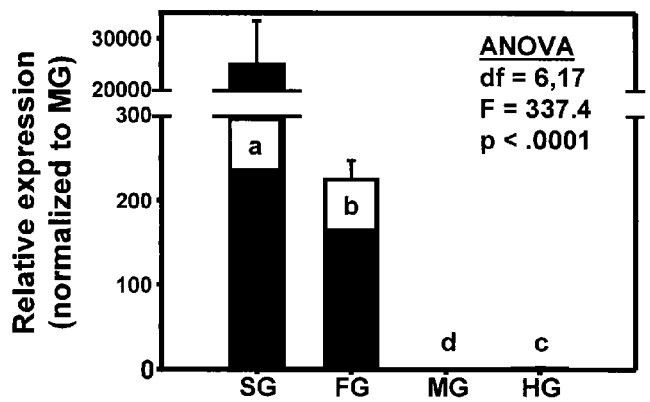
FIGS. 11A and 11B show graphs illustrating the relative expression of RfBGluc-1 (FIG. 11A) and RfBGluc-2 (FIG. 11B) by quantitative real-time PCR. Analyses were performed using the $2^{-\Delta\Delta CT}$ method. Results are normalized to NADH-dh as a reference gene and midgut as a reference tissue. Bars within graphs with different letters are significantly different by ANOVA and Tukey's HSD tests ($p<0.05$). Abbreviations: SG, salivary gland; FG, foregut; MG, midgut; HG, hindgut.
Figure 11B:
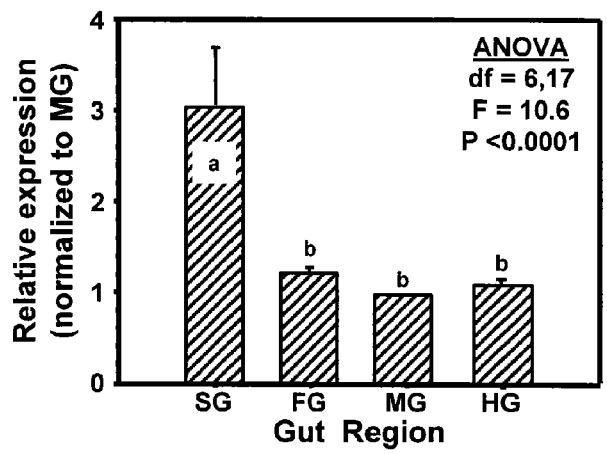

Example 19

β-glucosidase gene expression in gut and carcass: RfBGluc-1 and RfBGluc-2 gene expression was compared in worker whole gut and carcass tissues, and different gut regions (FIG. 10). First, using 35 cycles of convention PCR and agarose electrophoresis, RfBGluc-1 and RfBGluc-2 only showed detectable expression in gut tissue (FIG. 10). Next, qRT-PCR revealed highest RfBGluc-1 and RfBGluc-2 expression in salivary gland and foregut, followed distantly by hindgut and midgut (FIGS. 11A and 11B). RfBGluc-1 had the highest overall expression levels, with more than 25,000- and 225-fold higher expression in the salivary gland and foregut than midgut. RfBGluc-2 expression showed the same distribution through the gut, but at much lower levels; specifically, RfB-Gluc-2 was expressed at greater than 8,000-fold lower levels in the salivary gland than RfBGluc-1. Because salivary gland and foregut tissues are symbiont-free, these results indicate that RfBGluc-1 and RfBGluc-2 are host-derived genes.

Example 20

Figure 12A:
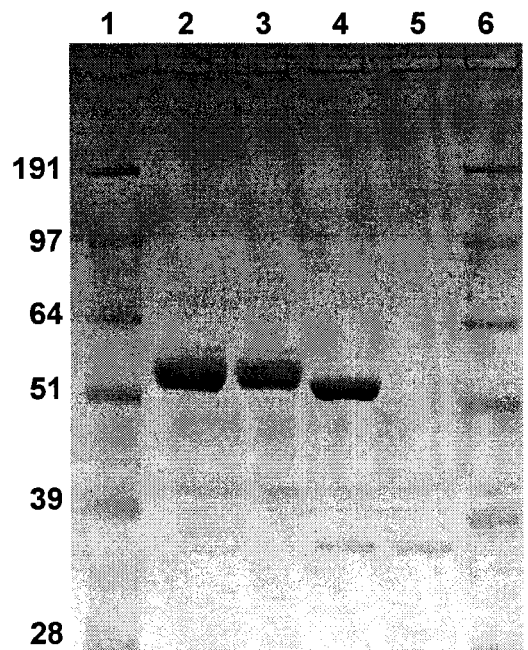
FIG. 12A is a digital image of an SDS PAGE analysis showing purified recombinant RfBGluc-1 protein with and without deglycosylation treatment by PNGase F. Lanes 1 and 6, MW markers in kilodaltons; lanes 2 and 3, purified RfBGluc-1; lane 4, PNGase-treated RfBGluc-1; and lane 5, PNGase control.
Figure 12B:
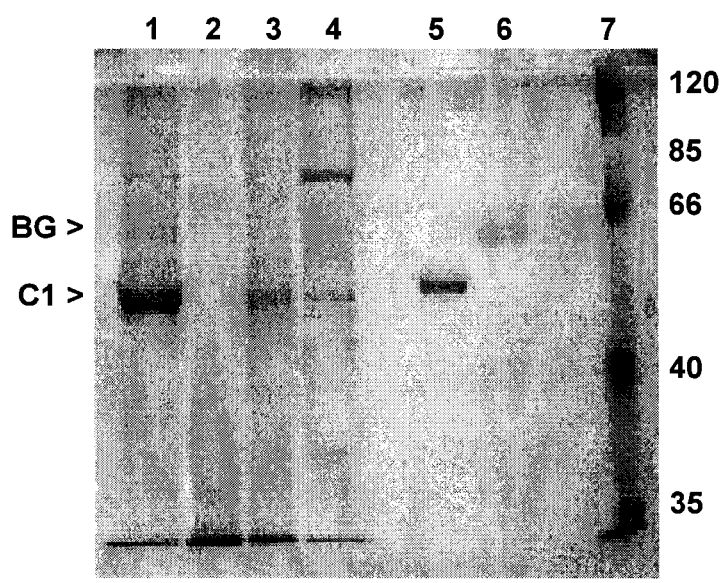
FIG. 12B is a digital image of a native PAGE analyses showing purified recombinant RfBGluc-1 protein shown in relation to native R. flavipes tissue preparations and recombinant RfCell-1. Lane 7, MW markers in kilodaltons; lane 1, foregut+salivary gland tissue; lane 2, midgut tissue; lane 3; hindgut tissue; lane 4, remaining carcass after gut removal; lane 5, recombinant RfCell-1 endoglucanase (shown for reference); lane 6, purified recombinant RfBGluc-1. Arrows labeled with BG and C1 indicate putative RfBGluc-1 and RfCell-1 proteins in the foregut+salivary gland preparations.

Recombinant RfBGluc-1 production, purification, and tissue-PAGE analyses: The RfBGluc-1 cDNA was functionally expressed with a C-terminal His-tag in *T. ni* larvae. The recombinant His-tagged protein was enriched to more than 98% purity from infected *T. ni* homogenates by filtration, Ni-IMAC, and Sephadex G-25 chromatography (FIG. 12A). The presence of His-tag on the purified protein was verified by western blotting with anti-His antibody and no cross-reactivity was observed in non-infected *T. ni* homogenates. Consistent with bioinformatic predictions presented above, treatment with the deglycosylation enzyme PNGase-F resulted in a single protein band and mobility shift on SDS-PAGE gels, verifying that recombinant RfBGluc-1 is glycosylated. The mass of the purified recombinant protein, with its two apparent glycosylations and a C-terminal histidine tag, was estimated at about 55-60 kDa by SDS-PAGE. Comparison of recombinant RfBGluc-1 against the recombinant cellulase (RfCell-1), as well as foregut/salivary gland, midgut, hindgut and carcass tissue preps suggests foregut/salivary gland expression for both RfCell-1 and RfBGluc-1 (FIG. 12B). Consistent with gene expression analyses, SDS-PAGE results did not show RfBGluc-1 expression in midgut, hindgut or carcass.

Example 21

Laccase cDNA sequencing: Sequencing efforts were guided initially by six contiguous laccase ESTs obtained from a normalized gut cDNA library (Scharf & Tartar (2008) *Biofuels Bioprod. Bioref.* 2: 540-552; Tartar et al., (2009) *Biotech. Biofuels* 2: 25, incorporated herein by reference in their entireties). This library was prepared from host gut tissues and has yielded more than 6,000 ESTs. Total RNA for RACE was isolated from 20 worker termite thoracic segments using the SV Total RNA Isolation Kit (Promega; Madison, Wis.). The SMART RACE cDNA Amplification Kit (Clontech; Valencia, Calif.) was used. RNA was DNase-treated and used as a template to produce 5' and 3' cDNA. RACE PCR amplifications were performed using 5' or 3' cDNA as a template. The anchor primer used in these reactions was the universal "primer A" mix paired with "Laccase5-R_336" reverse primer (5'-GCTTGCTGGTTGCGGGAATCCGTCGT-3' (SEQ ID NO.: 58)) or the "Laccase3-F_584" forward primer (5'-CGCCCCCATCTCCGCTCCTCTCACA-3' (SEQ ID NO.: 59)) for 5' and 3'-RACE reactions, respectively. These laccase primers were designed from the contiguous EST sequences noted above. The 5'-RACE product (approximately 1.3 kb) and the 3'-RACE reaction products (approximately 700 bp and 900 bp, respectively) were cloned into pCR8/GW/Topo. A second 5'-RACE reaction used the reverse primer 5'-ACTTCAGTTGGTGTTCACGGGAGG-3' (SEQ ID NO.: 60), which included the putative consensus stop codon. The reaction products, which included the entire laccase ORFs and their 5' untranslated regions, were cloned into pCR8/GW/Topo and clones Lac6, 7, 12, 13, 14, 15, 17, 19 and 20 were sequenced in both directions.

TABLE 4

Summary of laccase cDNA sequences
Nucleotide number or position

| RfLac No | Total length | Start (ATG) | Stop (TAG) | ORF length | Length (Amino acids) | Accession No | SEQ ID NO.: |
|---|---|---|---|---|---|---|---|
| 6 | 1985 | 39 | 1980 | 1941 | 647 | GQ421909 | 7 |
| 7 | 1987 | 41 | 1982 | 1941 | 647 | GQ421910 | 9 |
| 12 | 2035 | 89 | 2030 | 1941 | 647 | GQ421911 | 11 |
| 13 | 1584 | 16 | 1579 | 1563 | 521 | GQ421912 | 13 |
| 14 | 1988 | 42 | 1983 | 1941 | 647 | GQ421913 | 14 |
| 15 | 2038 | 91 | 2032 | 1941 | 647 | GQ421914 | 16 |
| 17 | 2038 | 92 | 2033 | 1941 | 647 | GQ421915 | 18 |
| 19 | 1986 | 40 | 1981 | 1941 | 647 | GQ421916 | 19 |
| 20 | 1963 | 19 | 412 | 393 | 131 | GQ421917 | 20 |

Seven of the nine clones encoded highly similar, full-length ORFs that had 22 variable nucleotide positions. All putative start codons were present at the first ATG following the 5' RACE PCR primer sequence. Additionally, the 5' end of the full length ORFs are translatable into identical signal peptides. Identifiable ORF amino acid sequences derived from the nucleotide sequences listed in Table 4 are according to SEQ ID NOs.: 8, 10, 12, 15, 17, 19, and 21, respectively.

Based on sequence alignments, three highly similar ORFs aligned well into one contig (Lac6, Lac7, and Lac19) (contig 1) and the remaining four into another (Lac12, Lac14, Lac15, and Lac17) (contig 2). Overall, the two contigs are 99.4% identical. Clones Lac6 (SEQ ID NO.: 7) and Lac12 (SEQ ID NO.: 11) were chosen as representative sequences for contigs (isoforms) 1 and 2, respectively (hereafter referred to as RfLacA and RfLacB).

Translations of RfLacA (SEQ ID NO.: 7) and RfLacB (SEQ ID NO.: 11) yielded the amino acid sequences SEQ ID NOs.: 8 and 12, respectively, which have 98.1% identity. A conserved signal peptide of 16 amino acids (MLPCVLLACAIGVASA (SEQ ID NO.: 61)) with a $Thr_{17}$ cleavage site was identified. All conserved amino acids implicated in copper ion binding are present in the RfLacA and RfLacB translation products. The fourth axial residue of the putative T1 copper center is a Met, which is present in RfLacA and RfLacB, and has been associated with laccases with lower redox potentials.

Example 22

Recombinant laccase production: Recombinant laccase proteins were produced in whole *T. ni* larvae using the PERLXpress procedure described in O'Connell et al. ((2007) *Mol. Biotechnol.* 36: 44-51) and Kovaleva et al. ((2009) *Biotechnol Lett.* 31: 381-386). The RfLacA (SEQ ID NO.: 7) and RfLacB (SEQ ID NO.: 11) clones were used as templates for PCR amplification and cloning. A C-terminal tag composed of two GLY and six HIS residues, as well as XbaI and EagI restriction sites, were incorporated into the amplicons utilizing the following primers: forward, 5'-TCTAGAATGTTGCCTTGCGTCCTGCTTG-3' (SEQ ID NO.: 62); reverse, 5'-CGGCCGTTAGTGATGATGGTGATGATGACCTCC-GTTG-GTGTTCACGGGAGGTGT-3' (SEQ ID NO.: 63). The PCR amplicons, which encoded full-length RfLacA (SEQ ID NO.: 8) and RfLacB (SEQ ID NO.: 12) (amino acids 1 to 647), plus the C-terminal Gly+His tag, were cloned into XbaI-EagI sites of the pVL1393 transfer vector, and recombinant baculoviruses were generated using a homologous recombination system in insect Sf9 cells.

The recombinant, His-tagged proteins were purified to greater than 90% purity from infected *T. ni* homogenates by filtration, Ni-IMAC, and Sephadex G-25 chromatography. The approximately 80 kDa recombinant proteins migrate as doublets on SDS-PAGE. Predicted sizes of the mature laccase peptides and histidine tags, respectively, are about 69.5 kDa and about 1 kDa.

Example 23

Lignin metabolism assays: Lignin alkali, a water soluble by-product of lignocellulose processing (Hernandez et al., (2001) *J. Chromat. A* 919: 389-394) was used as a model substrate dissolved at 1% w/v in sodium phosphate buffer (0.1M, pH 7.5). Reactions (176 μl volumes) contained: 150 μl buffer+substrate, 3 μl $H_2O_2$, 3 μl sodium azide, and 20 μl recombinant RfLacA. Control reactions contained all components except RfLacA. Reactions proceeded for 16 hr at 32° C. with shaking in unsealed 5 mL borosilicate tubes. Reactions were stopped with 1 mL acetic acid, followed by extraction with 5×–1 mL ethyl acetate (Humphreys et al., (1999) *Proc. Natl. Acad. Sci. USA* 96: 10045-10050). After mixing and partitioning by centrifugation, ethyl acetate extracts were pooled in fresh amber vials and stored at –20° C.

For HPLC analysis, samples and controls were dried to completeness under $N_2$, reconstituted in 150 μL methanol, and transferred to fresh ½-dram autosampler vials. HPLC was conducted on an Agilent system with two 100×4.6 mm Onyx Monolithic $C_{18}$ columns connected in parallel (Phenomenex; Torrance, Calif.). Solvent systems were: (A) 1% acetic acid in water, and (B) 1% acetic acid in acetonitrile. Samples were injected in 50 μL volumes and separated at flow rates of 0.8 mL/min with gradients of A:B (min): 95:5 (0-6.5) to 0:100 (25.5-35) to 95: 5 (45-50).

Example 24

Laccase

Quantitative Real-Time PCR

Four gut regions (salivary gland, foregut, midgut and hindgut) were dissected from workers of three *R. flavipes* colonies (n=25 workers) and placed directly into RNA lysis buffer (Promega). Total RNA was extracted using the SV Total RNA Isolation System Kit (Promega), according to instructions. Equal quantities of RNA (250 ng) were used as templates for cDNA synthesis using the iScript cDNA Synthesis kit (Bio-Rad). qRT-PCR reactions were conducted as described previously (Zhou et al., (2007) *Gene* 395: 29-39) using 1 μL cDNA template and 10 μL SensiMixPlus SYBR and Fluorescein PCR mix (Quantace; Taunton, Mass.). Laccase forward and reverse primers (1 μL each of 5 μM), respectively, were "RFLacc-exp-F1__52663" 5'-AATCAAACTGGGT-GCTTTGG-3' (SEQ ID NO.: 64) and "RfLacc-exp-R1__52664" 5'-AACTTGATGATCGCGTAGCC-3' (SEQ ID NO.: 65). These primers targeted conserved regions of all seven full-length sequence variants identified in the current work at consensus sequence positions 1536-1778. The reference gene, NADH-dh (Zhou et al., (2007) *Gene* 395: 29-39), was amplified with the forward and reverse primers "NADH-dhF__46415" (SEQ ID NO.: 54) and "NADHdhR__46416" (SEQ ID NO.: 55), respectively. PCR products were analyzed on 2% agarose gels. Relative expression levels were determined using the $2^{-\Delta\Delta CT}$ method (Livak & Schmittgen (2001) *Methods* 25, 402-408, incorporated herein by reference in its entirety) from three independent replicates, each conducted in triplicate. Expression data in the form of critical threshold (CT) values were statistically analyzed by ANOVA and post-hoc LSD t-tests (SAS software; Cary, N.C.).

Example 25

Recombinant Laccase RfLacA and RfLacB: optimal pH and substrate specificity determinations: Using 1 mM substrate concentrations, recombinant RfLacA and RfLacB were able to oxidize the following substrates in order of decreasing relative activity: hydroquinone, sinapinic acid, pyrocatechol, 2,6-DMP, pyrogallol, NADA, L-DOPA, and NBAD, as shown in Table 5 below.

TABLE 5

RfLacA substrate specificities at 1 mM substrate concentrations, and the kinetic parameters $V_{max}$ and $K_m$ for hydroquinone, 2,6-DMP, and pyrogallol.

| Substrate | Optimal pH | Specific Activity at 1 mM [S] nmol min$^{-1}$ mg$^{-1}$ | SEM | Relative Activity (%) | Apparent Km and Vmax $K_m^1$ (mM) | SEM | $V_{max}^2$ (μm min$^{-1}$) | SEM |
|---|---|---|---|---|---|---|---|---|
| Hydroquinone | 7 | 8.373 | 0.019 | 100.00 | 2.306 | 0.118 | 0.824 | 0.065 |
| Sinapinic Acid | 7.5 | 3.383 | 0.197 | 40.40 | 5.022 | 0.879 | 0.247 | 0.012 |
| Pyrocatechol | 7.5 | 2.315 | 0.160 | 27.65 | 17.527 | 1.457 | 15.434 | 1.175 |
| 2,6-DMP | 7.5 | 2.146 | 0.027 | 25.63 | 34.888 | 3.870 | 0.260 | 0.020 |
| Pyrogallol | 7 | 1.482 | 0.072 | 17.70 | | | | |
| NADA | 7.5* | 0.760 | 0.036 | 9.08 | | | | |
| L-DOPA | 6.0, 7.5 | 0.676 | 0.016 | 8.07 | | | | |
| NBAD | 7.5* | 0.190 | 0.024 | 2.27 | | | | |
| Guaiacol | ND | N/A | N/A | N/A | | | | |
| Caffeic Acid | ND | N/A | N/A | N/A | | | | |
| Ferulic Acid | ND | N/A | N/A | N/A | | | | |
| Syringaldazine | ND | N/A | N/A | N/A | | | | |
| ABTS | ND | N/A | N/A | N/A | | | | |

*Optimal pH not determined;
ND Activity not detected;
N/A Not applicable due to lack of detectable activity;
[1] Substrate concentrations [S] in mM providing ½ maximal activity;
[2] Maximal specific activities in nmol/min/mg.

Specific activity against the melanin precursors L-DOPA, NADA, NBAD, and L-tyrosine relative to that of 2,6-DMP was low (2.27-9.08%). Assays using the recombinant RfLacB isoform provided statistically indistinguishable results to RfLacA against all substrates.

Example 26

Recombinant Laccase Lac6 inhibition and enhancement: RfLac6 inhibition assays were conducted using 1 mM 2,6-DMP as a substrate in B&R buffer at pH 7.5. Enzyme and inhibitors were pre-incubated 5 min at room temperature on an orbital shaker before adding substrate. The inhibitors and concentrations used were: ethylenediaminetetraacetate (EDTA, 0.01-5 mM), sodium azide (NaN$_3$, 0.01-1000 mM), sodium cyanide (NaCN, 0.05-10 mM), and thioglycolic acid (TGA, 0.01-60 mM) (FIG. 13A-13D).

Figure 13A:
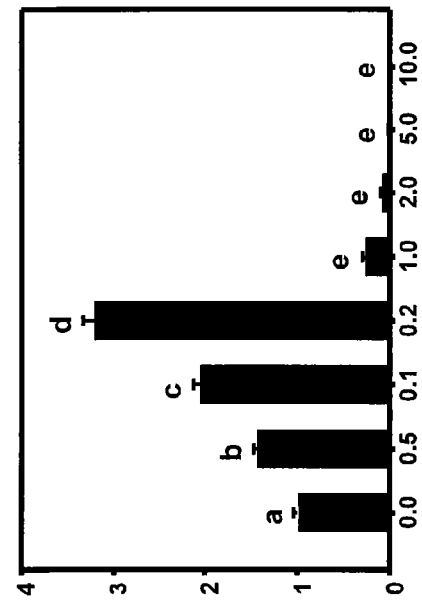
FIGS. 13A-13D illustrates the concentration-dependent effects of chemicals that either inhibit or enhance RfLacA oxidation of 2,6-dimethoxyphenol.
Figure 13B:
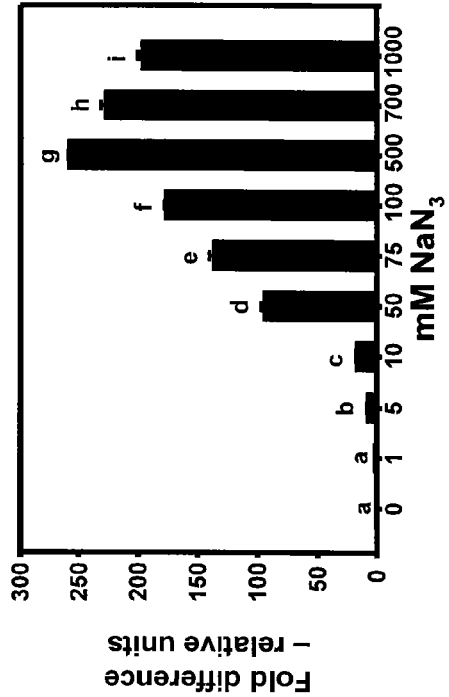
Figure 13C:
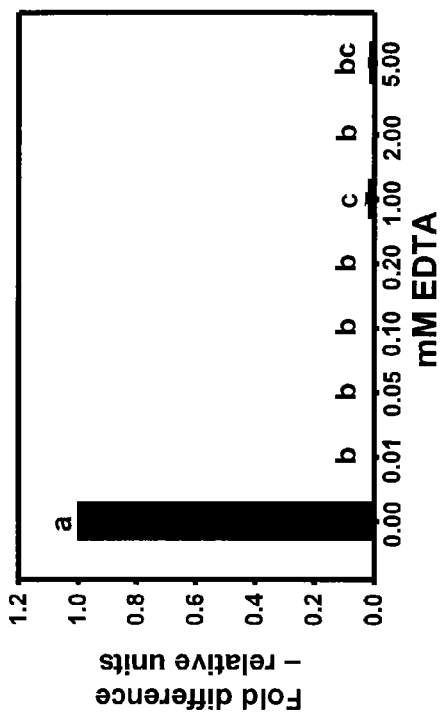
Figure 13D:
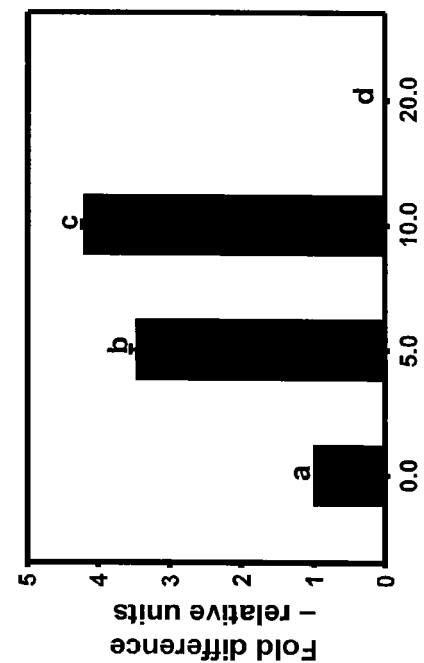

EDTA completely inhibited RfLac6 activity at concentrations as low as 0.01 mM (FIG. 13A). NaCN and TGA enhanced activity up to 0.2 and 10 mM, respectively, but became inhibitory above these concentrations (FIGS. 13B and 13C). NaN$_3$ significantly enhanced RfLac6 activity against DMP (FIG. 13D), catechol, pyrogallol, and hydroquinone. No activity was observed with NaN$_3$ and RfLac6, or NaN$_3$ and substrate alone. Finally, the enhancers did not enable the enzyme to oxidize ABTS or syringaldazine, both of which are not acted upon by RfLacA alone.

Example 27

Figure 14:
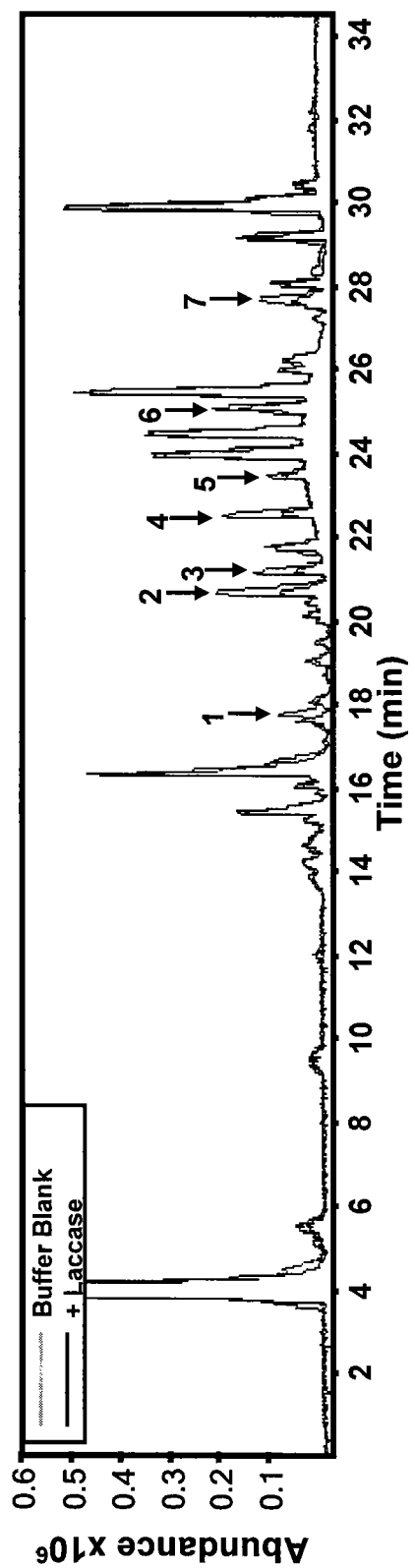
FIG. 14 is a graph illustrating an HPLC analysis of lignin alkali degradation by RfLacA. Two superimposed HPLC chromatograms are shown; the gray and black traces represent lignin alkali incubated without and with enzyme, respectively. Arrows and numbers indicate peaks with differential abundance between treatments. Peaks 1, 3, 4, 5 and 6 represent potential parent compounds acted upon by laccase action. Peaks 2 and 7 represent potential degradation products.
Figure 15:
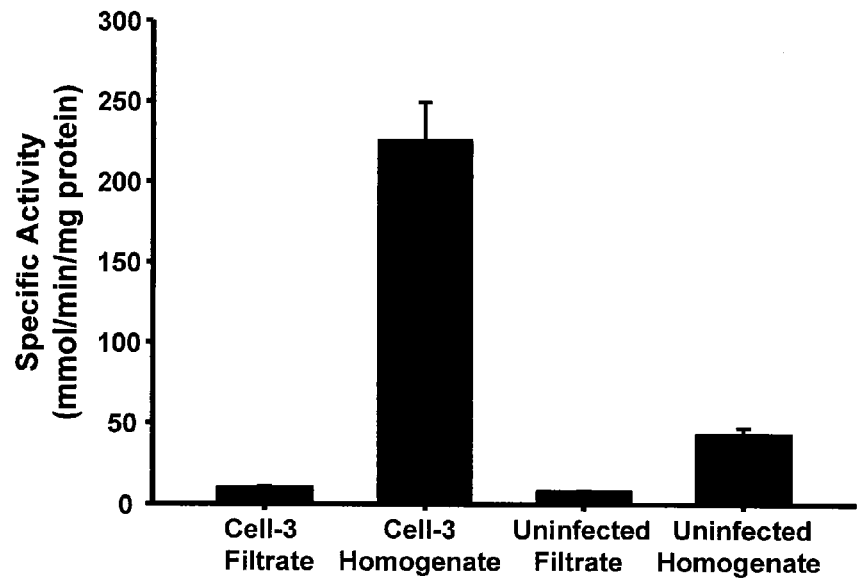
FIG. 15 is a graph illustrating that homogenates of recombinant Cell-3 infected larvae show higher exoglucanase (cellulase) activity than do uninfected homogenates when p-nitrophenyl cellobioside is used as a substrate. The reduced activity in filtrates suggests reduced stability of the mature protein through the enrichment process.

Laccase-Lignin alkali metabolism: Representative HPLC chromatograms from lignin alkali metabolism experiments are shown in FIG. 14. The chromatograms from control (buffer blank) and RfLacA incubations are superimposed to reveal peaks with differential abundance between treatments. Seven peaks showed differential abundance between control and laccase incubations. Peaks 1, 3, 4, 5 and 6 were higher in control incubations than laccase incubations, showing they contain lignin components degraded by laccase action. Conversely, peaks 2 and 7 are higher in laccase than control incubations, therefore containing degradation products. These results provide evidence of RfLacA action on lignin.

Example 32

Figure 16:
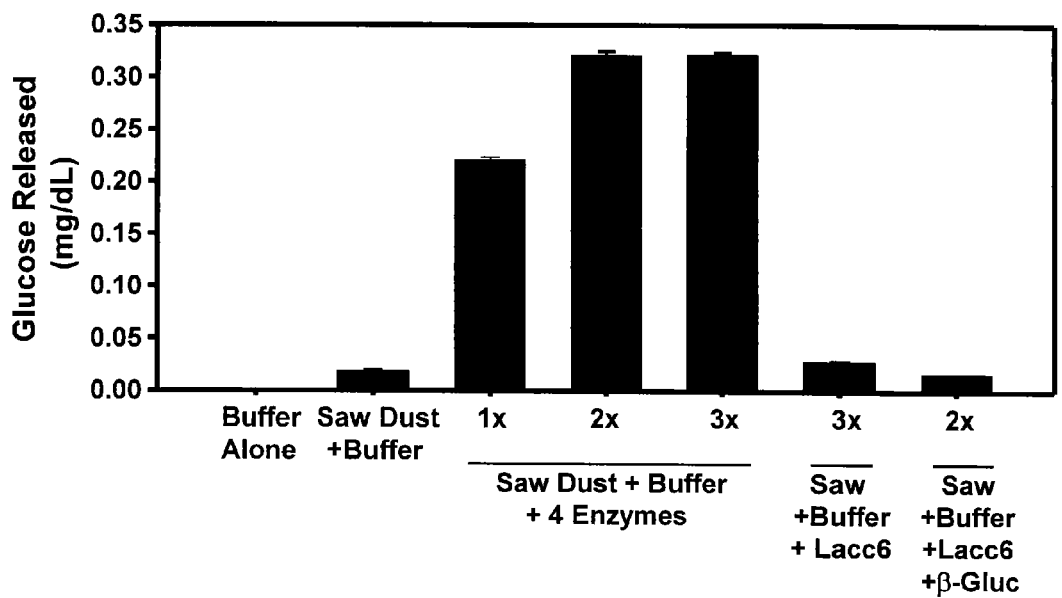
FIG. 16 is a graph illustrating measures of glucose release from saw-dust after incubation for 18 hrs at 37° C. with mixtures of recombinant lignocellulases. Enzymes were: Cell-1 endoglucanase, Cell-3 exoglucanase, Lacc6 laccase, and $\beta$-glucosidase. The mixture of four enzymes was required for quantifiable glucose release. 1×, 2× and 3×=1, 2 and 3 µL of enzyme stock.
Figure 17:
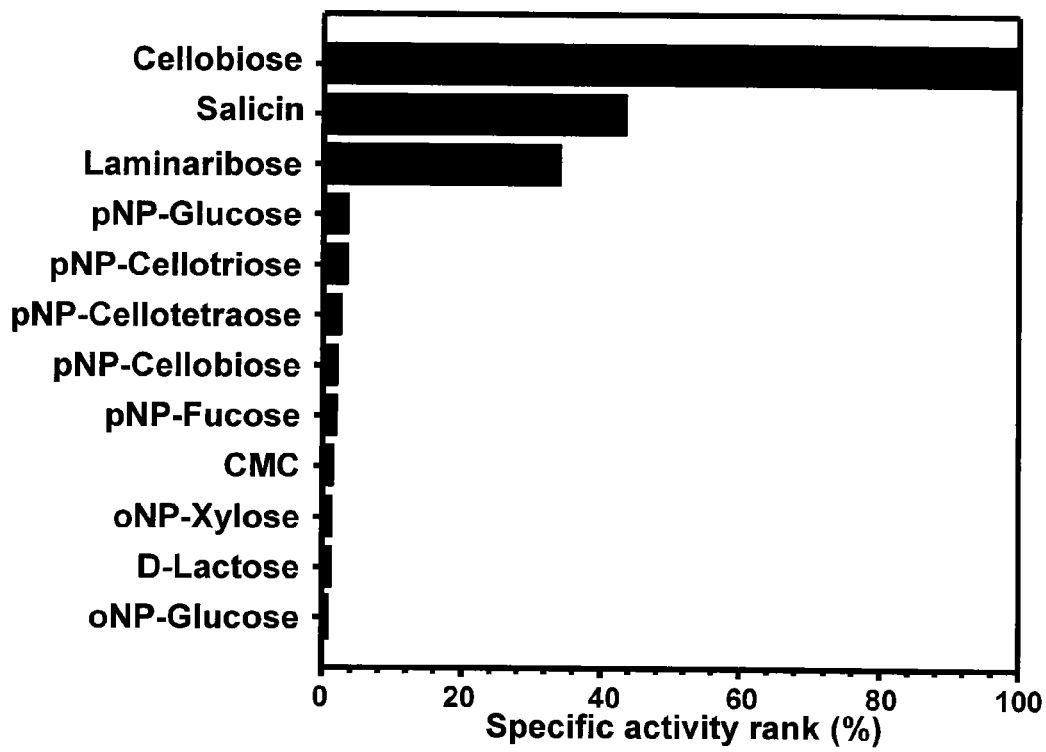
FIG. 17 shows a graph illustrating substrate specificity by recombinant RfBGluc-1 towards natural and synthetic substrates. See Tables 3 and 4 for substrate information.
Figure 18:
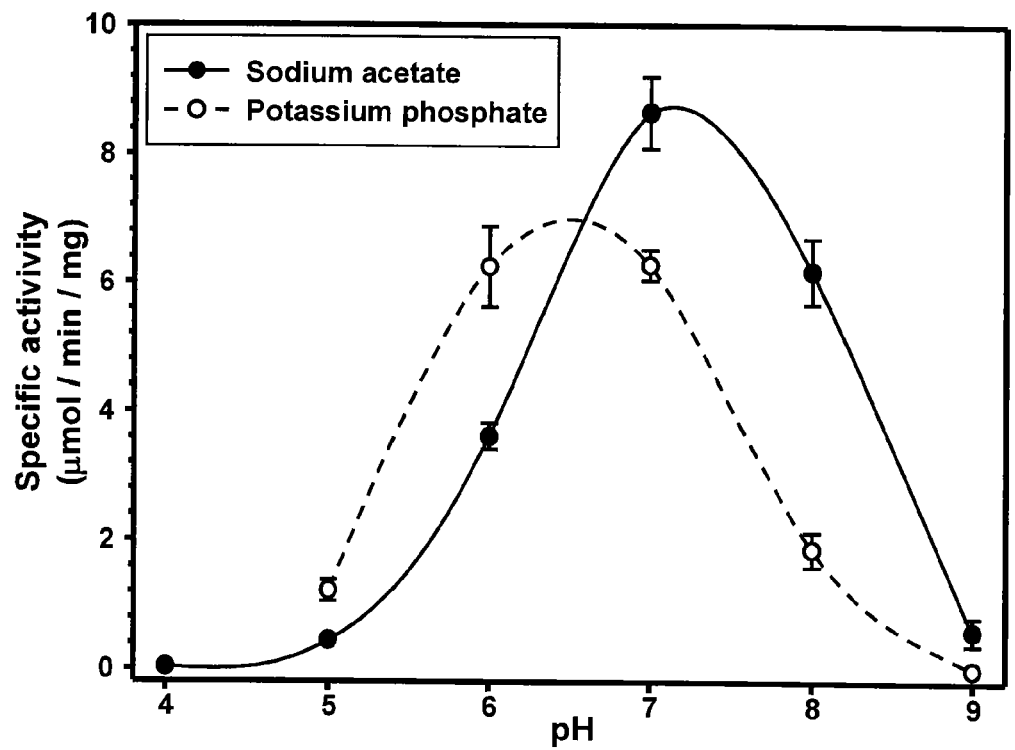
FIG. 18 shows a graph illustrating optimal pH determination for recombinant RfBGluc-1 using two buffer systems and 2 mM p-nitrophenyl-B-D-glucopyranoside as a substrate.
Figure 19:
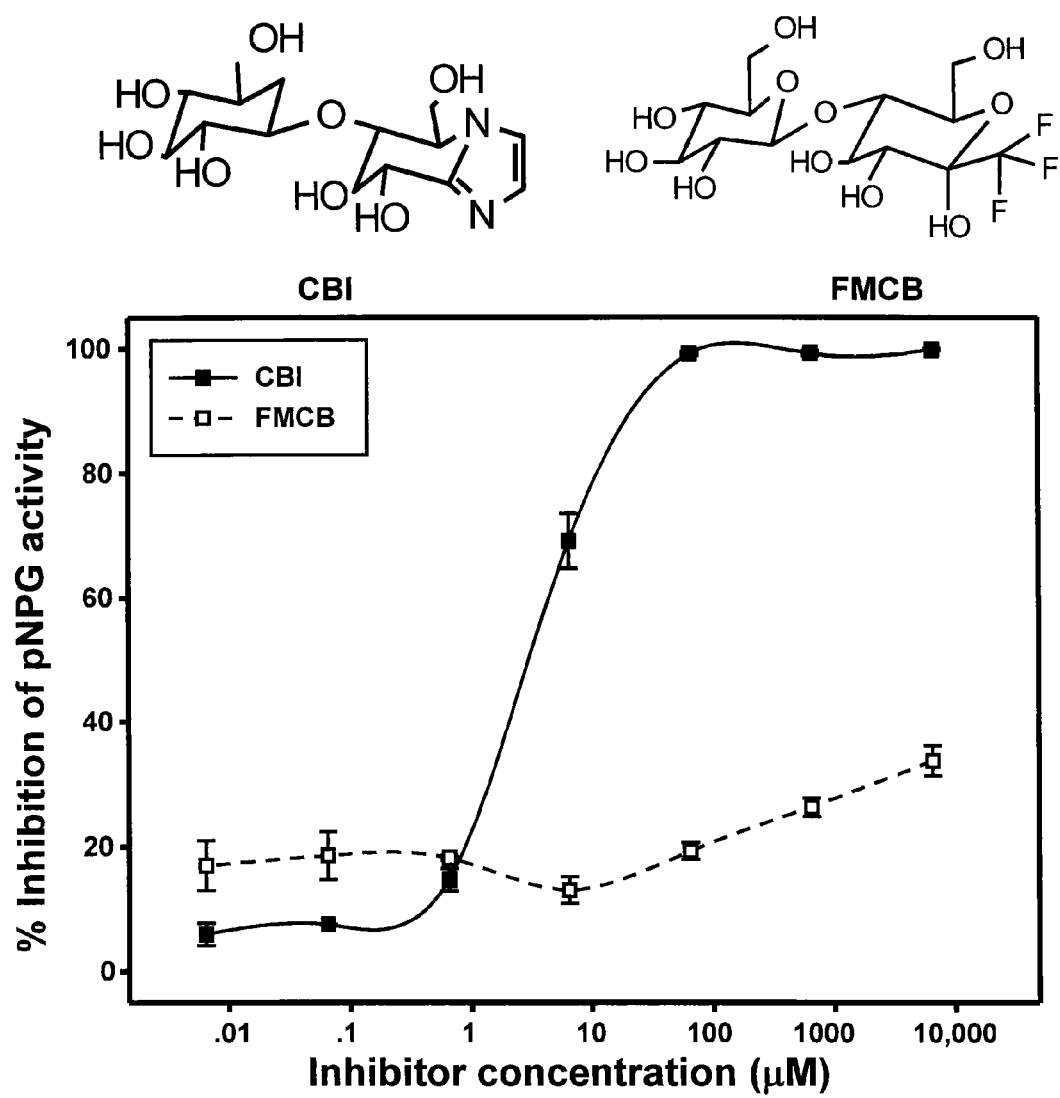
FIG. 19 shows a graph illustrating concentration-dependent inhibition of recombinant RfBGluc-1 by cellobioimidazole (CBI) and fluoromethyl cellobiose (FMCB). Assays were conducted at 25° C. in sodium acetate buffer (0.1M, pH 7) using 2 mM p-nitrophenyl-B-D-glucopyranoside as the substrate.

Recombinant Cell-3 characterization: The recombinant Cell-3 protein (nucleotide sequence SEQ ID NO.: 3; amino acid sequence SEQ ID NO.: 4) was investigated in unpurified form. As shown in FIG. 16, relative to uninfected control larvae not exposed to recombinant baculovirus, Cell-3 homogenates from infected larvae had significantly higher activity toward the model exoglucanase substrate p-nitrophenyl cellobioside (pNPC). However, pNPC activity in filtrates (=clarified supernatants) was significantly diminished, indicating that the recombinant Cell-3 protein has reduced stability. Other experiments investigating activity in crude homogenates over time and after repeated freeze-thaw cycles further verified reduced Cell-3 stability.

Example 33

Assay to Characterize Mixtures of Recombinant Enzymes Against a Woody-Feedstock Substrate All reactions were performed in 0.1 M sodium acetate buffer containing 10 mM calcium chloride (pH 7). The two feedstock substrates were pine sawdust (=lignin+cellulose+hemicellulose) and beechwood xylan (=lignin+hemicellulose). Feedstocks were tested at 2% w/v (10 mg in 0.5 mL buffer). Reactions were run for 18 hrs at 37° C. with shaking at 220 rpm in vented 1.5 mL plastic tubes.

Protein volumes used per assay were 10 μL of each of the Cell-1, β-glucosidase, and Laccase 6 recombinant protein preparations. These loading volumes provided 8.5, 7.9 and 2.0 μg of each protein, respectively, per reaction. The storage buffer for Cell-1 and β-glucosidase was 0.1 M sodium acetate, 0.15 M sodium chloride, and 0.5 M calcium chloride (pH 5.8). The storage buffer for Laccase 6 was 0.1M boric acid, phosphoric acid, and acetic acid (pH 7.0).

Reactions were stopped after 18 hours by the addition of 10 μL of 0.2 Methylene-diamine tetra-acetic acid and centrifuged for 5 min at 16,000×g. Glucose detection was performed in triplicate on 125 µL aliquots of each reaction supernatant. The entire experiment was replicated three times. Glucose release was measured using the Autokit Glucose reagent kit (Wako Chemical, Richmond, Va.) at a volume of 125 µL per determination. Glucose was quantified based on absorbance at 505 nm relative to glucose standard curves. Standard curves were prepared in eight serial dilutions downward from 0.6 mM in sodium acetate-calcium chloride reaction buffer.

Figure 20:
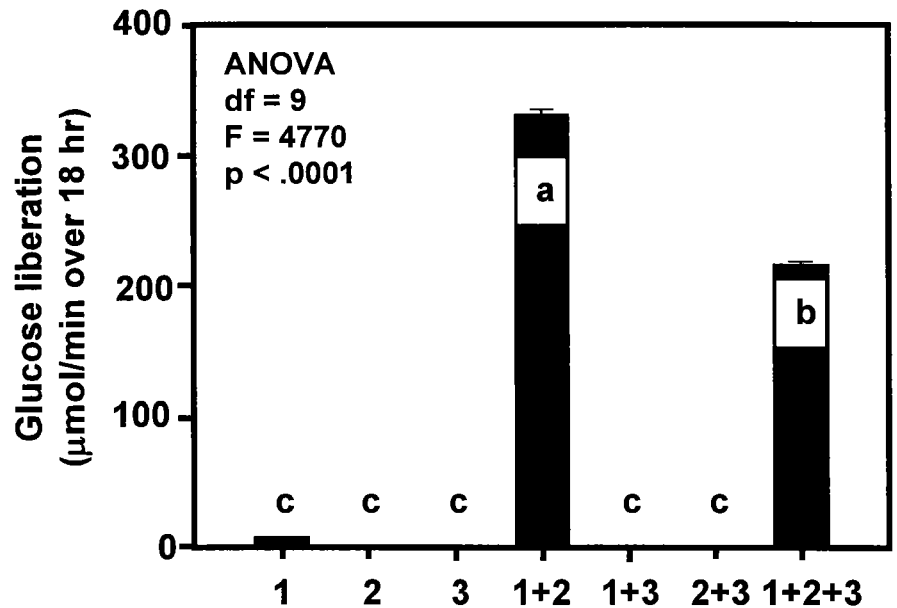
FIG. 20 is a graph illustrating the quantification of glucose release from pine sawdust. Treatments are shown across the x-axis are (1) Cell-1 endoglucanase, (2) the β-glucosidase, and (3) the Lac6 laccase, and their two—(1+2), (1+3), and (2+3) and three-way (1+2+3) combinations. Bars within graphs with the same letters are not significantly different by Tukey's HSD tests (p<0.05). Both ANOVA models were significant as well, with the parameters as shown.

FIG. 20 shows the results of assays using pine sawdust as a substrate, which is a complex lignocellulose substrate composed of approximately 20% lignin, approximately 40% cellulose and approximately 25% hemicellulose. No glucose release was detectable when the combinations of β-glucosidase and Laccase 6, Cell-1+Laccase 6 and p-glucosidase+Laccase 6 were used.

Cell-1 alone released a slight amount of glucose (3.70 pmol/min). Most notably, while the combination of Cell-1+β-glucosidase released 330.59 pmol glucose/min (greater that 300-fold synergy relative to either component alone), the three-enzyme combination showed synergy, but released significantly less glucose than the Cell-1+β-glucosidase combination. Without wishing to be bound by any one theory, this inhibitory effect by Laccase 6 may be due to laccase-mediated lignin degradation being detrimental to glucose release from cellulose. In the alternative, three-way combination may initially release large quantities of glucose that inhibit Cell-1 and β-glucosidase via a process known as "end-product inhibition" (Xiao et al., (2004) *Applied Biochem. Biotechnol.* 113: 1115-1126).

Figure 21:
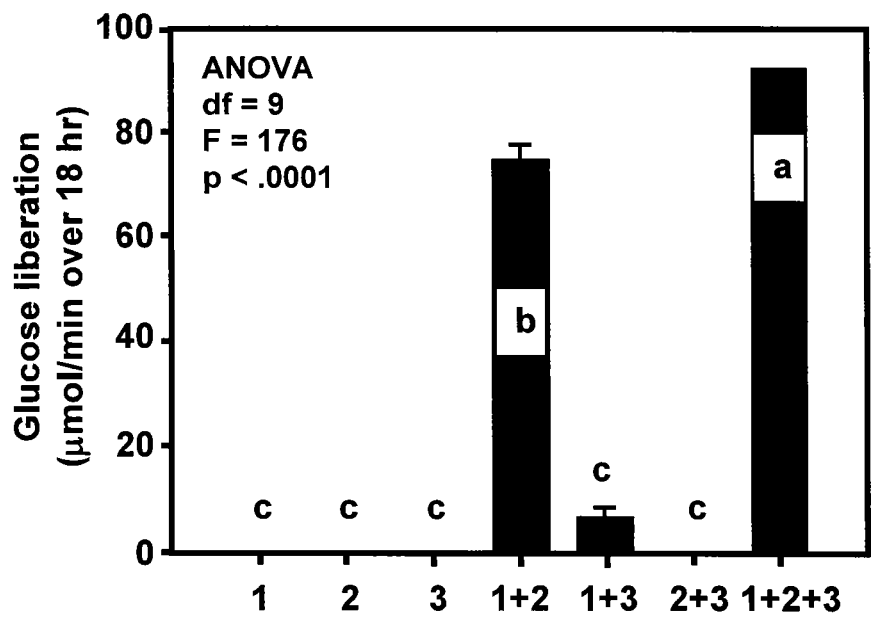
FIG. 21 is a graph illustrating the quantification of glucose release from beechwood xylan. Treatments are shown across the x-axis are (1) Cell-1 endoglucanase, (2) the β-glucosidase, and (3) the Lac6 laccase, and their two—(1+2), (1+3), and (2+3) and three-way (1+2+3) combinations. Bars within graphs with the same letters are not significantly different by Tukey's HSD tests (p<0.05). Both ANOVA models were significant as well, with the parameters as shown.

FIG. 21 shows the results of assays using beechwood xylan, a less complex substrate than pine sawdust, as a substrate. The beechwood xylan polymer contains a mix of β-1, 4-linked pentose and hexose sugars that are esterified with polymeric lignin and its monomeric subunits. Beechwood xylan is composed of less than 10% glucose; thus, significantly lower glucose is available for release relative to sawdust (note differences in Y-axis scales between FIGS. 20 and 21).

The beechwood xylan results are significant because none of three recombinant enzymes when tested alone were able to release glucose. Conversely, the two enzyme combination of Cell-1+β-glucosidase showed an approximately 80-fold synergy, indicating that they can act on hemicellulose as well as cellulose. The combination of Cell-1+Laccase 6 was also able to release low levels of glucose, which is suggestive of a role for laccase in hemicellulose delignification. Most notably, the three enzyme combination produced significantly greater glucose release than did the Cell-1+β-glucosidase combination and thereby provides evidence that the Lac 6 laccase can delignify hemicellulose, and also suggests that delignification is more important in release of fermentable sugars from hemicellulose than from cellulose.

What is claimed:

1. A method of converting a lignified plant material to a fermentable product, the method comprising the steps of:
   (a) obtaining a series of isolated polypeptides wherein said polypeptides are encoded by the genome of a termite, wherein the series of polypeptides cooperate to convert a plant lignocellulose to a fermentable product and wherein said series includes one or more polypeptides having at least 90% sequence identity to a polypeptide selected from the group consisting of (i) a laccase selected from the group the consisting of SEQ ID NOs: 8, 10, 12, 15, 17, 19, 21 and 23; (ii) an esterase selected from the group consisting of SEQ ID NO: 27, 29, 31 and 33 and (iii) a glucosidase comprising SEQ ID NO: 6, and wherein said series further comprises one or more polypeptides selected from the group consisting of an endoglucanase and an exoglucanase; and
   (b) incubating the series of polypeptides with a source of lignified plant material, under conditions allowing the polypeptides to cooperatively produce a fermentable product from the lignified plant material.

2. The method according to claim 1, wherein the isolated polypeptides are derived from the termite *Reticulitermes flavipes*, and not from a symbiont thereof, or a protozoa or a fungus.

3. The method according to claim 1, wherein the isolated polypeptides of the series of isolated polypeptides comprise an endoglucanase, a laccase, an esterase, and a glucosidase.

4. The method according to claim 3, wherein the series of the isolated polypeptides consists of an endoglucanase, an exoglucanase, a laccase, an esterase, and a glucosidase.

5. The method according to claim 1, wherein the isolated polypeptides of the series of isolated polypeptides are recombinant polypeptides, and wherein each polypeptide is expressed from an expression vector of a recombinant expression system, and wherein the recombinant expression system is selected from a eukaryotic cell-based system and a prokaryotic cell-based system.

6. The method according to claim 5, wherein the expression vector is a baculovirus expression vector and the recombinant expression system is a eukaryotic cell-based system.

7. The method according to claim 1, wherein the endoglucanase has an amino acid sequence having about 75% sequence identity with the amino acid sequence SEQ ID NO: 2.

8. The method according to claim 7, wherein the endoglucanase has the amino acid sequence SEQ ID NO: 2.

9. The method according to claim 1, wherein the series of isolated polypeptides further comprises an exoglucanase having an amino acid sequence having about 75% sequence identity with the amino acid sequence SEQ ID NO: 4.

10. The method according to claim 9, wherein the exoglucanase has the amino acid sequence SEQ ID NO: 4.

11. The method according to claim 1, wherein the laccase has the amino acid sequence selected from the group consisting of: SEQ ID NOs: 8, 10, 12, 15, 17, 19, 21, and 23.

12. The method according to claim 1, wherein the esterase has the amino acid sequence selected from the group consisting of: SEQ ID NOs: 27, 29, 31, and 33.

13. The method according to claim 3, wherein the glucosidase has the amino acid sequence SEQ ID NO: 6.

14. The method according to claim 1, wherein the fermentable product comprises at least one carbohydrate selected from the group consisting of: a glucose, a mannose, a xylose, a galactose, a rhamnose, an arabinose, a glucuronic acid, a mannuronic acid, and a galacturonic acid.

15. The method according to claim 14, wherein the fermentable product comprises glucose.

16. A system for producing a fermentable product from a lignified plant material, wherein the system comprises at least two isolated polypeptides selected from the group consisting of: an endoglucanase, an exoglucanase, a laccase having at least 90% sequence identity to a polypeptide selected from the group consisting of SEQ ID NOs: 8, 10, 12, 15, 17, 19, 21 and 23, an esterase having at least 90% sequence identity to a polypeptide selected from the group consisting of SEQ ID NO: 27, 29, 31 and 33, and a glucosidase having at least 90% sequence identity to a polypeptide of SEQ ID NO: 6, from of the termite *Reticulitermes flavipes* and wherein the at least two isolated polypeptides can cooperate to convert a constituent of the lignified plant material to a fermentable product or a precursor thereof, and wherein said system comprises at least one of said laccase, said esterase or said glucosidase.

17. The system according to claim 16, wherein the nucleotide sequence encoding the endoglucanase hybridizes under high stringency conditions to a nucleotide sequence according to SEQ ID NO: 1, the nucleotide sequence encoding the exoglucanase hybridizes under high stringency conditions to a nucleotide sequence according to SEQ ID NO: 3, the nucleic acid molecule encoding the laccase hybridizes under high stringency conditions to a nucleotide sequence selected from the group consisting of: SEQ ID NOS: 7, 9, 11, 13, 14, 16, 18, 20, and 22, the nucleic acid molecule encoding the esterase hybridizes under high stringency conditions to a nucleotide sequence selected from the group consisting of: SEQ ID NOS: 26, 28, 30, and 32, and the nucleotide sequence encoding the glucosidase hybridizes under high stringency conditions to SEQ ID NO:5, wherein said high stringency conditions are 50% formamide, 1 M NaCl, 1% SDS at 37° C. and a wash in 0.1×SSC at 60-65° C.

18. The system according to claim 16, wherein each of the isolated nucleic acid molecules thereof is operably inserted into an expression vector.

19. A recombinant cell comprising an isolated nucleic acid molecule hybridizing under high stringency conditions to a nucleotide sequence encoding a polypeptide selected from the group consisting of: an endoglucanase, an exoglucanase, a laccase having at least 90% sequence identity to a polypeptide selected from the group consisting of SEQ ID NOs: 8, 10, 12, 15, 17, 19, 21 and 23, an esterase having at least 90% sequence identity to a polypeptide selected from the group consisting of SEQ ID NO: 27, 29, 31 and 33, and a glucosidase having at least 90% sequence identity to a polypeptide of SEQ ID NO: 6 from of the termite *Reticulitermes flavipes*, wherein the nucleotide sequence encoding the endoglucanase is according to SEQ ID NO: 1, the nucleotide sequence encoding the exoglucanase is according to SEQ ID NOS: 3, wherein said recombinant cell comprises at least one nucleic acids encoding said laccase, said esterase or said glucosidase.

\* \* \* \* \*

UNITED STATES PATENT AND TRADEMARK OFFICE
CERTIFICATE OF CORRECTION

PATENT NO. : 8,445,240 B2  Page 1 of 1
APPLICATION NO. : 13/263107
DATED : May 21, 2013
INVENTOR(S) : Scharf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 30 days.

Signed and Sealed this
Eighth Day of September, 2015

Michelle K. Lee
*Director of the United States Patent and Trademark Office*

SEQUENCE LISTING

```
<160> NUMBER OF SEQ ID NOS: 65

<210> SEQ ID NO 1
<211> LENGTH: 1489
<212> TYPE: DNA
<213> ORGANISM: Reticulitermes flavipes
<220> FEATURE:
<221> NAME/KEY: misc_feature
<223> OTHER INFORMATION: cDNA sequence encoding Beta-1,4-endoglucanase
      (Cell-1)

<400> SEQUENCE: 1
ccactaccag ccgccatgaa ggtcttcgtt tgtcttctgt ctgcactggc gctttgccaa      60
gctgcttacg actataagac agtactaagc aattcgctac ttttctacga ggctcagcga     120
tcgggaaaat tgccgtctga tcagaaggtc acgtggagga aggattccgc ccttaacgac     180
aagggccaga agggcgagga cctgacagga ggatactatg acgctggtga ttttgtgaag     240
ttcggcttcc ctatggcgta cacagtcacc gtcctcgctt ggggtgttat agactacgaa     300
tcagcgtatt ctgcagcagg agctctggat agtggtcgca aggctcttaa atatggcacg     360
gactacttcc tcaaggcgca cacggccgcg aacgaattct acggacaagt gggccaggga     420
gatgtcgacc acgcctactg gggacgtcca gaagacatga cgatgtccag acctgcctac     480
aagatcgaca cgtcgaaacc agggtctgac ctggcagccg acagaccgc cgccctcgct     540 gcaactgcca tcgcctacaa gagtgctgac gcaacttatt ccaacaactt gatcacccac     600
gccaagcagc ttttcgactt cgccaacaat tatcgcggca aatacagtga ttcaatcacc     660
gacgcgaaga atttctacgc gtccggagac tacaaggacg agttagtatg ggcagccgca     720
tggctctaca gggcgaccaa cgacaacacc tatctgacta aagctgaatc gctatacaac     780
gaattcggcc tcggaaactg gaacggtgcc ttcaactggg ataacaagat ctccggtgta     840
caggttctac tggccaagct cacaagcaag caggcataca aggacaaggt acaaggctac     900
```

```
gtcgattact tgatttcgtc tcagaagaag acacccaagg gtctcgtata catcgaccag     960
tggggtaccc tgcgacatgc tgccaattct gctctcattg ctctgcaggc agccgacctg    1020
ggtatcaatg ctgctactta tcgcgcgtat gccaagaagc agatcgatta cgcattgggt    1080
gatggaggtc gcagctacgt cgtaggattt ggtactaacc cacccgtacg ccctcaccac    1140
agatccagct cgtgccctga cgcaccagcc gtatgtgact ggaacacgta caacagcgcc    1200
ggccccaatg cccacgtact caccggagcc ttggtgggtg gtccagatag caacgatagc    1260
tacacggacg ctcgcagcga ttacatctcc aacgaagtgg ccacagatta caacgctggc    1320
ttccaatcag ctgtcgctgg tctcctcaag gctggcgtgt aaccgcacac agcactcaat    1380
gtctccctgt ccactggaca tgtgtacaat ttgacaacga aatgtaata ttcttcagaa     1440 aagtgcaata aaagttcaca attcaacaca aaaaaaaaa aaaaaaaa                  1489
```

<210> SEQ ID NO 2
<211> LENGTH: 448
<212> TYPE: PRT
<213> ORGANISM: Reticulitermes flavipes
<220> FEATURE:
<221> NAME/KEY: MISC_FEATURE
<223> OTHER INFORMATION: amino acid sequence Beta-1,4-endoglucanase
      (Cell-1)

<400> SEQUENCE: 2

```
Met Lys Val Phe Val Cys Leu Leu Ser Ala Leu Ala Leu Cys Gln Ala
1               5                   10                  15

Ala Tyr Asp Tyr Lys Thr Val Leu Ser Asn Ser Leu Leu Phe Tyr Glu
            20                  25                  30

Ala Gln Arg Ser Gly Lys Leu Pro Ser Asp Gln Lys Val Thr Trp Arg
        35                  40                  45

Lys Asp Ser Ala Leu Asn Asp Lys Gly Gln Lys Gly Glu Asp Leu Thr
    50                  55                  60

Gly Gly Tyr Tyr Asp Ala Gly Asp Phe Val Lys Phe Gly Phe Pro Met
65                  70                  75                  80

Ala Tyr Thr Val Thr Val Leu Ala Trp Gly Val Ile Asp Tyr Glu Ser
                85                  90                  95

Ala Tyr Ser Ala Ala Gly Ala Leu Asp Ser Gly Arg Lys Ala Leu Lys
            100                 105                 110

Tyr Gly Thr Asp Tyr Phe Leu Lys Ala His Thr Ala Ala Asn Glu Phe
        115                 120                 125

Tyr Gly Gln Val Gly Gln Gly Asp Val Asp His Ala Tyr Trp Gly Arg
    130                 135                 140

Pro Glu Asp Met Thr Met Ser Arg Pro Ala Tyr Lys Ile Asp Thr Ser
145                 150                 155                 160

Lys Pro Gly Ser Asp Leu Ala Ala Glu Thr Ala Ala Ala Leu Ala Ala
                165                 170                 175

Thr Ala Ile Ala Tyr Lys Ser Ala Asp Ala Thr Tyr Ser Asn Asn Leu
            180                 185                 190

Ile Thr His Ala Lys Gln Leu Phe Asp Phe Ala Asn Asn Tyr Arg Gly
        195                 200                 205

Lys Tyr Ser Asp Ser Ile Thr Asp Ala Lys Asn Phe Tyr Ala Ser Gly
    210                 215                 220

Asp Tyr Lys Asp Glu Leu Val Trp Ala Ala Trp Leu Tyr Arg Ala
225                 230                 235                 240

Thr Asn Asp Asn Thr Tyr Leu Thr Lys Ala Glu Ser Leu Tyr Asn Glu
                245                 250                 255
```

```
Phe Gly Leu Gly Asn Trp Asn Gly Ala Phe Asn Trp Asp Asn Lys Ile
            260                 265                 270

Ser Gly Val Gln Val Leu Leu Ala Lys Leu Thr Ser Lys Gln Ala Tyr
        275                 280                 285

Lys Asp Lys Val Gln Gly Tyr Val Asp Tyr Leu Ile Ser Ser Gln Lys
    290                 295                 300

Lys Thr Pro Lys Gly Leu Val Tyr Ile Asp Gln Trp Gly Thr Leu Arg
305                 310                 315                 320

His Ala Ala Asn Ser Ala Leu Ile Ala Leu Gln Ala Ala Asp Leu Gly
                325                 330                 335

Ile Asn Ala Ala Thr Tyr Arg Ala Tyr Ala Lys Lys Gln Ile Asp Tyr
            340                 345                 350

Ala Leu Gly Asp Gly Gly Arg Ser Tyr Val Val Gly Phe Gly Thr Asn
        355                 360                 365

Pro Pro Val Arg Pro His His Arg Ser Ser Ser Cys Pro Asp Ala Pro
370                 375                 380

Ala Val Cys Asp Trp Asn Thr Tyr Asn Ser Ala Gly Pro Asn Ala His
385                 390                 395                 400

Val Leu Thr Gly Ala Leu Val Gly Gly Pro Asp Ser Asn Asp Ser Tyr
                405                 410                 415

Thr Asp Ala Arg Ser Asp Tyr Ile Ser Asn Glu Val Ala Thr Asp Tyr
            420                 425                 430

Asn Ala Gly Phe Gln Ser Ala Val Ala Gly Leu Leu Lys Ala Gly Val
        435                 440                 445

<210> SEQ ID NO 3
<211> LENGTH: 1427
<212> TYPE: DNA
<213> ORGANISM: Reticulitermes flavipes
<220> FEATURE:
<221> NAME/KEY: misc_feature
<223> OTHER INFORMATION: cDNA encoding exoglucanase Cell-3
<220> FEATURE:
<221> NAME/KEY: misc_feature
<222> LOCATION: (769)..(769)
<223> OTHER INFORMATION: n is a, c, g, or t

<400> SEQUENCE: 3
gctcttgaga ttggaactca acaaacggag actcatccgc agctgtcgtg gcagagctgt      60
tcaagtggtg gatcgtgctc gtcaaagtcc ggctcaattg ttcttgattc caattggaga     120
tgggttcatg acagcggcac caccaattgc tatgatggaa atttgtggac caaggatctt     180
tgctcgagtg cagacacatg tgtcagcaaa tgttacatcg agggggcaga ctattcgggg     240
acttatggaa ttacgagcag tggttcaaag ctgaccctca aatttgtcac gaaaggatcg     300
tattcaacaa acatcggaag tcgtgtttac ttgttgaaag atgagaatac gtatgagaca     360
ttcaaattga gaataatga gttcacgttc acagtagatg attctcaact tgattgtgga     420
ttgaatggtg cttttgtattt tgttgcaatg gatgcagatt ggtgggaaac agaaatatcc     480
cgcattcaag ccagggggcga aatatggaag gggatattgt gatgggcagt gcccgcatga     540
catgaaagtc agcagtggaa gggcaaatgt tgatggctgg aaaccacagg acaatgatga     600
aaattcaggg aatggaaagc ttggaacatg ctgctgggag atggatatt gggaaggcaa     660 cttagtttcc caggcgtaca cagttcacgc tggctcgaaa agtggacagt atgaatgcac     720
gggaactcaa tgcggagaca cagattcagg tgagagattc aaaggaacnt gcgcaaaga     780 tggatgcgac tttgcttcat acagatgggg tgccaccgat tactatggtc cgggaaagac     840
```

```
tgttgatacc aaacaaccca tgacggttgt cactcaattc attggagatc cgttgacaga      900
aatcaaacgt gtctatgttc aaggtggtaa ggtgattaac aactcgaaga catccaactt      960
gggttctgtg tacgattcgc ttactgaagc gttctgtgat gacaccaaac aagtcactgg     1020
agacaccaac gatttcaaag caaagggagg tatgtctggg tttagcaaga atttggacac     1080
tccacaagtt ttggtcatgt cactgtggga tgatcacacg gcgaatatgt tgtggcttga     1140
ttcgacgtat ccgaccgact cgacgaaacc gggagcggcg cgtggaactt gtgccgtaac     1200
gtcaggtgat cccaaggacg ttgaaagcaa gcaagcaaat tcgcaggttg tgtattcgga     1260
catcaagttt gggcccatta actcaacata caaagccaat taaagaaaca caacaaagct     1320
tttgggttaa atttattttt tttcagagtg ttgtccattt tccatttttt ttgaatgttt     1380
ttaaaaaagt tttgtttatt gggggtaaa aaaaaaaaaa aaaaaaa                    1427
```

<210> SEQ ID NO 4
<211> LENGTH: 292
<212> TYPE: PRT
<213> ORGANISM: Reticulitermes flavipes
<220> FEATURE:
<221> NAME/KEY: misc_feature
<223> OTHER INFORMATION: amino acid sequence exoglucanase (Cell-3)

<400> SEQUENCE: 4

```
Met Val Leu Cys Ile Leu Leu Gln Trp Met Gln Ile Gly Gly Lys Gln
1               5                   10                  15

Lys Tyr Pro Ala Phe Lys Pro Gly Ala Lys Tyr Gly Arg Gly Tyr Cys
                20                  25                  30

Asp Gly Gln Cys Pro His Asp Met Lys Val Ser Ser Gly Arg Ala Asn
            35                  40                  45

Val Asp Gly Trp Lys Pro Gln Asp Asn Asp Glu Asn Ser Gly Asn Gly
        50                  55                  60

Lys Leu Gly Thr Cys Cys Trp Glu Met Asp Ile Trp Glu Gly Asn Leu
65                  70                  75                  80

Val Ser Gln Ala Tyr Thr Val His Ala Gly Ser Lys Ser Gly Gln Tyr
                85                  90                  95

Glu Cys Thr Gly Thr Gln Cys Gly Asp Thr Asp Ser Gly Glu Arg Phe
                100                 105                 110

Lys Gly Thr Cys Asp Lys Asp Gly Cys Asp Phe Ala Ser Tyr Arg Trp
            115                 120                 125

Gly Ala Thr Asp Tyr Tyr Gly Pro Gly Lys Thr Val Asp Thr Lys Gln
        130                 135                 140

Pro Met Thr Val Val Thr Gln Phe Ile Gly Asp Pro Leu Thr Glu Ile
145                 150                 155                 160

Lys Arg Val Tyr Val Gln Gly Gly Lys Val Ile Asn Asn Ser Lys Thr
                165                 170                 175

Ser Asn Leu Gly Ser Val Tyr Asp Ser Leu Thr Glu Ala Phe Cys Asp
                180                 185                 190

Asp Thr Lys Gln Val Thr Gly Asp Thr Asn Asp Phe Lys Ala Lys Gly
            195                 200                 205

Gly Met Ser Gly Phe Ser Lys Asn Leu Asp Thr Pro Gln Val Leu Val
        210                 215                 220

Met Ser Leu Trp Asp Asp His Thr Ala Asn Met Leu Trp Leu Asp Ser
225                 230                 235                 240

Thr Tyr Pro Thr Asp Ser Thr Lys Pro Gly Ala Ala Arg Gly Thr Cys
                245                 250                 255

Ala Val Thr Ser Gly Asp Pro Lys Asp Val Glu Ser Lys Gln Ala Asn
```

```
                260                 265                 270
Ser Gln Val Val Tyr Ser Asp Ile Lys Phe Gly Pro Ile Asn Ser Thr
        275                 280                 285

Tyr Lys Ala Asn
    290
```

<210> SEQ ID NO 5
<211> LENGTH: 1915
<212> TYPE: DNA
<213> ORGANISM: Reticulitermes flavipes
<220> FEATURE:
<221> NAME/KEY: misc_feature
<223> OTHER INFORMATION: nucleotide sequence beta-glucosidase "contig 771"

<400> SEQUENCE: 5

| | | | | | |
|---|---|---|---|---|---|
| atataaacaa | aggacgtctc | tgtttctctg | gtgttctgac | atcctcacgt | ctagggcgct | 60 |
| tgacagagca | acgagatgag | gttacagacg | gtttgcttcg | tcatctttgt | gacggcagta | 120 |
| ttcggggctg | acgtcgataa | cgaaaccctc | ttcacgtttc | ctgaagactt | taagttaggc | 180 |
| gccgctacgg | cttcatacca | gattgaagga | ggatggaatg | cggatggaaa | gggtgtcaat | 240 |
| atatgggaca | aactgacaca | tgagcgctca | caattagtgg | ttgataaatc | aagcggtgac | 300 |
| gtggctgacg | actcgtatca | tctttataag | gaggacgtga | agcttctgaa | gaacatgggg | 360 |
| gcacaacttt | atcgcttctc | tatatcttgg | gctcgcatcc | tgcctgaagg | acatgataat | 420 |
| aaggtgaacc | aggcgggcat | tgagtactac | aacaagctca | tagacgaact | tctagacaat | 480 |
| ggaatagagc | cgatggttac | tatgtatcac | tgggatctac | cccagacact | ccaagacctg | 540 |
| ggaggatggc | caaatagaga | attggcaaaa | tactccgaga | attacgcccg | cgttttattt | 600 |
| caaaactttg | gagaccgggt | taaattgtgg | ctcacattca | atgagcctct | gactttcatg | 660 |
| gatgcatatg | catctgagac | aggaatggct | ccatcaattg | acacacccgg | tatcggcgat | 720 |
| taccttgcgg | cacacactgt | gatccttgcc | catgccaata | tctaccgtat | gtatgagagg | 780 |
| gaattcaaag | aggaacagaa | aggaaaggtt | ggtatcgcac | tcaacataca | ctggtgtgag | 840 |
| ccggtgacta | attccacaaa | ggacgttgag | gcttgtgaaa | ggtatcaaca | gttcaacctg | 900 |
| ggaatatacg | ctcatcccat | cttctctgta | gagggcgatt | accccagtgt | tttgaaagcg | 960 |
| agggtagacg | caaacagcgt | aacggaaggt | tacaccacat | ctcgtctacc | taaattcact | 1020 |
| acagaggaag | tagatttcat | cagaggaaca | catgatttct | tgggtctgaa | tttctacact | 1080 |
| gctgtaacgg | gagcagatgg | agttgaaggg | aaccccccgt | cgcggtacag | agacatgggc | 1140 |
| gcgatcacat | cacaggatcc | ggactggccc | cagtctgctt | cttcatggct | cagagttgta | 1200 |
| ccatggggat | tccgcaagga | acttaactgg | atcgcgaacg | aatacggtaa | ccctcctata | 1260 |
| tacatcactg | aaaatggctt | ctccgactac | ggaggcctca | atgatacaga | cagagtgctg | 1320 |
| tactacactg | aacatttaaa | ggagatgctg | aaggcaaatc | acatagatga | agttaacgta | 1380 |
| gtcggataca | caacctggag | accagtagac | aatttcgaat | ggctgcgagg | atatactgag | 1440 |
| aggttcggta | tacatgaagt | gaatttcaac | gacccaagtc | gcccacgagt | tcccaaggag | 1500 |
| tcagcaaagg | tgctcacaga | gatcttcaac | acaaggagga | ttccagaacg | cttcctagac | 1560 |
| taacttcata | ttcaagacgc | aaagactttat | atcaaaaatt | aatttaaaag | agggcttact | 1620 |
| gctgactgtg | agttccctca | aaacagcaat | aaggtttatg | atcatggaaa | acacttccaa | 1680 |
| ttaaataaac | ttatatacaa | aatataattt | acattccttc | aacaaatgca | atatattctt | 1740 |
| taaaagttaa | tgttaatcat | ccttaccaac | atattctcac | atatattctt | ataaaactac | 1800 |

```
acgcattata acgaccacta tcttcagtct ttgtcagagt aacatgtaac ttctacctgc   1860
tgatggtcgg cgtacgcggc ccaaacattg tagagaacat aaacagtgtg tgtga        1915
```

<210> SEQ ID NO 6
<211> LENGTH: 495
<212> TYPE: PRT
<213> ORGANISM: Reticulitermes flavipes
<220> FEATURE:
<221> NAME/KEY: misc_feature
<223> OTHER INFORMATION: amino acid sequence beta-glucosidase "contig 771"

<400> SEQUENCE: 6

```
Met Arg Leu Gln Thr Val Cys Phe Val Ile Phe Val Thr Ala Val Phe
1               5                   10                  15

Gly Ala Asp Val Asp Asn Glu Thr Leu Phe Thr Phe Pro Glu Asp Phe
            20                  25                  30

Lys Leu Gly Ala Ala Thr Ala Ser Tyr Gln Ile Glu Gly Gly Trp Asn
        35                  40                  45

Ala Asp Gly Lys Gly Val Asn Ile Trp Asp Lys Leu Thr His Glu Arg
    50                  55                  60

Ser Gln Leu Val Val Asp Lys Ser Ser Gly Asp Val Ala Asp Asp Ser
65                  70                  75                  80

Tyr His Leu Tyr Lys Glu Asp Val Lys Leu Leu Lys Asn Met Gly Ala
                85                  90                  95

Gln Leu Tyr Arg Phe Ser Ile Ser Trp Ala Arg Ile Leu Pro Glu Gly
            100                 105                 110

His Asp Asn Lys Val Asn Gln Ala Gly Ile Glu Tyr Tyr Asn Lys Leu
        115                 120                 125

Ile Asp Glu Leu Leu Asp Asn Gly Ile Glu Pro Met Val Thr Met Tyr
    130                 135                 140

His Trp Asp Leu Pro Gln Thr Leu Gln Asp Leu Gly Gly Trp Pro Asn
145                 150                 155                 160

Arg Glu Leu Ala Lys Tyr Ser Glu Asn Tyr Ala Arg Val Leu Phe Gln
                165                 170                 175

Asn Phe Gly Asp Arg Val Lys Leu Trp Leu Thr Phe Asn Glu Pro Leu
            180                 185                 190

Thr Phe Met Asp Ala Tyr Ala Ser Glu Thr Gly Met Ala Pro Ser Ile
        195                 200                 205

Asp Thr Pro Gly Ile Gly Asp Tyr Leu Ala Ala His Thr Val Ile Leu
    210                 215                 220

Ala His Ala Asn Ile Tyr Arg Met Tyr Glu Arg Glu Phe Lys Glu Glu
225                 230                 235                 240

Gln Lys Gly Lys Val Gly Ile Ala Leu Asn Ile His Trp Cys Glu Pro
                245                 250                 255

Val Thr Asn Ser Thr Lys Asp Val Glu Ala Cys Glu Arg Tyr Gln Gln
            260                 265                 270

Phe Asn Leu Gly Ile Tyr Ala His Pro Ile Phe Ser Val Glu Gly Asp
        275                 280                 285

Tyr Pro Ser Val Leu Lys Ala Arg Val Asp Ala Asn Ser Val Thr Glu
    290                 295                 300

Gly Tyr Thr Thr Ser Arg Leu Pro Lys Phe Thr Glu Glu Val Asp
305                 310                 315                 320

Phe Ile Arg Gly Thr His Asp Phe Leu Gly Leu Asn Phe Tyr Thr Ala
                325                 330                 335

Val Thr Gly Ala Asp Gly Val Glu Gly Glu Pro Pro Ser Arg Tyr Arg
```

```
                 340             345             350
Asp Met Gly Ala Ile Thr Ser Gln Asp Pro Asp Trp Pro Gln Ser Ala
            355                 360                 365

Ser Ser Trp Leu Arg Val Val Pro Trp Gly Phe Arg Lys Glu Leu Asn
    370                 375                 380

Trp Ile Ala Asn Glu Tyr Gly Asn Pro Pro Ile Tyr Ile Thr Glu Asn
385                 390                 395                 400

Gly Phe Ser Asp Tyr Gly Gly Leu Asn Asp Thr Asp Arg Val Leu Tyr
                405                 410                 415

Tyr Thr Glu His Leu Lys Glu Met Leu Lys Ala Asn His Ile Asp Glu
            420                 425                 430

Val Asn Val Val Gly Tyr Thr Thr Trp Arg Pro Val Asp Asn Phe Glu
        435                 440                 445

Trp Leu Arg Gly Tyr Thr Glu Arg Phe Gly Ile His Glu Val Asn Phe
    450                 455                 460

Asn Asp Pro Ser Arg Pro Arg Val Pro Lys Glu Ser Ala Lys Val Leu
465                 470                 475                 480

Thr Glu Ile Phe Asn Thr Arg Arg Ile Pro Glu Arg Phe Leu Asp
                485                 490                 495

<210> SEQ ID NO 7
<211> LENGTH: 2067
<212> TYPE: DNA
<213> ORGANISM: Reticulitermes flavipes
<220> FEATURE:
<221> NAME/KEY: misc_feature
<223> OTHER INFORMATION: nucleotide sequence of Laccase Lacc-6

<400> SEQUENCE: 7
ctaatacgac tcactatagg gcaagcagtg gtatcaacgc agagtacgcg ggaagcagtg      60
gtatcaacgc agagtacgcg ggatacggcc ctatcagttt acagatcgga cgcctacatt     120
atgttgcctt gcgtcctgct tgcttgcgca attggtgtgg cttctgcaac atcagtgctc     180
ctgaattcat accttcagcc caacgatgac attgatcgaa acacgtacct cctaaatgca     240
aaaagcaaca actgtgcccg tatatgcaat gggacagagg cgcccaaaat ctgctactac     300
caatggacaa ttgagaacta cgtgactctg tcagaagcgt gtgacaattg tcccttgaat     360
gtgacggcct gttacaacgc acagtgcatc acagctgatg gatatgagcg cagtatcctt     420
tcggtaaaca ggaaactacc ggggccttcc atcgaggtgt gcctcagaga cagagtaatt     480
gtggatataa ccaacaacat ggcagggagg actactagca tccactggca tgggtatttt     540
cagaaagggt cccagtacat ggacggagtt cccatggtaa cccagtgcac tatacatgag     600
ggtgacacat tccggtacga ctttatcgct aacaacgagg gaactcattt ctggcattcc     660
catgacggtt tgcagaagct cgatggcgtg acaggtaact tggtggttag ggtgcctaaa     720
aatttcgacc cgaacggaca actgtacgat ttcgatctac agaacacaaa attttcatc     780 agcgactggc tacatctttc cgcagatgac cactttcccg gactccgagc gacaaatcca     840
ggacaagatg ctaactcctt tctcattaac ggcagaggac gtaccttgat tggaactcag     900
tccaccaaca caccgtatgc gcagataaat gtgcagtggg gcaggaggta ccggcttcgc     960
attgtgggct ccctgtgcac tgtgtgcccc acacagctca ccattgacgg gcacaaaatt    1020
acagtcatag ccactgacgg caattctgtg gctcctgcca gagtcgactc cctcatcatt    1080
tactctggtg aaagatacga cgtcgtgtta gaagccacta atacggaagg atcttactgg    1140
atccatctaa aaggcctcgc cacttgtgtt ggaagtagag tttaccagct gggggtgttg    1200
```

-continued

```
caatatgaaa atacaacaac caataaactg catgctctga cacctgatcc aggttacgac    1260
ggattcccgc aaccagcaag ctaccgggtc ctgaacccag agaacgcaag ctgtagcatc    1320
ggctcgacag gcctatgcgt cacgcaactc gcgaactcgg accccgtgcc acgggacatc    1380
ctaacccagc tcccggacat caactatctt ctccaatttg gatttgaaac tttcgactcc    1440
agaagtttct tcaaagctta cgacagatat tttgtcagcc cctttctcga gttactcagc    1500
agtaccgtca acaacattct tttcgtttcg cccccatctc cgctcctctc acaaggggg    1560 gatgtaccag acgacatcct atgcccgacg ggggctgatg gcctgcccca gtgtcccgga    1620
ggaaactcct actgcacatg tgtccatgtc atcaaaatca aactgggtgc tttggtgcag    1680
atcatcctgt cggaccagtc acccaaatcc gacctgaacc atccgttcca tatacacgga    1740
catgcgtttt acgtcctggg catggggcaa tacgctgcag acagacggc gcaggacctc    1800 cttaactcct tgaagagtaa cgtgagtagt gtgtcccctg cgccggttct taaagatacc    1860
gtcgcagttc catctggcgg ctacgcgatc atcaagttca gaccaaaaaa ccctggttac    1920
tggttccttc actgccactt cctgtaccat gtagcgaccg ggatgagtgt tgtgctccag    1980
gtgggagaaa caagtgacta tcccctaca ccagacggct tccccaagtg tggaagcttc    2040
acacctcccg tgaacaccaa ctgaagt                                        2067
```

<210> SEQ ID NO 8
<211> LENGTH: 687
<212> TYPE: PRT
<213> ORGANISM: Reticulitermes flavipes
<220> FEATURE:
<221> NAME/KEY: misc_feature
<223> OTHER INFORMATION: amino acid sequence Laccase Lacc-6

<400> SEQUENCE: 8

```
Leu Ile Arg Leu Thr Ile Gly Gln Ala Val Val Ser Thr Gln Ser Thr
1               5                   10                  15

Arg Glu Ala Val Val Ser Thr Gln Ser Thr Arg Asp Thr Ala Leu Ser
            20                  25                  30

Val Tyr Arg Ser Asp Ala Tyr Ile Met Leu Pro Cys Val Leu Leu Ala
        35                  40                  45

Cys Ala Ile Gly Val Ala Ser Ala Thr Ser Val Leu Leu Asn Ser Tyr
    50                  55                  60

Leu Gln Pro Asn Asp Asp Ile Asp Arg Asn Thr Tyr Leu Leu Asn Ala
65                  70                  75                  80

Lys Ser Asn Asn Cys Ala Arg Ile Cys Asn Gly Thr Glu Ala Pro Lys
                85                  90                  95

Ile Cys Tyr Tyr Gln Trp Thr Ile Glu Asn Tyr Val Thr Leu Ser Glu
            100                 105                 110

Ala Cys Asp Asn Cys Pro Leu Asn Val Thr Ala Cys Tyr Asn Ala Gln
        115                 120                 125

Cys Ile Thr Ala Asp Gly Tyr Glu Arg Ser Ile Leu Ser Val Asn Arg
    130                 135                 140

Lys Leu Pro Gly Pro Ser Ile Glu Val Cys Leu Arg Asp Arg Val Ile
145                 150                 155                 160

Val Asp Ile Thr Asn Asn Met Ala Gly Arg Thr Thr Ser Ile His Trp
                165                 170                 175

His Gly Val Phe Gln Lys Gly Ser Gln Tyr Met Asp Gly Val Pro Met
            180                 185                 190

Val Thr Gln Cys Thr Ile His Glu Gly Asp Thr Phe Arg Tyr Asp Phe
        195                 200                 205
```

```
Ile Ala Asn Asn Glu Gly Thr His Phe Trp His Ser His Asp Gly Leu
210                 215                 220
Gln Lys Leu Asp Gly Val Thr Gly Asn Leu Val Arg Val Pro Lys
225                 230                 235                 240
Asn Phe Asp Pro Asn Gly Gln Leu Tyr Asp Phe Asp Leu Pro Glu His
            245                 250                 255
Lys Ile Phe Ile Ser Asp Trp Leu His Leu Ser Ala Asp His Phe
            260                 265                 270
Pro Gly Leu Arg Ala Thr Asn Pro Gly Gln Asp Ala Asn Ser Phe Leu
            275                 280                 285
Ile Asn Gly Arg Gly Arg Thr Leu Ile Gly Thr Gln Ser Thr Asn Thr
290                 295                 300
Pro Tyr Ala Gln Ile Asn Val Gln Trp Gly Arg Arg Tyr Arg Leu Arg
305                 310                 315                 320
Ile Val Gly Ser Leu Cys Thr Val Cys Pro Thr Gln Leu Thr Ile Asp
                325                 330                 335
Gly His Lys Ile Thr Val Ile Ala Thr Asp Gly Asn Ser Val Ala Pro
                340                 345                 350
Ala Arg Val Asp Ser Leu Ile Ile Tyr Ser Gly Glu Arg Tyr Asp Val
            355                 360                 365
Val Leu Glu Ala Thr Asn Thr Glu Gly Ser Tyr Trp Ile His Leu Lys
370                 375                 380
Gly Leu Ala Thr Cys Val Gly Ser Arg Val Tyr Gln Leu Gly Val Leu
385                 390                 395                 400
Gln Tyr Glu Asn Thr Thr Thr Asn Lys Leu His Ala Leu Thr Pro Asp
            405                 410                 415
Pro Gly Tyr Asp Gly Phe Pro Gln Pro Ala Ser Tyr Arg Val Leu Asn
            420                 425                 430
Pro Glu Asn Ala Ser Cys Ser Ile Gly Ser Thr Gly Leu Cys Val Thr
            435                 440                 445
Gln Leu Ala Asn Ser Asp Pro Val Pro Arg Asp Ile Leu Thr Gln Leu
450                 455                 460
Pro Asp Ile Asn Tyr Leu Leu Gln Phe Gly Phe Glu Thr Phe Asp Ser
465                 470                 475                 480
Arg Ser Phe Phe Lys Ala Tyr Asp Arg Tyr Phe Val Ser Pro Phe Leu
            485                 490                 495
Glu Leu Leu Ser Ser Thr Val Asn Asn Ile Ser Phe Val Ser Pro Pro
            500                 505                 510
Ser Pro Leu Leu Ser Gln Arg Gly Asp Val Pro Asp Asp Ile Leu Cys
            515                 520                 525
Pro Thr Gly Ala Asp Gly Leu Pro Gln Cys Pro Gly Gly Asn Ser Tyr
530                 535                 540
Cys Thr Cys Val His Val Ile Lys Ile Lys Leu Gly Ala Leu Val Gln
545                 550                 555                 560
Ile Ile Leu Ser Asp Gln Ser Pro Lys Ser Asp Leu Asn His Pro Phe
            565                 570                 575
His Ile His Gly His Ala Phe Tyr Val Leu Gly Met Gly Gln Tyr Ala
            580                 585                 590
Ala Gly Gln Thr Ala Gln Asp Leu Leu Asn Ser Leu Lys Ser Asn Val
            595                 600                 605
Ser Ser Val Ser Pro Ala Pro Val Leu Lys Asp Thr Val Ala Val Pro
            610                 615                 620
Ser Gly Gly Tyr Ala Ile Ile Lys Phe Arg Pro Lys Asn Pro Gly Tyr
625                 630                 635                 640
```

```
Trp Phe Leu His Cys His Phe Leu Tyr His Val Ala Thr Gly Met Ser
                645                 650                 655
Val Val Leu Gln Val Gly Glu Thr Ser Asp Tyr Pro Pro Thr Pro Asp
                660                 665                 670
Gly Phe Pro Lys Cys Gly Ser Phe Thr Pro Pro Val Asn Thr Asn
                675                 680                 685
```

<210> SEQ ID NO 9
<211> LENGTH: 2039
<212> TYPE: DNA
<213> ORGANISM: Reticulitermes flavipes
<220> FEATURE:
<221> NAME/KEY: misc_feature
<223> OTHER INFORMATION: nucleotide sequence of Laccase Lacc-7

<400> SEQUENCE: 9

```
ctaatacgac tcactatagg gcaagcagtg gtatcaacgc agagtacgcg gggcatacgg    60
ccctatcagt ttacagatcg gacgcctaca ttatgttgcc ttgcgtcctg cttgcttgcg   120
caattggtgt ggcttctgca acatcagtgc tcctgaattc ataccttcag cccaacgatg   180
acattgatcg aaacacgtac ctcctaaatg caaaaagcaa caactgtgcc cgtatatgca   240
atgggacaga ggcgcccaaa atctgctact accaatggac aattgagaac tacgtgactc   300
tgtcagaagc gtgtgacatt tgtcccttga atgtgacggc ctgttacaac gcacagtgca   360
tcacagctga tggatatgag cgcagtatcc tttcggtaaa caggaaacta ccggggcctt   420
ccatcgaggt gtgcctcaga gacagagtaa ttgtggatat aaccaacaac atggcaggga   480
ggactactag catccactgg catggggtat ttcagaaagg gtcccagtac atggacggag   540
ttcccatggt aacccagtgc actatacatg agggtgacac attccggtac gactttatcg   600
ctaacaacga gggaactcat ttctggcatt cccatgacgg tttgcagaag ctcgatggcg   660
tgacaggtaa cttggtggtt agggtgccta aaaatttcga cccgaacgga caactgtacg   720
atttcgatct accagaacac aaaattttca tcagcgactg gctacatctt tccgcagatg   780
accactttcc cggactccga gcgacaaatc caggacaaga tgctaactcc tttctcatta   840
acggcagagg acgtaccttg attggaactc agtccaccaa cacaccgtat gcgcagataa   900
atgtgcagtg gggcaggagg taccggcttc gcattgtggg ctccctgtgc actgtgtgcc   960
ccacacagct caccattgac gggcacaaaa ttacagtcat agccactgac ggcaattctg  1020
tggctcctgc cagagtcgac tccctcatca tttactctgg tgaaagatac gacgtcgtgt  1080
tagaagccac taatacggaa ggatcttact ggatccatct aaaaggcctc gccacttgtg  1140
ttggaagtag agtttaccag ctgggggtgt tgcaatatga aaatacaaca accaataaac  1200
tgcatgctct gacacctgat ccaggttacg acggattccc gcaaccagca agctaccggg  1260
tcctgaaccc agagaacgca agctgtagca tcggctcgac aggcctatgc gtcacgcaac  1320
tcgcgaactc ggaccccgtg ccacgggaca tcctaaccca gctcccggac atcaactatc  1380
ttctccaatt tggatttgaa actttcgact ccagaagttt cttcaaagct tacgacagat  1440
attttgtcag cccctttctc gagttactca gcagtaccgt caacaacatt tctttcgttt  1500
cgcccccatc tccgctcctc tcacaaaggg gggatgtacc agacgacatc ctatgcccga  1560
cgggggctga tggcctgccc cagtgtcccg gaggaaactc ctactgcaca tgtgtccatg  1620
tcatcaaaat caaactgggt gctttggtgc agatcatcct gtcggaccag tcacccaaat  1680
ccgacctgaa ccatccgttc catatacacg gacatgcgtt ttacgtcctg ggcatggggc  1740
aatacgctgc aggacagaca gcgcaggacc tccttaactc cttgaagagt aacgtgagta  1800
```

```
gtgtgtcccc tgcgccggtt cttaaagata ccgtcgcagt tccatctggc ggctacgcga    1860
tcatcaagtt cagaccaaaa aaccctggtt actggttcct tcactgccac ttcctgtacc    1920
atgtagcgac cgggatgagt gttgtgctcc aggtgggaga acaagtgac tatccccta     1980 caccagacgg cttccccaag tgtggaagct tcacacctcc cgtgaacacc aactgaagt    2039
```

<210> SEQ ID NO 10
<211> LENGTH: 677
<212> TYPE: PRT
<213> ORGANISM: Reticulitermes flavipes
<220> FEATURE:
<221> NAME/KEY: misc_feature
<223> OTHER INFORMATION: amino acid sequence Laccase Lacc-7

<400> SEQUENCE: 10

```
Asn Thr Thr His Tyr Arg Ala Ser Ser Gly Ile Asn Ala Glu Tyr Ala
1               5                   10                  15

Gly His Thr Ala Leu Ser Val Tyr Arg Ser Asp Ala Tyr Ile Met Leu
            20                  25                  30

Pro Cys Val Leu Leu Ala Cys Ala Ile Gly Val Ala Ser Ala Thr Ser
        35                  40                  45

Val Leu Leu Asn Ser Tyr Leu Gln Pro Asn Asp Ile Asp Arg Asn
50                  55                  60

Thr Tyr Leu Leu Asn Ala Lys Ser Asn Asn Cys Ala Arg Ile Cys Asn
65                  70                  75                  80

Gly Thr Glu Ala Pro Lys Ile Cys Tyr Tyr Gln Trp Thr Ile Glu Asn
                85                  90                  95

Tyr Val Thr Leu Ser Glu Ala Cys Asp Ile Cys Pro Leu Asn Val Thr
            100                 105                 110

Ala Cys Tyr Asn Ala Gln Cys Ile Thr Ala Asp Gly Tyr Glu Arg Ser
        115                 120                 125

Ile Leu Ser Val Asn Arg Lys Leu Pro Gly Pro Ser Ile Glu Val Cys
    130                 135                 140

Leu Arg Asp Arg Val Ile Val Asp Ile Thr Asn Asn Met Ala Gly Arg
145                 150                 155                 160

Thr Thr Ser Ile His Trp His Gly Val Phe Gln Lys Gly Ser Gln Tyr
                165                 170                 175

Met Asp Gly Val Pro Met Val Thr Gln Cys Thr Ile His Glu Gly Asp
            180                 185                 190

Thr Phe Arg Tyr Asp Phe Ile Ala Asn Asn Glu Gly Thr His Phe Trp
        195                 200                 205

His Ser His Asp Gly Leu Gln Lys Leu Asp Gly Val Thr Gly Asn Leu
    210                 215                 220

Val Val Arg Val Pro Lys Asn Phe Asp Pro Asn Gly Gln Leu Tyr Asp
225                 230                 235                 240

Phe Asp Leu Pro Glu His Lys Ile Phe Ile Ser Asp Trp Leu His Leu
                245                 250                 255

Ser Ala Asp Asp His Phe Pro Gly Leu Arg Ala Thr Asn Pro Gly Gln
            260                 265                 270

Asp Ala Asn Ser Phe Leu Ile Asn Gly Arg Gly Arg Thr Leu Ile Gly
        275                 280                 285

Thr Gln Ser Thr Asn Thr Pro Tyr Ala Gln Ile Asn Val Gln Trp Gly
    290                 295                 300

Arg Arg Tyr Arg Leu Arg Ile Val Gly Ser Leu Cys Thr Val Cys Pro
305                 310                 315                 320
```

```
Thr Gln Leu Thr Ile Asp Gly His Lys Ile Thr Val Ile Ala Thr Asp
            325                 330                 335

Gly Asn Ser Val Ala Pro Ala Arg Val Asp Ser Leu Ile Ile Tyr Ser
            340                 345                 350

Gly Glu Arg Tyr Asp Val Val Leu Glu Ala Thr Asn Thr Glu Gly Ser
            355                 360                 365

Tyr Trp Ile His Leu Lys Gly Leu Ala Thr Cys Val Gly Ser Arg Val
        370                 375                 380

Tyr Gln Leu Gly Val Leu Gln Tyr Glu Asn Thr Thr Asn Lys Leu
385                 390                 395                 400

His Ala Leu Thr Pro Asp Pro Gly Tyr Asp Gly Phe Pro Gln Pro Ala
            405                 410                 415

Ser Tyr Arg Val Leu Asn Pro Glu Asn Ala Ser Cys Ser Ile Gly Ser
            420                 425                 430

Thr Gly Leu Cys Val Thr Gln Leu Ala Asn Ser Asp Pro Val Pro Arg
        435                 440                 445

Asp Ile Leu Thr Gln Leu Pro Asp Ile Asn Tyr Leu Leu Gln Phe Gly
        450                 455                 460

Phe Glu Thr Phe Asp Ser Arg Ser Phe Lys Ala Tyr Asp Arg Tyr
465                 470                 475                 480

Phe Val Ser Pro Phe Leu Glu Leu Leu Ser Ser Thr Val Asn Asn Ile
            485                 490                 495

Ser Phe Val Ser Pro Pro Ser Pro Leu Leu Ser Gln Arg Gly Asp Val
            500                 505                 510

Pro Asp Asp Ile Leu Cys Pro Thr Gly Ala Asp Gly Leu Pro Gln Cys
        515                 520                 525

Pro Gly Gly Asn Ser Tyr Cys Thr Cys Val His Val Ile Lys Ile Lys
            530                 535                 540

Leu Gly Ala Leu Val Gln Ile Ile Leu Ser Asp Gln Ser Pro Lys Ser
545                 550                 555                 560

Asp Leu Asn His Pro Phe His Ile His Gly His Ala Phe Tyr Val Leu
            565                 570                 575

Gly Met Gly Gln Tyr Ala Ala Gly Gln Thr Ala Gln Asp Leu Leu Asn
            580                 585                 590

Ser Leu Lys Ser Asn Val Ser Ser Val Ser Pro Ala Pro Val Leu Lys
            595                 600                 605

Asp Thr Val Ala Val Pro Ser Gly Gly Tyr Ala Ile Ile Lys Phe Arg
            610                 615                 620

Pro Lys Asn Pro Gly Tyr Trp Phe Leu His Cys His Phe Leu Tyr His
625                 630                 635                 640

Val Ala Thr Gly Met Ser Val Val Leu Gln Val Gly Glu Thr Ser Asp
            645                 650                 655

Tyr Pro Pro Thr Pro Asp Gly Phe Pro Lys Cys Gly Ser Phe Thr Pro
            660                 665                 670

Pro Val Asn Thr Asn
        675

<210> SEQ ID NO 11
<211> LENGTH: 2087
<212> TYPE: DNA
<213> ORGANISM: Reticulitermes flavipes
<220> FEATURE:
<221> NAME/KEY: misc_feature
<223> OTHER INFORMATION: nucleotide sequence of Laccase Lacc-12

<400> SEQUENCE: 11
```

```
ctaatacgac tcactatagg gcaagcagtg gtatcaacgc agagtacgcg gggatacggc    60
cctatcagtt gtgtaaataa ctttcgttaa ggttttcatt accaaagttg ctgtaagttt   120
acagatcgga cgcctacatt atgttgcctt gcgtcctgct tgcttgcgca attggtgtgg   180
cttctgcaac atcagtgctc ctgaattcat accttcagcc caacgatgac attgatcgaa   240
acacgtacct cctaaatgca aaaagcaaca actgtgcccg tatatgcaat gggacagagg   300
cgcccaaaat ctgctactac caatggacaa ttgagaacta cgtgactctg tcagaagcgt   360
gtgacaattg tcccttgaat gtgacggcct gttacaacgc acagtgcatc acagctgatg   420
gatatgagcg cagtatcctt tcggtaaaca ggaaactacc ggggccttcc atcgaggtgt   480
gcctcagaga cagagtaatt gtggatataa ccaacaacat ggcagggagg actactagca   540
tccactggca tggggtattt cagaaagggt cccagtacat ggacggagtt ccatggtaa    600
cccagtgcac tatacatgag ggtgacacac tccggtacga ctttatcgct aacaacgagg   660
gaactcattt ctggcattcc catgacggtt gcagaagct cgatggcgtg acaggtaact   720
tggtggttag ggtgcctaaa aatttcgacc cgaacggaca actgtacgat ttcgatctac   780
cagaacacaa aattttcatc agcgactggc tacatctttc cgcagatgac cactttcccg   840
gactccgagc gacaaatcca ggacaagatg ctaactcctt tctcattaac ggcagaggac   900
gtaccttgat tggaactcag tccaccaaca caccgtatgc gcagataaat gtgcagtggg   960
gcaggaggta ccggcttcgc attgtgggct ccctgtgcac tgtgtgcccc acacagctca  1020
ccattgacgg gcacaaaatt acagtcatag ccactgacgg caattctgtg gctcctgcca  1080
gagtcgactc cctcatcatt tactctggtg aaagatacga cgtcgtgtta gaagccacta  1140
atacggaagg atcttactgg atccatctaa aaggcctcgt cacttgtgtt ggaagcagag  1200
tttaccagct gggggtgttg caatatgaaa atacaacaac caataaactg catgctctga  1260
cacctgatcc aggttacgac ggattcccgc aaccagcaag ctaccgggtc ctgaacccag  1320
agaacgcaag ctgtagcatc ggctcgacag gcctatgcgt cacgcaactc gcgaactcgg  1380
accccgtgcc acgggacatc ctaacccagc tcccggacat caactatctt ctccaatttg  1440
gatttaaaat tttcgactcc agaagtttct tcaaagctta cgacagatat tttgtcagcc  1500
cctttctcga cttagtcagc agtaccgtca acaacatttc ttccgtttcg cccccatctc  1560
cgctcctctc acaagggggg gatgtaccag acgacgtcct atgcccgacg ggggctgatg  1620
gcctgcccca gtgtcccgga ggaaactcct actgcacatg tgtccatgtc atcaaaatca  1680
aactgggtgc tttggtgcag atcatcctgt cggaccagac acccaaatcc ggcctgaacc  1740
atccgttcca tctacacgga catgcgtttt acgtcctggg catgggcaa tacgctgcag  1800
gacagacagc gcaggacctc cttaactcct tgaagagtaa cgtgagtagt gtgtcccctg  1860
cgccggttct taaagatacc atcgcagttc catctggcgg ctacgcgatc atcaagttca  1920
gaccaaaaaa tcctgttac tggttccttc actgccactt cctgtaccat gtagcgaccg  1980
ggatgagtgt tgtgctccag gtgggagaaa caagtgacta tcccctaca ccagacggct  2040
tccccaagtg tggaagcttc acacctcccg tgaacaccaa ctgaagt              2087
```

<210> SEQ ID NO 12
<211> LENGTH: 655
<212> TYPE: PRT
<213> ORGANISM: Reticulitermes flavipes
<220> FEATURE:
<221> NAME/KEY: misc_feature
<223> OTHER INFORMATION: amino acid sequence Laccase Lacc-12

<400> SEQUENCE: 12

```
Val Tyr Arg Ser Asp Ala Tyr Ile Met Leu Pro Cys Val Leu Ala
  1               5                  10                  15

Cys Ala Ile Gly Val Ala Ser Ala Thr Ser Val Leu Leu Asn Ser Tyr
             20                  25                  30

Leu Gln Pro Asn Asp Asp Ile Asp Arg Asn Thr Tyr Leu Leu Asn Ala
         35                  40                  45

Lys Ser Asn Asn Cys Ala Arg Ile Cys Asn Gly Thr Glu Ala Pro Lys
 50                  55                  60

Ile Cys Tyr Tyr Gln Trp Thr Ile Glu Asn Tyr Val Thr Leu Ser Glu
 65                  70                  75                  80

Ala Cys Asp Asn Cys Pro Leu Asn Val Thr Ala Cys Tyr Asn Ala Gln
                 85                  90                  95

Cys Ile Thr Ala Asp Gly Tyr Glu Arg Ser Ile Leu Ser Val Asn Arg
                100                 105                 110

Lys Leu Pro Gly Pro Ser Ile Glu Val Cys Leu Arg Asp Arg Val Ile
            115                 120                 125

Val Asp Ile Thr Asn Asn Met Ala Gly Arg Thr Thr Ser Ile His Trp
130                 135                 140

His Gly Val Phe Gln Lys Gly Ser Gln Tyr Met Asp Gly Val Pro Met
145                 150                 155                 160

Val Thr Gln Cys Thr Ile His Glu Gly Asp Thr Leu Arg Tyr Asp Phe
                165                 170                 175

Ile Ala Asn Asn Glu Gly Thr His Phe Trp His Ser His Asp Gly Leu
                180                 185                 190

Gln Lys Leu Asp Gly Val Thr Gly Asn Leu Val Val Arg Val Pro Lys
        195                 200                 205

Asn Phe Asp Pro Asn Gly Gln Leu Tyr Asp Phe Asp Leu Pro Glu His
210                 215                 220

Lys Ile Phe Ile Ser Asp Trp Leu His Leu Ser Ala Asp Asp His Phe
225                 230                 235                 240

Pro Gly Leu Arg Ala Thr Asn Pro Gly Gln Asp Ala Asn Ser Phe Leu
                245                 250                 255

Ile Asn Gly Arg Gly Arg Thr Leu Ile Gly Thr Gln Ser Thr Asn Thr
                260                 265                 270

Pro Tyr Ala Gln Ile Asn Val Gln Trp Gly Arg Arg Tyr Arg Leu Arg
            275                 280                 285

Ile Val Gly Ser Leu Cys Thr Val Cys Pro Thr Gln Leu Thr Ile Asp
290                 295                 300

Gly His Lys Ile Thr Val Ile Ala Thr Asp Gly Asn Ser Val Ala Pro
305                 310                 315                 320

Ala Arg Val Asp Ser Leu Ile Ile Tyr Ser Gly Glu Arg Tyr Asp Val
                325                 330                 335

Val Leu Glu Ala Thr Asn Thr Glu Gly Ser Tyr Trp Ile His Leu Lys
            340                 345                 350

Gly Leu Val Thr Cys Val Gly Ser Arg Val Tyr Gln Leu Gly Val Leu
        355                 360                 365

Gln Tyr Glu Asn Thr Thr Thr Asn Lys Leu His Ala Leu Thr Pro Asp
370                 375                 380

Pro Gly Tyr Asp Gly Phe Pro Gln Pro Ala Ser Tyr Arg Val Leu Asn
385                 390                 395                 400

Pro Glu Asn Ala Ser Cys Ser Ile Gly Ser Thr Gly Leu Cys Val Thr
                405                 410                 415

Gln Leu Ala Asn Ser Asp Pro Val Pro Arg Asp Ile Leu Thr Gln Leu
```

-continued

```
                420                 425                 430
Pro Asp Ile Asn Tyr Leu Leu Gln Phe Gly Phe Lys Ile Phe Asp Ser
            435                 440                 445

Arg Ser Phe Phe Lys Ala Tyr Asp Arg Tyr Phe Val Ser Pro Phe Leu
        450                 455                 460

Asp Leu Val Ser Ser Thr Val Asn Asn Ile Ser Ser Val Ser Pro Pro
465                 470                 475                 480

Ser Pro Leu Leu Ser Gln Arg Gly Asp Val Pro Asp Val Leu Cys
                485                 490                 495

Pro Thr Gly Ala Asp Gly Leu Pro Gln Cys Pro Gly Gly Asn Ser Tyr
            500                 505                 510

Cys Thr Cys Val His Val Ile Lys Ile Lys Leu Gly Ala Leu Val Gln
        515                 520                 525

Ile Ile Leu Ser Asp Gln Thr Pro Lys Ser Gly Leu Asn His Pro Phe
        530                 535                 540

His Leu His Gly His Ala Phe Tyr Val Leu Gly Met Gly Gln Tyr Ala
545                 550                 555                 560

Ala Gly Gln Thr Ala Gln Asp Leu Leu Asn Ser Leu Lys Ser Asn Val
                565                 570                 575

Ser Ser Val Ser Pro Ala Pro Val Leu Lys Asp Thr Ile Ala Val Pro
            580                 585                 590

Ser Gly Gly Tyr Ala Ile Ile Lys Phe Arg Pro Lys Asn Pro Gly Tyr
        595                 600                 605

Trp Phe Leu His Cys His Phe Leu Tyr His Val Ala Thr Gly Met Ser
        610                 615                 620

Val Val Leu Gln Val Gly Glu Thr Ser Asp Tyr Pro Pro Thr Pro Asp
625                 630                 635                 640

Gly Phe Pro Lys Cys Gly Ser Phe Thr Pro Pro Val Asn Thr Asn
                645                 650                 655
```

<210> SEQ ID NO 13
<211> LENGTH: 1636
<212> TYPE: DNA
<213> ORGANISM: Reticulitermes flavipes
<220> FEATURE:
<221> NAME/KEY: misc_feature
<223> OTHER INFORMATION: nucleotide sequence of Laccase Lacc-13

<400> SEQUENCE: 13

```
ctaatacgac tcactatagg gcaagcagtg gtatcaacgc agagtacgcg gggatataac     60
caacaacatg gcagggagga ctactagcat ccactggcat ggggtatttc agaaagggtc    120
ccagtacatg gacggagttc ccatggtaac ccagtgcact atacatgagg gtgacacatt    180
ccggtacgac tttatcgcta caacgagggg aactcatttc tggcattccc atgacggttt    240
gcagaagctc gatggcgtga caggtaactt ggtggttagg gtgcctaaaa atttcgaccc    300
gaacggacaa ctgtacgatt tcgatctacc agaacacaaa atttcatca gcgactggct    360 acatctttcc gcagatgacc actttcccgg actccgagcg acaaatccag gacaagatgc    420
taactccttt ctcattaacg gcagaggacg taccttgatt ggaactcagt ccaccaacac    480
accgtatgcg cagataaatg tgcagtgggg caggaggtac cggcttcgca ttgtgggctc    540
cctgtgcact gtgtgcccca cacagctcac cattgacggg cacaaaatta cagtcatagc    600
cactgacggc aattctgtgg ctcctgccag agtcgactcc ctcatcattt actctggtga    660
aagatacgac gtcgtgttag aagccactaa tacggaagga tcttactgga tccatctaaa    720
aggcctcgcc acttgtgttg gaagtagagt ttaccagctg gggtgttgc aatatgaaaa    780
```

-continued

```
tacaacaacc aataaactgc atgctctgac acctgatcca ggttacgacg gattcccgca      840
accagcaagc taccgggtcc tgaacccaga gaacgcaagc tgtagcatcg gctcgacagg      900
cctatgcgtc acgcaactcg cgaactcgga ccccgtgcca cgggacatcc taacccagct      960
cccggacatc aactatcttc tccaatttgg atttgaaact ttcgactcca gaagtttctt     1020
caaagcttac gacagatatt ttgtcagcgc ctttctcgag ttactcagca gtaccgtcaa     1080
caacatttct ttcgtttcgc ccccatctcc gctcctctca caaggggggg atgtaccaga     1140
cgacatccta tgcccgacgg gggctgatgg cctgccccag tgtcccggag gaaactccta     1200
ctgcacatgt gtccatgtca tcaaaatcaa actgggtgct ttggtgcaga tcatcctgtc     1260
ggaccagtca cccaaatccg acctgaacca tccgttccat atacacggac atgcgtttta     1320
cgtcctgggc atggggcaat acgctgcagg acagacagcg caggacctcc ttaactcctt     1380
gaagagtaac gtgagtagtg tgtcccctgc gccggttctt aaagataccg tcgcagttcc     1440
atctggcggc tacgcgatca tcaagttcag accaaaaaac cctggttact ggttccttca     1500
ctgccacttc ctgtaccatg tagcgaccgg gatgagtgtt gtgctccagg tgggagaaac     1560
aagtgactat cccctacac cagacggctt ccccaagtgt ggaagcttca cacctcccgt      1620
gaacaccaac tgaagt                                                     1636
```

<210> SEQ ID NO 14
<211> LENGTH: 2070
<212> TYPE: DNA
<213> ORGANISM: Reticulitermes flavipes
<220> FEATURE:
<221> NAME/KEY: misc_feature
<223> OTHER INFORMATION: nucleotide sequence of Laccase Lacc-14

<400> SEQUENCE: 14

```
ctaatacgac tcactatagg gcaagcagtg gtatcaacgc agagtacgcg ggaagcagtg       60
gtatcaacgc agagtacgcg gggaccaaag ttgctgtaag tttacagatc ggacgcctac      120
attatgttgc cttgcgtcct gcttgcttgc gcaattggtg tggcttctgc aacatcagtg      180
ctcctgaatt catacctcca gcccaacgat gacattgatc gaaacacgta cctcctaaat      240
gcaaaaagca caactgtgc ccgtatatgc aatgggacag aggcgcccaa aatctgctac       300
taccaatgga caattgagaa ctacgtgact ctgtcagaag cgtgtgacaa ttgtcccttg      360
aatgtgacgg cctgttacaa cgcacagtgc atcacagctg atggatatga gcgcagtatc     420
ctttcggtaa acaggaaact accggggcct tccatcgagg tgtgcctcag agacagagta      480
attgtggata taaccaacaa catggcaggg aggactacta gcatccactg gcatggggta      540
tttcagaaag ggtcccagta catggacgga gttcccatgg taacccagtg cactatacat      600
gagggtgaca cattccggta cgactttatc gctaacaacg agggaactca tttctggcat     660
tcccatgacg gtttgcagaa gctcgatggc gtgacaggta acttggtggt tagggtgcct     720
aaaaatttcg acccgaacgg acaactgtac gatttcgatc taccagaaca caaaattttc      780
atcagcgact ggctacatct ttccgcagat gaccactttc ccggactccg agcgacaaat     840
ccaggacaag atgctaactc ctttctcatt aacggcagag gacgtacctt gattggaact     900
cagtccacca acacaccgta tgcgcagata aatgtgcagt gggcaggag gtaccggctt      960 cgcattgtgg gctccctgtg cactgtgtgc cccacacagc tcaccattga cgggcacaaa    1020
attacagtca tagccattga cggcaattct gtggctcctg ccagagtcga ctccctcatc    1080
atttactctg gtgaaagata cgacgtcgtg ttagaagcca ctaatacgga aggatcttac    1140
```

-continued

```
tggatccatc taaaaggcct cgtcacttgt gttggaagca gagtttacca gctgggggtg    1200
ttgcaatatg aaaatacaac aaccaataaa ctgcatgctc tgacacctga tccaggttac    1260
gacggattcc cgcaaccagc aagctaccgg gtcctgaacc cagagaacgc aagctgtagc    1320
atcggctcga caggcctatg cgtcacgcaa ctcgcgaact cggaccccgt gccacgggac    1380
atcctaaccc agctcccgga catcaactat cttctccaat ttggatttaa aattttcgac    1440
tccagaagtt tcttcaaagc ttacgacaga tattttgtca gcccctttct cgacttagtc    1500
agcagtaccg tcaacaacat ttcttccgtt tcgcccccat ctccgctcct ctcacaaagg    1560
ggggatgtac cagacgacat cctatgcccg acggggctg atggcctgcc ccagtgtccc     1620
ggaggaaact cctactgcac atgtgtccat gtcatcaaaa tcaaactggg tgctttggtg    1680
cagatcatcc tgtcggacca gacacccaaa tccggcctga ccatccgtt ccatctacac     1740 ggacatgcgt tttacgtcct gggcatgggg caatacgctg caggacagac agcgcaggac    1800
ctccttaact ccttgaagag taacgtgagt agtgtgtccc ctgcgccggt tcttaaagat    1860
accatcgcag ttccatctgg cggctacgcg atcatcaagt tcagaccaaa aaatcctggt    1920
tactggttcc ttcactgcca cttcctgtac catgtagcga ccgggatgag tgttgtgctc    1980
caggtgggag aaacaagtga ctatcccct acaccagacg gcttcccaa gtgtggaagc      2040 ttcacacctc ccgtgaacac caactgaagt                                     2070
```

<210> SEQ ID NO 15
<211> LENGTH: 537
<212> TYPE: PRT
<213> ORGANISM: Reticulitermes flavipes
<220> FEATURE:
<221> NAME/KEY: misc_feature
<223> OTHER INFORMATION: amino acid sequence Laccase Lacc-14

<400> SEQUENCE: 15

```
Gly Lys Gln Trp Tyr Gln Arg Arg Val Arg Gly Asp Ile Thr Asn Asn
 1               5                  10                  15

Met Ala Gly Arg Thr Thr Ser Ile His Trp His Gly Val Phe Gln Lys
             20                  25                  30

Gly Ser Gln Tyr Met Asp Gly Val Pro Met Val Thr Gln Cys Thr Ile
         35                  40                  45

His Glu Gly Asp Thr Phe Arg Tyr Asp Phe Ile Ala Asn Asn Glu Gly
     50                  55                  60

Thr His Phe Trp His Ser His Asp Gly Leu Gln Lys Leu Asp Gly Val
 65                  70                  75                  80

Thr Gly Asn Leu Val Val Arg Val Pro Lys Asn Phe Asp Pro Asn Gly
                 85                  90                  95

Gln Leu Tyr Asp Phe Asp Leu Pro Glu His Lys Ile Phe Ile Ser Asp
            100                 105                 110

Trp Leu His Leu Ser Ala Asp Asp His Phe Pro Gly Leu Arg Ala Thr
        115                 120                 125

Asn Pro Gly Gln Asp Ala Asn Ser Phe Leu Ile Asn Gly Arg Gly Arg
    130                 135                 140

Thr Leu Ile Gly Thr Gln Ser Thr Asn Thr Pro Tyr Ala Gln Ile Asn
145                 150                 155                 160

Val Gln Trp Gly Arg Arg Tyr Arg Leu Arg Ile Val Gly Ser Leu Cys
                165                 170                 175

Thr Val Cys Pro Thr Gln Leu Thr Ile Asp Gly His Lys Ile Thr Val
            180                 185                 190

Ile Ala Thr Asp Gly Asn Ser Val Ala Pro Ala Arg Val Asp Ser Leu
```

```
                 195                 200                 205
Ile Ile Tyr Ser Gly Glu Arg Tyr Asp Val Val Leu Glu Ala Thr Asn
210                 215                 220

Thr Glu Gly Ser Tyr Trp Ile His Leu Lys Gly Leu Ala Thr Cys Val
225                 230                 235                 240

Gly Ser Arg Val Tyr Gln Leu Gly Val Leu Gln Tyr Glu Asn Thr Thr
                245                 250                 255

Thr Asn Lys Leu His Ala Leu Thr Pro Asp Pro Gly Tyr Asp Gly Phe
            260                 265                 270

Pro Gln Pro Ala Ser Tyr Arg Val Leu Asn Pro Glu Asn Ala Ser Cys
        275                 280                 285

Ser Ile Gly Ser Thr Gly Leu Cys Val Thr Gln Leu Ala Asn Ser Asp
    290                 295                 300

Pro Val Pro Arg Asp Ile Leu Thr Gln Leu Pro Asp Ile Asn Tyr Leu
305                 310                 315                 320

Leu Gln Phe Gly Phe Glu Thr Phe Asp Ser Arg Ser Phe Phe Lys Ala
                325                 330                 335

Tyr Asp Arg Tyr Phe Val Ser Ala Phe Leu Glu Leu Leu Ser Ser Thr
            340                 345                 350

Val Asn Asn Ile Ser Phe Val Ser Pro Pro Ser Pro Leu Leu Ser Gln
        355                 360                 365

Arg Gly Asp Val Pro Asp Asp Ile Leu Cys Pro Thr Gly Ala Asp Gly
    370                 375                 380

Leu Pro Gln Cys Pro Gly Gly Asn Ser Tyr Cys Thr Cys Val His Val
385                 390                 395                 400

Ile Lys Ile Lys Leu Gly Ala Leu Val Gln Ile Ile Leu Ser Asp Gln
                405                 410                 415

Ser Pro Lys Ser Asp Leu Asn His Pro Phe His Ile His Gly His Ala
            420                 425                 430

Phe Tyr Val Leu Gly Met Gly Gln Tyr Ala Ala Gly Gln Thr Ala Gln
        435                 440                 445

Asp Leu Leu Asn Ser Leu Lys Ser Asn Val Ser Ser Val Ser Pro Ala
    450                 455                 460

Pro Val Leu Lys Asp Thr Val Ala Val Pro Ser Gly Gly Tyr Ala Ile
465                 470                 475                 480

Ile Lys Phe Arg Pro Lys Asn Pro Gly Tyr Trp Phe Leu His Cys His
                485                 490                 495

Phe Leu Tyr His Val Ala Thr Gly Met Ser Val Val Leu Gln Val Gly
            500                 505                 510

Glu Thr Ser Asp Tyr Pro Pro Thr Pro Asp Gly Phe Pro Lys Cys Gly
        515                 520                 525

Ser Phe Thr Pro Pro Val Asn Thr Asn
    530                 535
```

<210> SEQ ID NO 16
<211> LENGTH: 2113
<212> TYPE: DNA
<213> ORGANISM: Reticulitermes flavipes
<220> FEATURE:
<221> NAME/KEY: misc_feature
<223> OTHER INFORMATION: nucleotide sequence of Laccase Lacc-16

<400> SEQUENCE: 16
acttcagttg gtttcacggg aggctaatac gactcactat agggcaagca gtggtatcaa    60
cgcagagtac gcggggatat acggccctat cagttgtgta ataactttcg gttaaggttt   120

```
tcattaccaa agttgctgta agtttacaga tcggacgcct acattatgtt gccttgtgtc    180
ctgcttgctt gcgcaattgg tgtggcttct gcaacatcag tgctcctgaa ttcatacctt    240
cagcccaacg atgacattga tcgaaacacg tacctcctaa atgcaaaaag caacaactgt    300
gcccgtatat gcaatgggac agaggcgccc aaaatctgct actaccaatg gacaattgag    360
aactacgtga ctctgtcaga agcgtgtgac aattgtccct gaatgtgac ggcctgttac     420
aacgcacagt gcatcacagc tgatggatat gagcgcagta tcctttcggt aaacaggaaa    480
ctaccggggc cttccatcga ggtgtgcctc agagacagag taattgtgga tataaccaac    540
aacatggcag ggaggactac tagcatccac tggcatgggg tatttcagaa agggtcccag    600
tacatggacg gagttcccat ggtaacccag tgcactatac atgagggtga cacattccgg    660
tacgacttta tcgctaacaa cgagggaact catttctggc attcccatga cggtttgcag    720
aagctcgatg gcgtgacagg taacttggtg gttagggtgc ctaaaaattt cgacccgaac    780
ggacaactgt acgatttcga tctaccagaa cacaaaattt tcatcagcga ctggctacat    840
ctttccgcag atgaccactt tcccggactc cgagcgacaa tccaggaca agatgctaac     900
tcctttctca ttaacggcag aggacgtacc ttgattggaa ctcagtccac caacacaccg    960
tatgcgcaga taaatgtgca gtggggcagg aggtaccggc ttcgcattgt gggctccctg   1020
tgcactgtgt gccccacaca gctcaccatt gacgggcaca aaattacagt catagccact   1080
gacggcaatt ctgtggctcc tgccagagtc gactccctca tcatttactc tggtgaaaga   1140
tacgacgtcg tgttagaagc cactaatacg gaaggatctt actggatcca tctaaaaggc   1200
ctcgtcactt gtgttggaag cagagtttac cagctggggg tgttgcaata tgaaaataca   1260
acaaccaata aactgcatgc tctgacacct gatccaggtt acgacggatt cccgcaacca   1320
gcaagctacc gggtcctgaa cccagagaac gcaagctgta gcatcggctc gacaggccta   1380
tgcgtcatgc aactcgcgaa ctcggacccc gtgccacggg acatcctaac ccagctcccg   1440
gacatcaact atcttctcca atttggattt aaaattttcg actccagaag tttcttcaaa   1500
gcttacgaca gatattttgt cagccccttt ctcgacttag tcagcagtac cgtcaacaac   1560
atttcttccg tttcgccccc atctccgctc ctctcacaaa gggggatgt accagacgac    1620
atcctatgcc cgacgggggc tgatggcctg ccccagtgtc ccggaggaaa ctcctactgc   1680
acatgtgtcc atgtcatcaa aatcaaactg gtgctttgg tgcagatcat cctgtcggac    1740
cagacaccca atccggcct gaaccatccg ttccatctac acggacatgc gttttacgtc    1800
ctgggcatgg gcaatacgc tgcaggacag acagcgcagg acctccttaa ctccttgaag    1860
agtaacgtga gtagtgtgtc ccctgcgccg gttcttaaag ataccatcgc agttccatct   1920
ggcggctacg cgatcatcaa gttcagacca aaaaaatcct ggttactggt tccttcactg   1980
ccacttcctg taccatgtag cgaccgggat gagtgttgtg ctccaggtgg gagaaacaag   2040
tgactatccc cctacaccag acggcttccc caagtgtgga agcttcacac ctcccgtgaa   2100
caccaactga agt                                                     2113
```

<210> SEQ ID NO 17
<211> LENGTH: 655
<212> TYPE: PRT
<213> ORGANISM: Reticulitermes flavipes
<220> FEATURE:
<221> NAME/KEY: misc_feature
<223> OTHER INFORMATION: amino acid sequence Laccase Lacc-15

<400> SEQUENCE: 17

Val Tyr Arg Ser Asp Ala Tyr Ile Met Leu Pro Cys Val Leu Leu Ala

```
            1               5                   10                  15
Cys Ala Ile Gly Val Ala Ser Ala Thr Ser Val Leu Leu Asn Ser Tyr
                20                  25                  30

Leu Gln Pro Asn Asp Asp Ile Asp Arg Asn Thr Tyr Leu Leu Asn Ala
                35                  40                  45

Lys Ser Asn Asn Cys Ala Arg Ile Cys Asn Gly Thr Glu Ala Pro Lys
             50                 55                  60

Ile Cys Tyr Tyr Gln Trp Thr Ile Glu Asn Tyr Val Thr Leu Ser Glu
 65                  70                  75                  80

Ala Cys Asp Asn Cys Pro Leu Asn Val Thr Ala Cys Tyr Asn Ala Gln
                    85                  90                  95

Cys Ile Thr Ala Asp Gly Tyr Glu Arg Ser Ile Leu Ser Val Asn Arg
                100                 105                 110

Lys Leu Pro Gly Pro Ser Ile Glu Val Cys Leu Arg Asp Arg Val Ile
            115                 120                 125

Val Asp Ile Thr Asn Asn Met Ala Gly Arg Thr Thr Ser Ile His Trp
            130                 135                 140

His Gly Val Phe Gln Lys Gly Ser Gln Tyr Met Asp Gly Val Pro Met
145                 150                 155                 160

Val Thr Gln Cys Thr Ile His Glu Gly Asp Thr Phe Arg Tyr Asp Phe
                165                 170                 175

Ile Ala Asn Asn Glu Gly Thr His Phe Trp His Ser His Asp Gly Leu
                180                 185                 190

Gln Lys Leu Asp Gly Val Thr Gly Asn Leu Val Val Arg Val Pro Lys
            195                 200                 205

Asn Phe Asp Pro Asn Gly Gln Leu Tyr Asp Phe Asp Leu Pro Glu His
            210                 215                 220

Lys Ile Phe Ile Ser Asp Trp Leu His Leu Ser Ala Asp Asp His Phe
225                 230                 235                 240

Pro Gly Leu Arg Ala Thr Asn Pro Gly Gln Asp Ala Asn Ser Phe Leu
                245                 250                 255

Ile Asn Gly Arg Gly Arg Thr Leu Ile Gly Thr Gln Ser Thr Asn Thr
                260                 265                 270

Pro Tyr Ala Gln Ile Asn Val Gln Trp Gly Arg Arg Tyr Arg Leu Arg
            275                 280                 285

Ile Val Gly Ser Leu Cys Thr Val Cys Pro Thr Gln Leu Thr Ile Asp
            290                 295                 300

Gly His Lys Ile Thr Val Ile Ala Ile Asp Gly Asn Ser Val Ala Pro
305                 310                 315                 320

Ala Arg Val Asp Ser Leu Ile Ile Tyr Ser Gly Glu Arg Tyr Asp Val
                325                 330                 335

Val Leu Glu Ala Thr Asn Thr Glu Gly Ser Tyr Trp Ile His Leu Lys
                340                 345                 350

Gly Leu Val Thr Cys Val Gly Ser Arg Val Tyr Gln Leu Gly Val Leu
                355                 360                 365

Gln Tyr Glu Asn Thr Thr Thr Asn Lys Leu His Ala Leu Thr Pro Asp
            370                 375                 380

Pro Gly Tyr Asp Gly Phe Pro Gln Pro Ala Ser Tyr Arg Val Leu Asn
385                 390                 395                 400

Pro Glu Asn Ala Ser Cys Ser Ile Gly Ser Thr Gly Leu Cys Val Thr
                    405                 410                 415

Gln Leu Ala Asn Ser Asp Pro Val Pro Arg Asp Ile Leu Thr Gln Leu
                420                 425                 430
```

```
Pro Asp Ile Asn Tyr Leu Leu Gln Phe Gly Phe Lys Ile Phe Asp Ser
        435                 440                 445

Arg Ser Phe Phe Lys Ala Tyr Asp Arg Tyr Phe Val Ser Pro Phe Leu
    450                 455                 460

Asp Leu Val Ser Thr Val Asn Asn Ile Ser Ser Val Ser Pro Pro
465                 470                 475                 480

Ser Pro Leu Leu Ser Gln Arg Gly Asp Val Pro Asp Asp Ile Leu Cys
                485                 490                 495

Pro Thr Gly Ala Asp Gly Leu Pro Gln Cys Pro Gly Gly Asn Ser Tyr
            500                 505                 510

Cys Thr Cys Val His Val Ile Lys Ile Lys Leu Gly Ala Leu Val Gln
        515                 520                 525

Ile Ile Leu Ser Asp Gln Thr Pro Lys Ser Gly Leu Asn His Pro Phe
530                 535                 540

His Leu His Gly His Ala Phe Tyr Val Leu Gly Met Gly Gln Tyr Ala
545                 550                 555                 560

Ala Gly Gln Thr Ala Gln Asp Leu Leu Asn Ser Leu Lys Ser Asn Val
                565                 570                 575

Ser Ser Val Ser Pro Ala Pro Val Leu Lys Asp Thr Ile Ala Val Pro
            580                 585                 590

Ser Gly Gly Tyr Ala Ile Ile Lys Phe Arg Pro Lys Asn Pro Gly Tyr
        595                 600                 605

Trp Phe Leu His Cys His Phe Leu Tyr His Val Ala Thr Gly Met Ser
    610                 615                 620

Val Val Leu Gln Val Gly Glu Thr Ser Asp Tyr Pro Pro Thr Pro Asp
625                 630                 635                 640

Gly Phe Pro Lys Cys Gly Ser Phe Thr Pro Pro Val Asn Thr Asn
                645                 650                 655

<210> SEQ ID NO 18
<211> LENGTH: 2092
<212> TYPE: DNA
<213> ORGANISM: Reticulitermes flavipes
<220> FEATURE:
<221> NAME/KEY: misc_feature
<223> OTHER INFORMATION: nucleotide sequence of Laccase Lacc-17

<400> SEQUENCE: 18
ctaatacgac tcactatagg gcaagcagtg gtatcaacgc agagttacgc gggattcata    60
cggccctatc agttgtgtaa ataactttcg ttaaggtttt cattaccaaa gttgctgtaa   120
gtttacagat cggacgccta cattatgttg ccttgcgtcc tgcttgcttg cgcaattggt   180
gtggcttctg caacatcagt gctcctgaat tcataccttc agcccaacga tgacattgat   240
cgaaacacgt acctcctaaa tgcaaaaagc aacaactgtg cccgtatatg caatgggaca   300
gaggcgccca aaatctgcta ctaccaatgg acaattgaga actacgtgac tctgtcagaa   360
gcgtgtgaca attgtccctt gaatgtgacg gcctgttaca acgcacagtg catcacagct   420
gatggatatg agcgcagtat cctttcggta aacaggaaac taccggggcc ttccatcgag   480
gtgtgcctca gagacagagt aattgtggat ataaccaaca catggcagg gaggactact   540 agcatccact ggcatggggt atttcagaaa gggtcccagt acatggacgg agttcccatg   600
gtaacccagt gcactataca tgagggtgac acattccggt acgactttat cgctaacaac   660
gagggaactc atttctggca ttcccatgac ggtttgcaga agctcgatgg cgtgacaggt   720
aacttggtgg ttagggtgcc taaaaatttc gacccgaacg acaactgta cgatttcgat   780 ctaccagaac acaaaatttt catcagcgac tggctacatc tttccgcaga tgaccacttt   840
```

```
cccggactcc gagcgacaaa tccaggacaa gatgctaact cctttctcat taacggcaga      900
ggacgtacct tgattggaac tcagtccacc aacacaccgt atgcgcagat aaatgtgcag      960
tggggcagga ggtaccggct tcgcattgtg ggctccctgt gcactgtgtg ccccacacag     1020
ctcaccattg acgggcacaa aattacagtc atagccactg acggcaattc tgtggctcct     1080
gccagagtcg actccctcat catttactct ggtgaaagat acgacgtcgt gttagaagcc     1140
actaatacgg aaggatctta ctggatccat ctaaaaggcc tcgtcacttg tgttggaagc     1200
agagtttacc agctggggggt gttgcaatat gaaaatacaa caaccaataa actgcatgct     1260
ctgacacctg atccaggtta cgacggattc ccgcaaccag caagctaccg ggtcctgaac     1320
ccagagaacg caagctgtag catcggctcg acaggcctat gcgtcacgca actcgcgaac     1380
tcggaccccg tgccacggga catcctaacc cagctcccgg acatcaacta tcttctccaa     1440
tttggattta aaattttcga ctccagaagt ttcttcaaag cttacgacag atattttgtc     1500
agccccttc tcgacttagt cagcagtacc gtcaacaaca tttcttccgt ttcgccccca     1560
tctccgctcc tctcacaaag gggggatgta ccagacgaca tcctatgccc gacgggggct     1620
gatgcctgc cccagtgtcc cggaggaaac tcctactgca catgtgtcca tgtcatcaaa     1680
atcaaactgg gtgctttggt gcagatcatc ctgtcggacc agacacccaa tccggcctg     1740
aaccatccgt tccatctaca cggacatgcg ttttacgtcc tgggcatggg gcaatacgct     1800
gcaggacaga cagcgcagga cctccttaac tccttgaaga gtaacgtgag tagtgtgtcc     1860
cctgcgccgg ttcttaaaga taccatcgca gttccatctg gcggctacgc gatcatcaag     1920
ttcagaccaa aaaaatcctg gttactggct ccttcactgc cacttcctgt accatgtagc     1980
gaccgggatg agtgttgtgc tctaggtggg agaaacaagt gactatcccc ctacaccaga     2040
cggcttcccc aagtgtggaa gcttcacacc tcccgtgaac accaactgaa gt              2092
```

<210> SEQ ID NO 19
<211> LENGTH: 633
<212> TYPE: PRT
<213> ORGANISM: Reticulitermes flavipes
<220> FEATURE:
<221> NAME/KEY: misc_feature
<223> OTHER INFORMATION: amino acid sequence Laccase Lacc-17

<400> SEQUENCE: 19

```
Val Tyr Arg Ser Asp Ala Tyr Ile Met Leu Pro Cys Val Leu Leu Ala
1               5                   10                  15

Cys Ala Ile Gly Val Ala Ser Ala Thr Ser Val Leu Leu Asn Ser Tyr
            20                  25                  30

Leu Gln Pro Asn Asp Asp Ile Asp Arg Asn Thr Tyr Leu Leu Asn Ala
        35                  40                  45

Lys Ser Asn Asn Cys Ala Arg Ile Cys Asn Gly Thr Glu Ala Pro Lys
    50                  55                  60

Ile Cys Tyr Tyr Gln Trp Thr Ile Glu Asn Tyr Val Thr Leu Ser Glu
65                  70                  75                  80

Ala Cys Asp Asn Cys Pro Leu Asn Val Thr Ala Cys Tyr Asn Ala Gln
                85                  90                  95

Cys Ile Thr Ala Asp Gly Tyr Glu Arg Ser Ile Leu Ser Val Asn Arg
            100                 105                 110

Lys Leu Pro Gly Pro Ser Ile Glu Val Cys Leu Arg Asp Arg Val Ile
        115                 120                 125

Val Asp Ile Thr Asn Asn Met Ala Gly Arg Thr Thr Ser Ile His Trp
    130                 135                 140
```

-continued

His Gly Val Phe Gln Lys Gly Ser Gln Tyr Met Asp Gly Val Pro Met
145                 150                 155                 160

Val Thr Gln Cys Thr Ile His Glu Gly Asp Thr Phe Arg Tyr Asp Phe
            165                 170                 175

Ile Ala Asn Asn Glu Gly Thr His Phe Trp His Ser His Asp Gly Leu
            180                 185                 190

Gln Lys Leu Asp Gly Val Thr Gly Asn Leu Val Val Arg Val Pro Lys
            195                 200                 205

Asn Phe Asp Pro Asn Gly Gln Leu Tyr Asp Phe Asp Leu Pro Glu His
            210                 215                 220

Lys Ile Phe Ile Ser Asp Trp Leu His Leu Ser Ala Asp Asp His Phe
225                 230                 235                 240

Pro Gly Leu Arg Ala Thr Asn Pro Gly Gln Asp Ala Asn Ser Phe Leu
            245                 250                 255

Ile Asn Gly Arg Gly Arg Thr Leu Ile Gly Thr Gln Ser Thr Asn Thr
            260                 265                 270

Pro Tyr Ala Gln Ile Asn Val Gln Trp Gly Arg Arg Tyr Arg Leu Arg
            275                 280                 285

Ile Val Gly Ser Leu Cys Thr Val Cys Pro Thr Gln Leu Thr Ile Asp
290                 295                 300

Gly His Lys Ile Thr Val Ile Ala Thr Asp Gly Asn Ser Val Ala Pro
305                 310                 315                 320

Ala Arg Val Asp Ser Leu Ile Ile Tyr Ser Gly Glu Arg Tyr Asp Val
            325                 330                 335

Val Leu Glu Ala Thr Asn Thr Glu Gly Ser Tyr Trp Ile His Leu Lys
            340                 345                 350

Gly Leu Val Thr Cys Val Gly Ser Arg Val Tyr Gln Leu Gly Val Leu
            355                 360                 365

Gln Tyr Glu Asn Thr Thr Thr Asn Lys Leu His Ala Leu Thr Pro Asp
370                 375                 380

Pro Gly Tyr Asp Gly Phe Pro Gln Pro Ala Ser Tyr Arg Val Leu Asn
385                 390                 395                 400

Pro Glu Asn Ala Ser Cys Ser Ile Gly Ser Thr Gly Leu Cys Val Met
            405                 410                 415

Gln Leu Ala Asn Ser Asp Pro Val Pro Arg Asp Ile Leu Thr Gln Leu
            420                 425                 430

Pro Asp Ile Asn Tyr Leu Leu Gln Phe Gly Phe Lys Ile Phe Asp Ser
            435                 440                 445

Arg Ser Phe Phe Lys Ala Tyr Asp Arg Tyr Phe Val Ser Pro Phe Leu
            450                 455                 460

Asp Leu Val Ser Ser Thr Val Asn Asn Ile Ser Ser Val Ser Pro Pro
465                 470                 475                 480

Ser Pro Leu Leu Ser Gln Arg Gly Asp Val Pro Asp Asp Ile Leu Cys
            485                 490                 495

Pro Thr Gly Ala Asp Gly Leu Pro Gln Cys Pro Gly Gly Asn Ser Tyr
            500                 505                 510

Cys Thr Cys Val His Val Ile Lys Ile Lys Leu Gly Ala Leu Val Gln
            515                 520                 525

Ile Ile Leu Ser Asp Gln Thr Pro Lys Ser Gly Leu Asn His Pro Phe
            530                 535                 540

His Leu His Gly His Ala Phe Tyr Val Leu Gly Met Gly Gln Tyr Ala
545                 550                 555                 560

Ala Gly Gln Thr Ala Gln Asp Leu Leu Asn Ser Leu Lys Ser Asn Val

```
                565              570              575
Ser Ser Val Ser Pro Ala Pro Val Leu Lys Asp Thr Ile Ala Val Pro
                    580              585              590

Ser Gly Gly Tyr Ala Ile Ile Lys Phe Arg Pro Lys Lys Ser Trp Leu
            595              600              605

Leu Val Pro Ser Leu Pro Leu Pro Val Pro Cys Ser Asp Arg Asp Glu
        610              615              620

Cys Cys Ala Pro Gly Gly Arg Asn Lys
625                 630

<210> SEQ ID NO 20
<211> LENGTH: 2038
<212> TYPE: DNA
<213> ORGANISM: Reticulitermes flavipes
<220> FEATURE:
<221> NAME/KEY: misc_feature
<223> OTHER INFORMATION: nucleotide sequence of Laccase Lacc-19

<400> SEQUENCE: 20
ctaatacgac tcactatagg gcaagcagtg gtatcaacgc agagtacgcg gggatacggc      60
cctatcagtt tacagatcgg acgcctacat tatgttgcct tgcgtcctgc ttgcttgcgc     120
aattggtgtg gcttctgcaa catcagtgct cctgaattca taccctcagc caacgatga     180 cattgatcga aacacgtacc tcctaaatgc aaaaagcaac aactgtgccc gtatatgcaa     240
tgggacagag gcgcccaaaa tctgctacta ccaatggaca attgagaact acgtgactct     300
gtcagaagcg tgtgacaatt gtcccttgaa tgtgacggcc tgttacaacg cacagtgcat     360
cacagctgat ggatatgagc gcagtatcct ttcggtaaac aggaaactac cggggccttc     420
catcgaggtg tgcctcagag acagagtaat tgtggatata accaacaaca tggcagggag     480
gactactagc atccactggc atgggtatt tcagaaaggg tcccagtaca tggacggagt     540
tcccatggta acccagtgca ctatacatga gggtgcacac ttccggtacg actttatcgc     600
taacaacgag ggaactcatt tctggcattc ccatgacggt ttgcagaagc tcgatggcgt     660
gacaggtaac ttggtggtta gggtgcctaa aaatttcgac ccgaacggac aactgtacga     720
tttcgatcta ccagaacaca aaattttcat cagcgactgg ctacatcttt ccgcagatga     780
ccactttccc ggactccgag cgacaaatcc aggacaagat gctaactcct ttctcattaa     840
cggcagagga cgtaccttga ttggaactca gtccaccaac acaccgtatg cgcagataaa     900
tgtgcagtgg ggcaggaggt accggcttcg cattgtgggc tccctgtgca ctgtgtgccc     960
cacacagctc accattgacg ggcacaaaat tacagtcata gccactgacg gcaattctgt    1020
ggctcctgcc agagtcgact ccctcatcat ttactctggt gaaagatacg acgtcgtgtt    1080
agaagccact aatacggaag gatcttactg gatccatcta aaaggcctcg ccacttgtgt    1140
tggaagtaga gtttaccagc tgggggtgtt gcaatatgaa aatacaacaa ccaataaact    1200
gcatgctctg acacctgatc caggttacga cggattcccg caaccagcaa gctaccgggt    1260
cctgaaccca gagaacgcaa gctgtagcat cggctcgaca ggcctatgcg tcacgcaact    1320
cgcgaactcg gaccccgtgc cacgggacat cctaacccag ctcccggaca tcaactatct    1380
tctccaattt ggatttgaaa ctttcgactc cagaagtttc ttcaaagctt acgacagata    1440
ttttgtcagc ccctttctcg agttactcag cagtaccgtc aacaacattt ctttcgtttc    1500
gcccccatct ccgctcctct cacaaagggg ggatgtacca gacgacatcc tatgcccgac    1560
gggggctgat ggcctgcccc agtgtcccgg aggaaactcc tactgcacat gtgtccatgt    1620
catcaaaatc aaactgggtg ctttggtgca gatcatcctg tcggaccagt cacccaaatc    1680
```

```
cgacctgaac catccgttcc atatacacgg acatgcgttt tacgtcctgg gcatggggca   1740
atacgctgca ggacagacag cgcaggacct ccttaactcc ttgaagagta acgtgagtag   1800
tgtgtcccct gcgccggttc ttaaagatac cgtcgcagtt ccatctggcg gctacgcgat   1860
catcaagttc agaccaaaaa accctggtta ctggttcctt cactgccact tcctgtacca   1920
tgtagcgacc gggatgagtg ttgtgctcca ggtgggagaa acaagtgact atccccctac   1980
accagacggc ttccccaagt gtggaagctt cacacctccc gtgaacacca actgaagt    2038
```

<210> SEQ ID NO 21
<211> LENGTH: 633
<212> TYPE: PRT
<213> ORGANISM: Reticulitermes flavipes
<220> FEATURE:
<221> NAME/KEY: misc_feature
<223> OTHER INFORMATION: amino acid sequence Laccase Lacc-19

<400> SEQUENCE: 21

```
Val Tyr Arg Ser Asp Ala Tyr Ile Met Leu Pro Cys Val Leu Leu Ala
1               5                   10                  15

Cys Ala Ile Gly Val Ala Ser Ala Thr Ser Val Leu Leu Asn Ser Tyr
            20                  25                  30

Leu Gln Pro Asn Asp Asp Ile Asp Arg Asn Thr Tyr Leu Leu Asn Ala
        35                  40                  45

Lys Ser Asn Asn Cys Ala Arg Ile Cys Asn Gly Thr Glu Ala Pro Lys
    50                  55                  60

Ile Cys Tyr Tyr Gln Trp Thr Ile Glu Asn Tyr Val Thr Leu Ser Glu
65                  70                  75                  80

Ala Cys Asp Asn Cys Pro Leu Asn Val Thr Ala Cys Tyr Asn Ala Gln
                85                  90                  95

Cys Ile Thr Ala Asp Gly Tyr Glu Arg Ser Ile Leu Ser Val Asn Arg
            100                 105                 110

Lys Leu Pro Gly Pro Ser Ile Glu Val Cys Leu Arg Asp Arg Val Ile
        115                 120                 125

Val Asp Ile Thr Asn Asn Met Ala Gly Arg Thr Thr Ser Ile His Trp
    130                 135                 140

His Gly Val Phe Gln Lys Gly Ser Gln Tyr Met Asp Gly Val Pro Met
145                 150                 155                 160

Val Thr Gln Cys Thr Ile His Glu Gly Asp Thr Phe Arg Tyr Asp Phe
                165                 170                 175

Ile Ala Asn Asn Glu Gly Thr His Phe Trp His Ser His Asp Gly Leu
            180                 185                 190

Gln Lys Leu Asp Gly Val Thr Gly Asn Leu Val Val Arg Val Pro Lys
        195                 200                 205

Asn Phe Asp Pro Asn Gly Gln Leu Tyr Asp Phe Asp Leu Pro Glu His
    210                 215                 220

Lys Ile Phe Ile Ser Asp Trp Leu His Leu Ser Ala Asp His Phe
225                 230                 235                 240

Pro Gly Leu Arg Ala Thr Asn Pro Gly Gln Asp Ala Asn Ser Phe Leu
                245                 250                 255

Ile Asn Gly Arg Gly Arg Thr Leu Ile Gly Thr Gln Ser Thr Asn Thr
            260                 265                 270

Pro Tyr Ala Gln Ile Asn Val Gln Trp Gly Arg Arg Tyr Arg Leu Arg
        275                 280                 285

Ile Val Gly Ser Leu Cys Thr Val Cys Pro Thr Gln Leu Thr Ile Asp
    290                 295                 300
```

Gly His Lys Ile Thr Val Ile Ala Thr Asp Gly Asn Ser Val Ala Pro
305                 310                 315                 320

Ala Arg Val Asp Ser Leu Ile Ile Tyr Ser Gly Glu Arg Tyr Asp Val
            325                 330                 335

Val Leu Glu Ala Thr Asn Thr Glu Gly Ser Tyr Trp Ile His Leu Lys
            340                 345                 350

Gly Leu Val Thr Cys Val Gly Ser Arg Val Tyr Gln Leu Gly Val Leu
            355                 360                 365

Gln Tyr Glu Asn Thr Thr Thr Asn Lys Leu His Ala Leu Thr Pro Asp
370                 375                 380

Pro Gly Tyr Asp Gly Phe Pro Gln Pro Ala Ser Tyr Arg Val Leu Asn
385                 390                 395                 400

Pro Glu Asn Ala Ser Cys Ser Ile Gly Ser Thr Gly Leu Cys Val Thr
            405                 410                 415

Gln Leu Ala Asn Ser Asp Pro Val Pro Arg Asp Ile Leu Thr Gln Leu
            420                 425                 430

Pro Asp Ile Asn Tyr Leu Leu Gln Phe Gly Phe Lys Ile Phe Asp Ser
            435                 440                 445

Arg Ser Phe Phe Lys Ala Tyr Asp Arg Tyr Phe Val Ser Pro Phe Leu
450                 455                 460

Asp Leu Val Ser Ser Thr Val Asn Asn Ile Ser Ser Val Ser Pro Pro
465                 470                 475                 480

Ser Pro Leu Leu Ser Gln Arg Gly Asp Val Pro Asp Asp Ile Leu Cys
            485                 490                 495

Pro Thr Gly Ala Asp Gly Leu Pro Gln Cys Pro Gly Gly Asn Ser Tyr
            500                 505                 510

Cys Thr Cys Val His Val Ile Lys Ile Lys Leu Gly Ala Leu Val Gln
            515                 520                 525

Ile Ile Leu Ser Asp Gln Thr Pro Lys Ser Gly Leu Asn His Pro Phe
530                 535                 540

His Leu His Gly His Ala Phe Tyr Val Leu Gly Met Gly Gln Tyr Ala
545                 550                 555                 560

Ala Gly Gln Thr Ala Gln Asp Leu Leu Asn Ser Leu Lys Ser Asn Val
            565                 570                 575

Ser Ser Val Ser Pro Ala Pro Val Leu Lys Asp Thr Ile Ala Val Pro
            580                 585                 590

Ser Gly Gly Tyr Ala Ile Ile Lys Phe Arg Pro Lys Lys Ser Trp Leu
            595                 600                 605

Leu Ala Pro Ser Leu Pro Leu Pro Val Pro Cys Ser Asp Arg Asp Glu
610                 615                 620

Cys Cys Ala Leu Gly Gly Arg Asn Lys
625                 630

<210> SEQ ID NO 22
<211> LENGTH: 2015
<212> TYPE: DNA
<213> ORGANISM: Reticulitermes flavipes
<220> FEATURE:
<221> NAME/KEY: misc_feature
<223> OTHER INFORMATION: nucleotide sequence of Laccase Lacc-22

<400> SEQUENCE: 22
ctaatacgac tcactatagg gcaagcagtg gtatcaacgc agagtacgcg ggagatcgga     60
cgcctacatt atgttgcctt gcgtcctgct tgcttgcgca attggtgtgg cttctgcaac    120
atcagtgctc ctgaattcat accttcagcc caacgatgac attgatcgaa acacgtacct    180

```
cctaaatgca aaaagcaaca actgtgcccg tatatgcaat gggacagagg cgcccaaaat    240
ctgctactac caatggacaa ttgagaacta cgtgactctg tcagaagcgt gtgacaattg    300
tcccttgaat gtgacggcct gttacaacgc acagtgcatc acagctgatg gatatgagcg    360
cagtatcctt tcggtaaaca ggaaactacc ggggccttcc atcgaggtgc ctcagagaca    420
gagtaattgt ggatataacc aacaacatgg cagggaggac tgctagcatc cactggcatg    480
gggtatttca gaaagggtcc cagtacatgg acggagttcc catggtaacc cagtgcacta    540
tacatgaggg tgacacattc cggtacgact ttatcgctaa caacgaggga actcatttct    600
ggcattccca tgacggtttg cagaagctcg atggcgtgac aggtaacttg gtggttaggg    660
tgcctaaaaa tttcgacccg aacggacaac tgtacgactt cgatctacca gaacacaaaa    720
ttttcatcag cgactggcta catctttccg cagatgacca ctttcccgga ctccgagcga    780
caaatccagg acaagatgct aactcctttc tcattaacgg cagaggacgt accttgattg    840
gaactcagtc caccaacaca ccgtatgcgc agataaatgt gcagtggggc aggaggtacc    900
ggcttcgcat tgtgggctcc ctgtgcactg tgtgccccac acagctcacc attgacgggc    960
acaaaattac agtcatagcc actgacggca attctgtggc tcctgccaga gtcgactccc   1020
tcatcattta ctctggtgaa agatacgacg tcgtgttaga agccactaat acggaaggat   1080
cttactggat ccatctaaaa ggcctcgcca cttgtgttgg aagtagagtt taccagctgg   1140
gggtgttgca atatgaaaat acaacaacca ataaactgca tgctctgaca cctgatccag   1200
gttacgacgg attcccgcaa ccagcaagct acagggtcct gaacccagag aacgcaagct   1260
gtagcatcgg ctcgacaggc ctatgcgtca cgcaactcgc gaactcggac cccgtgccac   1320
gggacatcct aacccagctc ccggacatca actatcttct ccaatttgga tttgaaactt   1380
tcgactccag aagtttcttc aaagcttacg acagatattt tgtcagcccc tttctcgagt   1440
tactcagcag taccgtcaac aacatttctt tcgtttcgcc cccatctccg ctcctctcac   1500 aaaggggga tgtaccagac gacatcctat gcccgacggg ggctgatggc ctgccccagt   1560
gtcccggagg aaaactcctac tgcacatgtg tccatgtcat caaaatcaaa ctgggtgctt   1620
tggtgcagat catcctgtcg gaccagtcac ccaaatccga cctgaaccat ccgttccata   1680
tacacggaca tgcgttttac gtcctgggca tggggcaata cgctgcagga cagacagcgc   1740
aggacctcct taactccttg aagagtaacg tgagtagtgt gtcccctgcg ccggttctta   1800
aagataccgt cgcagttcca tctggcggct acgcgatcat caagttcaga ccaaaaaacc   1860
ctggttactg gttccttcac tgccacttcc tgtaccatgt agcgaccggg atgagtgttg   1920
tgctccaggt gggagaaaca agtgactatc cccctacacc agacggcttc cccaagtgtg   1980
gaagcttcac acctcccgtg aacaccaact gaagt                             2015
```

<210> SEQ ID NO 23
<211> LENGTH: 544
<212> TYPE: PRT
<213> ORGANISM: Reticulitermes flavipes
<220> FEATURE:
<221> NAME/KEY: misc_feature
<223> OTHER INFORMATION: amino acid sequence Laccase Lacc-20

<400> SEQUENCE: 23

Thr Gly Asn Tyr Arg Gly Leu Pro Ser Arg Cys Leu Arg Asp Arg Val
1               5                   10                  15

Ile Val Asp Ile Thr Asn Asn Met Ala Gly Arg Thr Ala Ser Ile His
            20                  25                  30

-continued

Trp His Gly Val Phe Gln Lys Gly Ser Gln Tyr Met Asp Gly Val Pro
         35                  40                  45

Met Val Thr Gln Cys Thr Ile His Glu Gly Asp Thr Phe Arg Tyr Asp
 50                  55                  60

Phe Ile Ala Asn Asn Glu Gly Thr His Phe Trp His Ser His Asp Gly
 65                  70                  75                  80

Leu Gln Lys Leu Asp Gly Val Thr Gly Asn Leu Val Val Arg Val Pro
             85                  90                  95

Lys Asn Phe Asp Pro Asn Gly Gln Leu Tyr Asp Phe Asp Leu Pro Glu
            100                 105                 110

His Lys Ile Phe Ile Ser Asp Trp Leu His Leu Ser Ala Asp Asp His
            115                 120                 125

Phe Pro Gly Leu Arg Ala Thr Asn Pro Gly Gln Asp Ala Asn Ser Phe
130                 135                 140

Leu Ile Asn Gly Arg Gly Arg Thr Leu Ile Gly Thr Gln Ser Thr Asn
145                 150                 155                 160

Thr Pro Tyr Ala Gln Ile Asn Val Gln Trp Gly Arg Arg Tyr Arg Leu
                165                 170                 175

Arg Ile Val Gly Ser Leu Cys Thr Val Cys Pro Thr Gln Leu Thr Ile
                180                 185                 190

Asp Gly His Lys Ile Thr Val Ile Ala Thr Asp Gly Asn Ser Val Ala
                195                 200                 205

Pro Ala Arg Val Asp Ser Leu Ile Ile Tyr Ser Gly Glu Arg Tyr Asp
210                 215                 220

Val Val Leu Glu Ala Thr Asn Thr Glu Gly Ser Tyr Trp Ile His Leu
225                 230                 235                 240

Lys Gly Leu Ala Thr Cys Val Gly Ser Arg Val Tyr Gln Leu Gly Val
                245                 250                 255

Leu Gln Tyr Glu Asn Thr Thr Thr Asn Lys Leu His Ala Leu Thr Pro
                260                 265                 270

Asp Pro Gly Tyr Asp Gly Phe Pro Gln Pro Ala Ser Tyr Arg Val Leu
                275                 280                 285

Asn Pro Glu Asn Ala Ser Cys Ser Ile Gly Ser Thr Gly Leu Cys Val
290                 295                 300

Thr Gln Leu Ala Asn Ser Asp Pro Val Pro Arg Asp Ile Leu Thr Gln
305                 310                 315                 320

Leu Pro Asp Ile Asn Tyr Leu Leu Gln Phe Gly Phe Glu Thr Phe Asp
                325                 330                 335

Ser Arg Ser Phe Phe Lys Ala Tyr Asp Arg Tyr Phe Val Ser Pro Phe
                340                 345                 350

Leu Glu Leu Leu Ser Ser Thr Val Asn Asn Ile Ser Phe Val Ser Pro
                355                 360                 365

Pro Ser Pro Leu Leu Ser Gln Arg Gly Asp Val Pro Asp Asp Ile Leu
370                 375                 380

Cys Pro Thr Gly Ala Asp Gly Leu Pro Gln Cys Pro Gly Gly Asn Ser
385                 390                 395                 400

Tyr Cys Thr Cys Val His Val Ile Lys Ile Lys Leu Gly Ala Leu Val
                405                 410                 415

Gln Ile Ile Leu Ser Asp Gln Ser Pro Lys Ser Asp Leu Asn His Pro
                420                 425                 430

Phe His Ile His Gly His Ala Phe Tyr Val Leu Gly Met Gly Gln Tyr
                435                 440                 445

Ala Ala Gly Gln Thr Ala Gln Asp Leu Leu Asn Ser Leu Lys Ser Asn
450                 455                 460

| | | | | | | | | | | | | | | | |
|---|---|---|---|---|---|---|---|---|---|---|---|---|---|---|---|
|Val|Ser|Ser|Val|Ser|Pro|Ala|Pro|Val|Leu|Lys|Asp|Thr|Val|Ala|Val|
|465| | | | |470| | | |475| | | |480| | |

Pro Ser Gly Gly Tyr Ala Ile Ile Lys Phe Arg Pro Lys Asn Pro Gly
            485                 490                 495

Tyr Trp Phe Leu His Cys His Phe Leu Tyr His Val Ala Thr Gly Met
        500                 505                 510

Ser Val Val Leu Gln Val Gly Glu Thr Ser Asp Tyr Pro Pro Thr Pro
        515                 520                 525

Asp Gly Phe Pro Lys Cys Gly Ser Phe Thr Pro Pro Val Asn Thr Asn
        530                 535                 540

<210> SEQ ID NO 24
<211> LENGTH: 1711
<212> TYPE: DNA
<213> ORGANISM: Reticulitermes flavipes
<220> FEATURE:
<221> NAME/KEY: misc_feature
<223> OTHER INFORMATION: nucleotide sequence catalase "contig 230"

<400> SEQUENCE: 24

| | | |
|---|---|---|
|gggggggcagt agttggtgtg cgtttgtgtg agcagttggt ggacgtgtga tattcgtttg|60|
|aaaatgtctt ctccggatcc agcttccgat cagttagtaa attacaagaa gaaacaaacc|120|
|gataaaacga agattgttac tggacatgga gcaccagttg ataaccgtgg ggccagttta|180|
|actgtggggc cccggggtcc catgctgtta caagatatta cgtttctaaa tgaactcgca|240|
|cactttgaca gagaacgtat cccagagaga gtggtccatg ccaaaggggc aggtgcattt|300|
|ggctactttg aagtgacaca tgacatcaca aaatattgta aggcgagtgt tttctcaaaa|360|
|attggcaaga gacgccgat tgctgtaagg ttttctacag taggtggtga gagtgggtca|420|
|gctgacacag tcagagatcc tcggggcttt gctgtgaaat tttacactga agatggcatc|480|
|tgggacctgg tgggtaacaa cacaccaatc ttctttatca gggacccatt gctgtttcct|540|
|gtatttatcc acacacagaa gagaaatcct gcaacacatc tgaaggattg tgacatgttc|600|
|tgggacttcc tctctctgcg acctgaatcc acacatcaag tcatgtttct gttttctgac|660|
|agaggcattc cagatggatt tcgtcatatg aatggttatg gctctcatac attcaaggct|720|
|ataaatgata agaacgaggc tgtatacgtg aaattccatt ataagacaaa tcagggcatc|780|
|aaaaacttac tggcacagaa agcctcagaa gtagctgtag cagaccctga ttactctatc|840|
|cgagacttgt acaatgctat cgcacgaggc cagtacccat catggacttt gtacatccaa|900|
|gtgatgactt ttgaacaagc agagaaattc aggtggaacc cctttgacct cactaaggtt|960|
|tggccgcatg cagagtatcc actaatcccc gtgggcaaac ttgtgcttga ccgcaacccc|1020|
|gccaattact tgctgaggt ggagcagatt gcattcagcc ctgcacacat ggtgcctggc|1080|
|attgaaccaa gtcctgacaa gatgttgcag ggtcggctgt tcagctactc agacacgcac|1140|
|cgtcaccgac tgggagccaa ctacctgcag attccagtga actgtccata tcgtacgcgt|1200|
|ataaccaact accaacgcga cggaccgcag acgtttacca caaccagga gggagcacca|1260|
|aactactacc caaacagctt tagtgggccc gaagatgtgc cacactgtgc tgctatcaag|1320|
|tttgcatcta caggagatgt agccaggtac aactctggag atgaggataa ctttagccag|1380|
|ccctctcttt tctggaagaa gaccctcaaa ccggaggagc gagaacgtct ggtgcagaac|1440|
|attgtggatc acgtgaagga tgctgctgac tttgtacagg aacgcacagt gaagaatttc|1500|
|agccaggtgg atgctgagtt tggtcgcaaa ttgactgagg gactgcgtaa gcattccaag|1560|
|aacagcagca ttgcttcagc aaatctttga gttgctgcgt ggaaacaaac tcaaggtttt|1620| tgtgggcaa attattgatt ttgaagactt caatacttaa catttcatgg gtgtttaaca    1680 ggtgctttat gtgtttggta cttttatgta c    1711

<210> SEQ ID NO 25
<211> LENGTH: 508
<212> TYPE: PRT
<213> ORGANISM: Reticulitermes flavipes
<220> FEATURE:
<221> NAME/KEY: misc_feature
<223> OTHER INFORMATION: amino acid sequence catalase "contig 230"

<400> SEQUENCE: 25

```
Met Ser Ser Pro Asp Pro Ala Ser Asp Gln Leu Val Asn Tyr Lys Lys
1               5                   10                  15

Lys Gln Thr Asp Lys Thr Lys Ile Val Thr Gly His Gly Ala Pro Val
            20                  25                  30

Asp Asn Arg Gly Ala Ser Leu Thr Val Gly Pro Arg Gly Pro Met Leu
        35                  40                  45

Leu Gln Asp Ile Thr Phe Leu Asn Glu Leu Ala His Phe Asp Arg Glu
    50                  55                  60

Arg Ile Pro Glu Arg Val Val His Ala Lys Gly Ala Gly Ala Phe Gly
65                  70                  75                  80

Tyr Phe Glu Val Thr His Asp Ile Thr Lys Tyr Cys Lys Ala Ser Val
                85                  90                  95

Phe Ser Lys Ile Gly Lys Lys Thr Pro Ile Ala Val Arg Phe Ser Thr
            100                 105                 110

Val Gly Gly Glu Ser Gly Ser Ala Asp Thr Val Arg Asp Pro Arg Gly
        115                 120                 125

Phe Ala Val Lys Phe Tyr Thr Glu Asp Gly Ile Trp Asp Leu Val Gly
    130                 135                 140

Asn Asn Thr Pro Ile Phe Phe Ile Arg Asp Pro Leu Leu Phe Pro Val
145                 150                 155                 160

Phe Ile His Thr Gln Lys Arg Asn Pro Ala Thr His Leu Lys Asp Cys
                165                 170                 175

Asp Met Phe Trp Asp Phe Leu Ser Leu Arg Pro Glu Ser Thr His Gln
            180                 185                 190

Val Met Phe Leu Phe Ser Asp Arg Gly Ile Pro Asp Gly Phe Arg His
        195                 200                 205

Met Asn Gly Tyr Gly Ser His Thr Phe Lys Ala Ile Asn Asp Lys Asn
    210                 215                 220

Glu Ala Val Tyr Val Lys Phe His Tyr Lys Thr Asn Gln Gly Ile Lys
225                 230                 235                 240

Asn Leu Leu Ala Gln Lys Ala Ser Glu Val Ala Val Ala Asp Pro Asp
                245                 250                 255

Tyr Ser Ile Arg Asp Leu Tyr Asn Ala Ile Ala Arg Gly Gln Tyr Pro
            260                 265                 270

Ser Trp Thr Leu Tyr Ile Gln Val Met Thr Phe Glu Gln Ala Glu Lys
        275                 280                 285

Phe Arg Trp Asn Pro Phe Asp Leu Thr Lys Val Trp Pro His Ala Glu
    290                 295                 300

Tyr Pro Leu Ile Pro Val Gly Lys Leu Val Leu Asp Arg Asn Pro Ala
305                 310                 315                 320

Asn Tyr Phe Ala Glu Val Glu Gln Ile Ala Phe Ser Pro Ala His Met
                325                 330                 335

Val Pro Gly Ile Glu Pro Ser Pro Asp Lys Met Leu Gln Gly Arg Leu
```

```
                340                 345                 350
Phe Ser Tyr Ser Asp Thr His Arg His Arg Leu Gly Ala Asn Tyr Leu
            355                 360                 365

Gln Ile Pro Val Asn Cys Pro Tyr Arg Thr Arg Ile Thr Asn Tyr Gln
        370                 375                 380

Arg Asp Gly Pro Gln Thr Phe Thr Asn Asn Gln Glu Gly Ala Pro Asn
385                 390                 395                 400

Tyr Tyr Pro Asn Ser Phe Ser Gly Pro Glu Asp Val Pro His Cys Ala
            405                 410                 415

Ala Ile Lys Phe Ala Ser Thr Gly Asp Val Ala Arg Tyr Asn Ser Gly
        420                 425                 430

Asp Glu Asp Asn Phe Ser Gln Pro Ser Leu Phe Trp Lys Lys Thr Leu
            435                 440                 445

Lys Pro Glu Glu Arg Glu Arg Leu Val Gln Asn Ile Val Asp His Val
        450                 455                 460

Lys Asp Ala Ala Asp Phe Val Gln Glu Arg Thr Val Lys Asn Phe Ser
465                 470                 475                 480

Gln Val Asp Ala Glu Phe Gly Arg Lys Leu Thr Glu Gly Leu Arg Lys
            485                 490                 495

His Ser Lys Asn Ser Ser Ile Ala Ser Ala Asn Leu
        500                 505

<210> SEQ ID NO 26
<211> LENGTH: 1713
<212> TYPE: DNA
<213> ORGANISM: Reticulitermes flavipes
<220> FEATURE:
<221> NAME/KEY: misc_feature
<223> OTHER INFORMATION: nucleotide sequence Esterase 1 (RfEst-1)

<400> SEQUENCE: 26
gggactcgca tgctcgctgt ggcgccgcgc gaagggcagt cggtgagtct cgtcacaact      60
gacacttgtg acgaaatctg cattgaagtt cgtgtttctt cgcttgctga aaagaagct     120 gtgttatgtt ctctaatgaa ctacagataa ccacaaatgg cggaaaccgt aacggtcact     180
gtagctcagg gtgagctgag aggaaagaaa atgacagcca gacgggaac aacgtacttc      240 agtttccagg ggattccata ctgtcagcct cctgtgggtc ctctcagatt taaggcccca     300
caaccacctg attcatggaa aggaattcgc gatgccctca cgagggctc agtcgcccca      360 cagatagatg acttcgtagc cgacgcgtat ttaggagaag aggactgttt atatctcaat     420
gtatacactc ccaaggttcc tgcacggtcc ggagatgatc tgaaagctgt gatggtgtgg     480
attcatggag gtggcttcta catgggatcg ggaaacacgc aaatcaacgg accggactat     540
ctgctagctg cagatgtcgt tgtagtcact ttaaattacc gactgggagc actaggtttc     600
ttgagtacgg aagatcccga gacctcgagt aacaacggtc tgaaggacca agtgatggct     660
ctgcgctggg ttcagcagaa tattaagcag tttggaggag atcctggtaa cgtcactatt     720
ttcggtgtca gcgctggagg ggctagtgtg cattatcaca tgttatcgcc gatgtcagaa     780
ggactcttct gccgtgccat cgcacaaagt ggctgtgcgc ttaatccttg gcattccac      840 gcagcatcga cggctcgcag aagagcgttt cggttcggag agtgctcgg ctgtaaaaca     900 gatgattcga aggaattggc tgaattcttg agtaccgtgc cggcacagca acttgttgag     960
gtggtttcaa aagccatgac agaagaggag cttgaccttg gtacagtctt cttcaggcca    1020
actgtggagg cagagaatag acaagaagaa ctctttcttc ctgcagaccc cattgatcta    1080
attacggagg ggaaattcca caaggtgcct ttcttaaccg gaatcaactc aagcgagggc    1140
```

```
cttctctgcg ttagagaggt aatggcaaaa ccagcggtac tgaagaagta cgacagtgac    1200
gtcgcccaga aaataaagag tttctacttt ggagacaagc cagtttcaca ggagacgcta    1260
tttctatacg tcgatctgag cagcgacatg tggtttgtga cggacgttca tagaacagcg    1320
aagttgcagg cagcacgatc ctccgctccc ttattcttct accagttttc atttgatgga    1380
gagcttggct tcatgaagag gattattggt gcatgtcgct ccccaggtgt atgtcatgct    1440
gacgaacttg gatatttaat tttctcgcct cacttagacg tggagctgga cgggactccg    1500
gaggagaaag tgaggtcaca gctagtcaga atgtggacca actttgctaa aacagggaac    1560
ccatcgctgt cagatgtgaa gtgtgagtca atgacagagt caaatccaag ctacctggac    1620
atcggcactg aattcactat gcagcaacac ctgatgaagg accgaatggc tttctgggac    1680
gacctaagac agtttgtcaa aatatgaaac gtt                                 1713
```

<210> SEQ ID NO 27
<211> LENGTH: 536
<212> TYPE: PRT
<213> ORGANISM: Reticulitermes flavipes
<220> FEATURE:
<221> NAME/KEY: misc_feature
<223> OTHER INFORMATION: amino acid sequence Esterase 1 (RfEst-1)

<400> SEQUENCE: 27

```
Met Ala Glu Thr Val Thr Val Thr Val Ala Gln Gly Glu Leu Arg Gly
1               5                   10                  15

Lys Lys Met Thr Ala Lys Thr Gly Thr Thr Tyr Phe Ser Phe Gln Gly
                20                  25                  30

Ile Pro Tyr Cys Gln Pro Val Gly Pro Leu Arg Phe Lys Ala Pro
            35                  40                  45

Gln Pro Pro Asp Ser Trp Lys Gly Ile Arg Asp Ala Leu Asn Glu Gly
        50                  55                  60

Ser Val Ala Pro Gln Ile Asp Asp Phe Val Ala Asp Ala Tyr Leu Gly
65                  70                  75                  80

Glu Glu Asp Cys Leu Tyr Leu Asn Val Tyr Thr Pro Lys Val Pro Ala
                85                  90                  95

Arg Ser Gly Asp Asp Leu Lys Ala Val Met Val Trp Ile His Gly Gly
            100                 105                 110

Gly Phe Tyr Met Gly Ser Gly Asn Thr Gln Ile Asn Gly Pro Asp Tyr
        115                 120                 125

Leu Leu Ala Ala Asp Val Val Val Thr Leu Asn Tyr Arg Leu Gly
    130                 135                 140

Ala Leu Gly Phe Leu Ser Thr Glu Asp Pro Glu Thr Ser Ser Asn Asn
145                 150                 155                 160

Gly Leu Lys Asp Gln Val Met Ala Leu Arg Trp Val Gln Asn Ile
                165                 170                 175

Lys Gln Phe Gly Gly Asp Pro Gly Asn Val Thr Ile Phe Gly Val Ser
            180                 185                 190

Ala Gly Gly Ala Ser Val His Tyr His Met Leu Ser Pro Met Ser Glu
        195                 200                 205

Gly Leu Phe Cys Arg Ala Ile Ala Gln Ser Gly Cys Ala Leu Asn Pro
    210                 215                 220

Trp Ala Phe His Ala Ala Ser Thr Ala Arg Arg Ala Phe Arg Phe
225                 230                 235                 240

Gly Glu Val Leu Gly Cys Lys Thr Asp Asp Ser Lys Glu Leu Ala Glu
                245                 250                 255
```

```
        Phe Leu Ser Thr Val Pro Ala Gln Gln Leu Val Glu Val Val Ser Lys
                        260                 265                 270

Ala Met Thr Glu Glu Leu Asp Leu Gly Thr Val Phe Phe Arg Pro
                    275                 280                 285

Thr Val Glu Ala Glu Asn Arg Gln Glu Glu Leu Phe Leu Pro Ala Asp
                    290                 295                 300

Pro Ile Asp Leu Ile Thr Glu Gly Lys Phe His Lys Val Pro Phe Leu
        305                 310                 315                 320

Thr Gly Ile Asn Ser Ser Glu Gly Leu Leu Cys Val Arg Glu Val Met
                        325                 330                 335

Ala Lys Pro Ala Val Leu Lys Lys Tyr Asp Ser Asp Phe Glu Leu Leu
                    340                 345                 350

Val Pro Thr Asn Leu Gly Val Glu Lys Asn Thr Pro Lys Ser Lys Glu
                    355                 360                 365

Val Ala Gln Lys Ile Lys Ser Phe Tyr Phe Gly Asp Lys Pro Val Ser
                370                 375                 380

Gln Glu Thr Leu Phe Leu Tyr Val Asp Leu Ser Ser Asp Met Trp Phe
        385                 390                 395                 400

Val Thr Asp Val His Arg Thr Ala Lys Leu Gln Ala Ala Arg Ser Ser
                        405                 410                 415

Ala Pro Leu Phe Phe Tyr Gln Phe Ser Phe Asp Gly Glu Leu Gly Phe
                    420                 425                 430

Met Lys Arg Ile Ile Gly Ala Cys Arg Phe Pro Gly Val Cys His Ala
                    435                 440                 445

Asp Glu Leu Gly Tyr Leu Ile Phe Ser Pro His Leu Asp Val Glu Leu
                450                 455                 460

Asp Gly Thr Pro Glu Glu Lys Val Arg Ser Gln Leu Val Arg Met Trp
        465                 470                 475                 480

Thr Asn Phe Ala Lys Thr Gly Asn Pro Ser Leu Ser Asp Val Lys Cys
                        485                 490                 495

Glu Ser Met Thr Glu Ser Asn Pro Ser Tyr Leu Asp Ile Gly Thr Glu
                    500                 505                 510

Phe Thr Met Gln Gln His Leu Met Lys Asp Arg Met Ala Phe Trp Asp
                    515                 520                 525

Asp Leu Arg Gln Phe Val Lys Ile
            530                 535

<210> SEQ ID NO 28
<211> LENGTH: 1454
<212> TYPE: DNA
<213> ORGANISM: Reticulitermes flavipes
<220> FEATURE:
<221> NAME/KEY: misc_feature
<223> OTHER INFORMATION: nucleotide sequence Esterase 2 (RfEst-2)

<400> SEQUENCE: 28
ggcgagaaag gcgcactggc tctatcgatg gtgtaccccg acatggacgc caggttcgag      60
gatgtagctc ccgttgcttc cgcctacgac acttcgcccc gaaagaacga atcagcaga     120 ctcataagga agttctattt cggagacaga cacatcgaca atgacacaac gacgtccgta     180
gtgaacatgt taactgacgg ctggttcttg caaggagcag accctgcagt cagccttcac     240
gctctgcgag gacctgcgcc agtttttctac tatcacttca cataccgagg ctccgtcagc    300
tttatcacgc tcttcggtaa tgcgaccgaa agtcacggtg taagtcacgg agacgacttg     360
atttaccttt tcccttccga agtatttcct ccaggcacaa agctaacagc aaaggacgaa     420
cgcgttgtgg atattatgac gacagtatgg accaacttcg ctcgcacggg gaacccgaac     480
```

```
ctcagccctg ataacgccgt gcagtggcgg ccagtgtctt catcacacga taaagagtac      540
gtccaaatcg actccgaagg cctgaccccg aaaaaagggc tgctagaaga aagagccaac      600
ttctggaact ctttgccttt gaagagttct cactcaggtt ctgcaacgag cgaactctga      660
aagaaatgtg catataataa tggaaggttt taaatacttc gtaagaaata cagtcgaact      720
cggttataac gtcatgaaag ggactgaata ttttgtgtcg ttataaacga gtgttgttat      780
aaccgaggag tataatgtta tggctaagag tgaggaatta attggtaccg cagaacatct      840
gatggtatag acgaggtatc gtataaaccg atgtcgttat aagcgggttc aactgtattt      900
tgaattatag atttgtaata agtatccatc cttccttggc tcatggtcat ctaagaacct      960
cacctccttt atcactgcaa ttcttctcat tatttgccat cggccttccc ttggatcgcc     1020
gtcagttcct gtacacgagt ccttacatct cgcagtaatt accactagg ccatcccaac     1080 gtacattcag gatacaaata aagtggctct gtctgctgat tgtaactgcc ttttaccgtc     1140
caatacgccg gttccaatcc atcctctaca aatgacgcct aacctaacac aatgaggcgc     1200
tgcggttaaa acaaaagaaa ttgcatttaa aaatcaacaa agaaattcta cacccacga     1260 accaactaca cgaaactgag tcttttcttag agaagcggag gtagtttttt acgagtaggg     1320
gagagggggg atagttggca cacttttcac tttagaagtt ttcacatttt ccctggtact     1380
tgttaagttg aatgtaacgg cacgtatggg tagcaacact tcttgggcta caaatctgac     1440
ctacacaaat ttga                                                       1454
```

<210> SEQ ID NO 29
<211> LENGTH: 199
<212> TYPE: PRT
<213> ORGANISM: Reticulitermes flavipes
<220> FEATURE:
<221> NAME/KEY: misc_feature
<223> OTHER INFORMATION: amino acid sequence Esterase 2 (RfEst-2)

<400> SEQUENCE: 29

```
Asp Val Ala Pro Val Ala Ser Ala Tyr Asp Thr Ser Pro Arg Lys Asn
1               5                   10                  15

Glu Ile Ser Arg Leu Ile Arg Lys Phe Tyr Phe Gly Asp Arg His Ile
            20                  25                  30

Asp Asn Asp Thr Thr Thr Ser Val Val Asn Met Leu Thr Asp Gly Trp
        35                  40                  45

Phe Leu Gln Gly Ala Asp Pro Ala Val Ser Leu His Ala Leu Arg Gly
    50                  55                  60

Pro Ala Pro Val Phe Tyr Tyr His Phe Thr Tyr Arg Gly Ser Val Ser
65                  70                  75                  80

Phe Ile Thr Leu Phe Gly Asn Ala Thr Glu Ser His Gly Val Ser His
                85                  90                  95

Gly Asp Asp Leu Ile Tyr Leu Phe Pro Ser Glu Ser Ile Ser Pro Gly
            100                 105                 110

Thr Lys Leu Thr Ala Lys Asp Glu Arg Val Val Asp Ile Met Thr Thr
        115                 120                 125

Val Trp Thr Asn Phe Ala Arg Thr Gly Asn Pro Asn Leu Ser Pro Asp
    130                 135                 140

Asn Ala Val Gln Trp Arg Pro Val Ser Ser His Asp Lys Glu Tyr
145                 150                 155                 160

Val Gln Ile Asp Ser Glu Gly Leu Thr Pro Lys Lys Gly Leu Leu Glu
                165                 170                 175

Glu Arg Ala Asn Phe Trp Asn Ser Leu Pro Leu Lys Ser Ser His Ser
```

Gly Ser Ala Thr Ser Glu Leu
        195

<210> SEQ ID NO 30
<211> LENGTH: 1204
<212> TYPE: DNA
<213> ORGANISM: Reticulitermes flavipes
<220> FEATURE:
<221> NAME/KEY: misc_feature
<223> OTHER INFORMATION: nucleotide sequence Esterase 3 (RfEst-3)

<400> SEQUENCE: 30

```
gggggcccca cagaaaactc cgaggaactt gtcgcatgtt tgagaacacg ggatgtcaaa      60
accattctag tcaaccagcc cagcgactgt tccgcaccac ctggagactt ttcattcttt     120
ttgtgcctgt acgacatagt ctggagacca gtgagtgagg tgaagacggc cgccaaccca     180
gagcccttcc tgacagcaca tcctaaggac atcatcaggt ccggggactt caaccgcgtg     240
ccttttgtac tgggcaccaa ttctgaggag ggatcattgt tcctattacc cttcatcggc     300
accgataaag gcatagaata tttcaatagc ttcctcgaag atgtcggtag actttctttc     360
ttcttgaacg agagcgtgcc ggaagatctc gtctccgaca cgtgacataa tgtgagcgac     420
ttctacttgg gcagcgaccg cgtcgttacc acaaccaatg tgcacaacat tattaacgca     480
ggaacggacc ggttcatgca gcataatata cagaagtctg tggaactaca cctccagtca     540
ggccacgaca cagtatatct ctacaacctg ggctaccgtg gtaaatacag cttactgcca     600
aaggcacggt atgggaacac ccggtatgat ctcggcgttg cccatgtaga tgaattggaa     660
tttatcttat cgtccgcttt cacggccgac agatgggagc ctggacatcc tgatctagag     720
acggttgaag acttggtcac cttgtggaca aattttgcta cacacggaaa cccgacgcct     780
gaagcagaaa ctccaactcc gcaaggcgtc gtgtggccca cggccggagc caacaaagat     840
gccataacct actacgtttt cgatcattca ccaccccccag ccgaacccat ttatggtgtc     900
aggccactac gtatcagtgt ggttcctgac aaattcaagg atcgcatgga cctctgggat     960
tcactgcccc ttaaggaaaa ccaataacag cagcatgaga ggtttgcttc agtgggtctg    1020
ccaaacaggt ttaaataaag cctgttctac acatcaatat aatctgcttc aaggaataac    1080
ttgcatccag aaaatactga atttgagcaa ttgttaatat aatagatatg ttgtggcacc    1140
gtttgcgtta caatgcagaa ttaaatgttt tcttttcttc cataaaaaaa aaaaaaaaa     1200
aaaa                                                                 1204
```

<210> SEQ ID NO 31
<211> LENGTH: 163
<212> TYPE: PRT
<213> ORGANISM: Reticulitermes flavipes
<220> FEATURE:
<221> NAME/KEY: misc_feature
<223> OTHER INFORMATION: amino acid sequence Esterase 3 (RfEst-3)

<400> SEQUENCE: 31

Met Gln His Asn Ile Gln Lys Ser Val Glu Leu His Leu Gln Ser Gly
1               5                   10                  15

His Asp Thr Val Tyr Leu Tyr Asn Leu Gly Tyr Arg Gly Lys Tyr Ser
            20                  25                  30

Leu Leu Pro Lys Ala Arg Tyr Gly Asn Thr Arg Tyr Asp Leu Gly Val
        35                  40                  45

Ala His Val Asp Glu Leu Glu Phe Ile Leu Ser Ser Ala Phe Thr Ala
    50                  55                  60

Asp Arg Trp Glu Pro Gly His Pro Asp Leu Glu Thr Val Glu Asp Leu
65                  70                  75                  80

Val Thr Leu Trp Thr Asn Phe Ala Thr His Gly Asn Pro Thr Pro Glu
            85                  90                  95

Ala Glu Thr Pro Thr Pro Gln Gly Val Val Trp Pro Thr Ala Gly Ala
                100                 105                 110

Asn Lys Asp Ala Ile Thr Tyr Tyr Val Phe Asp His Ser Pro Pro
        115                 120                 125

Ala Glu Pro Ile Tyr Gly Val Arg Pro Leu Arg Ile Ser Val Val Pro
        130                 135                 140

Asp Lys Phe Lys Asp Arg Met Asp Leu Trp Asp Ser Leu Pro Leu Lys
145                 150                 155                 160

Glu Asn Gln

<210> SEQ ID NO 32
<211> LENGTH: 830
<212> TYPE: DNA
<213> ORGANISM: Reticulitermes flavipes
<220> FEATURE:
<221> NAME/KEY: misc_feature
<223> OTHER INFORMATION: nucleotide sequence Esterase 4 (RfEst-4)

<400> SEQUENCE: 32
gggggggaga ggtaaagcaa cgaaactggc acaagaattg ggttgtaaca cacaaacttc      60
acgcgagctg gtagactgcc tcaggcatcg gccagcaaaa attattgttc aaaaagtagc     120
aatctttgaa attggattgc aagagaagac attttgaatg aaatacagaa cagatttttct    180 gagattgcac ctttcatatt agactacaac tacactgtgt cagagaagca gaagctggct     240
gttgctcaga gcattcatca gttttatctt cagggtaaaa caatatcaac agacaccaaa     300
tgtaacttta ttgagatggc tggtgaccgc cattttgttg tggaaatgga acgagcagcc     360
agaattcaag ctgctgtcaa ctcagcacct gtatatgttt atcagtttgg ctacagaggg     420
aaacacagtt tatctgaaga aatatcagga acaaacattg atttcggtgc tgcccatgca     480
gatgatgcag cttttgtact acaaattcac tatcataaca ctgaagagac acagcaagac     540
aaggacatgt ccaaagtact tgtggatatt tggagtagtt tcagcagaaa tggaaatccc     600
aaccctgatg caccgacttt cacctgggaa cctgtgacac ccaacggcgc ggagcttgca     660
tatttgtata tagctaacag cagccacttt gaaatgagat ccagccttga cttgggacac     720
agagaattct gggattcact acccattaat gaacctcaga ttaatgtaaa tgttcgcaac     780
ataaggcaat ctactcgtga agaactatag aacttacgaa ccaagtagtc                830

<210> SEQ ID NO 33
<211> LENGTH: 164
<212> TYPE: PRT
<213> ORGANISM: Reticulitermes flavipes
<220> FEATURE:
<221> NAME/KEY: misc_feature
<223> OTHER INFORMATION: amino acid sequence Esterase 4 (RfEst-4)

<400> SEQUENCE: 33

Met Ala Gly Asp Arg His Phe Val Val Glu Met Glu Arg Ala Ala Arg
1               5                   10                  15

Ile Gln Ala Ala Val Asn Ser Ala Pro Val Tyr Val Tyr Gln Phe Gly
            20                  25                  30

Tyr Arg Gly Lys His Ser Leu Ser Glu Glu Ile Ser Gly Thr Asn Ile
        35                  40                  45

-continued

```
Asp Phe Gly Ala Ala His Ala Asp Asp Ala Phe Val Leu Gln Ile
 50                  55                  60
His Tyr His Asn Thr Glu Thr Gln Gln Asp Lys Asp Met Ser Lys
 65                  70                  75                  80
Val Leu Val Asp Ile Trp Ser Ser Phe Ser Arg Asn Gly Asn Pro Asn
                 85                  90                  95
Pro Asp Ala Pro Thr Phe Thr Trp Glu Pro Val Thr Pro Asn Gly Ala
                100                 105                 110
Glu Leu Ala Tyr Leu Tyr Ile Ala Asn Ser Ser His Phe Glu Met Arg
                115                 120                 125
Ser Ser Leu Asp Leu Gly His Arg Glu Phe Trp Asp Ser Leu Pro Ile
                130                 135                 140
Asn Glu Pro Gln Ile Asn Val Asn Val Arg Asn Ile Arg Gln Ser Thr
145                 150                 155                 160
Arg Glu Glu Leu

<210> SEQ ID NO 34
<211> LENGTH: 22
<212> TYPE: DNA
<213> ORGANISM: Artificial sequence
<220> FEATURE:
<223> OTHER INFORMATION: RfEsT1 L CONTIG 515L-SET 4 Primer

<400> SEQUENCE: 34
atgacagaag aggagcttga cc                                              22

<210> SEQ ID NO 35
<211> LENGTH: 22
<212> TYPE: DNA
<213> ORGANISM: Artificial sequence
<220> FEATURE:
<223> OTHER INFORMATION: RfEst1 Reverse CONTIG 515R-SET4 Primer

<400> SEQUENCE: 35
caggagttca aagtcactgt cg                                              22

<210> SEQ ID NO 36
<211> LENGTH: 22
<212> TYPE: DNA
<213> ORGANISM: Artificial sequence
<220> FEATURE:
<223> OTHER INFORMATION: RfEst2 L CONTIG 493-1R Primer

<400> SEQUENCE: 36
ggttaggcgt catttgtaga gg                                              22

<210> SEQ ID NO 37
<211> LENGTH: 22
<212> TYPE: DNA
<213> ORGANISM: Artificial sequence
<220> FEATURE:
<223> OTHER INFORMATION: RfEsT2 Reverse CONTIG493-1L Primer

<400> SEQUENCE: 37
ggctcatggt catctaagaa cc                                              22

<210> SEQ ID NO 38
<211> LENGTH: 22
<212> TYPE: DNA
<213> ORGANISM: Artificial sequence
<220> FEATURE:
<223> OTHER INFORMATION: RfEsT3 L CONTIG 275L-SET5 Primer

<400> SEQUENCE: 38
```
agagacggtt gaaagacttgg tc                                            22

<210> SEQ ID NO 39
<211> LENGTH: 22
<212> TYPE: DNA
<213> ORGANISM: Artificial sequence
<220> FEATURE:
<223> OTHER INFORMATION: RfEsT3 Reverse CONTIG 275R-SET5 Primer

<400> SEQUENCE: 39
actgatacgt agtggcctga ca                                             22

<210> SEQ ID NO 40
<211> LENGTH: 20
<212> TYPE: DNA
<213> ORGANISM: Artificial sequence
<220> FEATURE:
<223> OTHER INFORMATION: RfEsT4 L TG_15_C3 1L Primer

<400> SEQUENCE: 40
gccagaattc aagctgctgt                                                20

<210> SEQ ID NO 41
<211> LENGTH: 22
<212> TYPE: DNA
<213> ORGANISM: Artificial sequence
<220> FEATURE:
<223> OTHER INFORMATION: RfEsT4 R TG_15_C3 1R Primer

<400> SEQUENCE: 41
tgtccttgtc ttgctgtgtc tc                                             22

<210> SEQ ID NO 42
<211> LENGTH: 20
<212> TYPE: DNA
<213> ORGANISM: Artificial sequence
<220> FEATURE:
<223> OTHER INFORMATION: Beta-Actin L Forward Primer

<400> SEQUENCE: 42
agagggaaat cgtgcgtgac                                                20

<210> SEQ ID NO 43
<211> LENGTH: 21
<212> TYPE: DNA
<213> ORGANISM: Artificial sequence
<220> FEATURE:
<223> OTHER INFORMATION: Beta-Actin Reverse Primer

<400> SEQUENCE: 43
caatagtgat gacctggccg t                                              21

<210> SEQ ID NO 44
<211> LENGTH: 11
<212> TYPE: PRT
<213> ORGANISM: Artificial sequence
<220> FEATURE:
<223> OTHER INFORMATION: RfEst1 leader peptide

<400> SEQUENCE: 44

Met Ala Glu Thr Val Thr Val Thr Val Ala Gln
1               5                   10

<210> SEQ ID NO 45
<211> LENGTH: 89
<212> TYPE: DNA

<213> ORGANISM: Artificial sequence
<220> FEATURE:
<223> OTHER INFORMATION: Cell-1 BEV Expression Replicon Forward Primer

<400> SEQUENCE: 45

```
ctagtctaga ctagatgaag atactccttg ctattgcatt aatgttgtca acagtaatgt    60
gggtgtcaac agctgcttac gactataag                                      89
```

<210> SEQ ID NO 46
<211> LENGTH: 56
<212> TYPE: DNA
<213> ORGANISM: Artificial sequence
<220> FEATURE:
<223> OTHER INFORMATION: Cell-1 BEV Expression Replicon Reverse Primer

<400> SEQUENCE: 46

```
tttccttttg cggccgctta gtgatgatgg tgatgatgca cgccagcctt gaggag         56
```

<210> SEQ ID NO 47
<211> LENGTH: 496
<212> TYPE: DNA
<213> ORGANISM: Reticulitermes flavipes
<220> FEATURE:
<221> NAME/KEY: misc_feature
<223> OTHER INFORMATION: nucleotide sequence Beta-glucosidase
      (RfBgluc-1)

<400> SEQUENCE: 47

```
ggggcatatc cttgaaaagt gagtggtttg aacccgagac aagttcaaca gccgacaagg    60
aagcagctga gaaagctatc cagtatcaac ttggtctctt tgcaaatcca atatatagct   120
ctgaaggtga ctatccacag atcatacgtg aggagttgga aaaacttagc attgctcagg   180
gatacccaaa atcacgactg aggaaattca ctccagaaga agtcaccaat attaaaggga   240
cctatgattt ccttgggttg aattactaca ctgctcgatt agtgagagct cctcaaccaa   300
cgatagactt attgaatgct ccagacaata atgtaatcct cgttactgat cccaagtggc   360
ctacatcagc cagtacatac ctaaaggtgg tgccttgggg cttccgtaaa ttgctaaact   420
ggatcaagag agcttacatc aatactccgg tgcttgttac agggaatgga ttcttctgac   480
agaggagaaa actgaa                                                   496
```

<210> SEQ ID NO 48
<211> LENGTH: 17
<212> TYPE: PRT
<213> ORGANISM: Artificial sequence
<220> FEATURE:
<223> OTHER INFORMATION: RfBGluc-1 leader peptide

<400> SEQUENCE: 48

```
Met Arg Leu Gln Thr Val Cys Phe Val Ile Phe Val Thr Ala Val Phe
1               5                   10                  15

Gly
```

<210> SEQ ID NO 49
<211> LENGTH: 159
<212> TYPE: PRT
<213> ORGANISM: Reticulitermes flavipes
<220> FEATURE:
<221> NAME/KEY: misc_feature
<223> OTHER INFORMATION: amino acid sequence Beta-Glucosidase RfBGluc-2

<400> SEQUENCE: 49

```
Gly Ile Ser Leu Lys Ser Glu Trp Glu Glu Pro Glu Thr Ser Ser Thr
1               5                   10                  15
```

```
Ala Asp Lys Glu Ala Ala Glu Lys Ala Ile Gln Tyr Gln Leu Gly Leu
         20                  25                  30

Phe Ala Asn Pro Ile Tyr Ser Ser Glu Glu Gly Asp Tyr Pro Gln Ile
     35                  40                  45

Ile Arg Glu Glu Leu Glu Lys Leu Ser Ile Ala Gln Gly Tyr Pro Lys
 50                  55                  60

Ser Arg Leu Arg Lys Phe Thr Pro Glu Glu Val Thr Asn Ile Lys Gly
 65                  70                  75                  80

Thr Tyr Asp Phe Leu Gly Leu Asn Tyr Tyr Thr Ala Arg Leu Val Arg
                 85                  90                  95

Ala Pro Gln Pro Thr Ile Asp Leu Leu Asn Ala Pro Asp Asn Asn Val
                100                 105                 110

Ile Leu Val Thr Asp Pro Lys Trp Pro Thr Ser Ala Ser Thr Tyr Leu
                115                 120                 125

Lys Val Val Pro Trp Gly Phe Arg Lys Leu Leu Asn Trp Ile Lys Arg
                130                 135                 140

Ala Tyr Ile Asn Thr Pro Val Leu Val Thr Gly Asn Gly Phe Phe
145                 150                 155
```

<210> SEQ ID NO 50
<211> LENGTH: 21
<212> TYPE: DNA
<213> ORGANISM: Artificial sequence
<220> FEATURE:
<223> OTHER INFORMATION: RfBGluc-1 "21C3 L" Primer

<400> SEQUENCE: 50
tgcttcttca tggctcagag t                                      21

<210> SEQ ID NO 51
<211> LENGTH: 21
<212> TYPE: DNA
<213> ORGANISM: Artificial sequence
<220> FEATURE:
<223> OTHER INFORMATION: RfBGluc-1 "21C3 R" Primer

<400> SEQUENCE: 51
tggtctccag gttgtgtatc c                                      21

<210> SEQ ID NO 52
<211> LENGTH: 21
<212> TYPE: DNA
<213> ORGANISM: Artificial sequence
<220> FEATURE:
<223> OTHER INFORMATION: RfBGluc-2 "309K21 L" Primer

<400> SEQUENCE: 52
gagagctcct caaccaacga t                                      21

<210> SEQ ID NO 53
<211> LENGTH: 21
<212> TYPE: DNA
<213> ORGANISM: Artificial sequence
<220> FEATURE:
<223> OTHER INFORMATION: "309K21 R" Primer

<400> SEQUENCE: 53
cctgtaacaa gcaccggagt a                                      21

<210> SEQ ID NO 54
<211> LENGTH: 23
<212> TYPE: DNA

```
<213> ORGANISM: Artificial sequence
<220> FEATURE:
<223> OTHER INFORMATION: NADH-DH Forward Primer

<400> SEQUENCE: 54 gctggggtg ttattcattc cta                                       23

<210> SEQ ID NO 55
<211> LENGTH: 21
<212> TYPE: DNA
<213> ORGANISM: Artificial sequence
<220> FEATURE:
<223> OTHER INFORMATION: NADH-DH Reverse Primer

<400> SEQUENCE: 55
ggcataccac aaagagcaaa a                                        21

<210> SEQ ID NO 56
<211> LENGTH: 27
<212> TYPE: DNA
<213> ORGANISM: Artificial sequence
<220> FEATURE:
<223> OTHER INFORMATION: RfBGluc-1 ORF Amplicon Forward Primer

<400> SEQUENCE: 56
gtcgacatga ggttacagac ggtttgc                                  27

<210> SEQ ID NO 57
<211> LENGTH: 47
<212> TYPE: DNA
<213> ORGANISM: Artificial sequence
<220> FEATURE:
<223> OTHER INFORMATION: RfBGluc-1 ORF Amplicon Reverse Primer

<400> SEQUENCE: 57
ctgcagttag tgatgatggt gatgatggtc taggaagcgt tctggaa            47

<210> SEQ ID NO 58
<211> LENGTH: 26
<212> TYPE: DNA
<213> ORGANISM: Artificial sequence
<220> FEATURE:
<223> OTHER INFORMATION: Laccase5-R_336" Reverse Primer

<400> SEQUENCE: 58
gcttgctggt tgcgggaatc cgtcgt                                   26

<210> SEQ ID NO 59
<211> LENGTH: 25
<212> TYPE: DNA
<213> ORGANISM: Artificial sequence
<220> FEATURE:
<223> OTHER INFORMATION: Laccase3-F_584" Forward Primer

<400> SEQUENCE: 59
cgcccccatc tccgctcctc tcaca                                    25

<210> SEQ ID NO 60
<211> LENGTH: 24
<212> TYPE: DNA
<213> ORGANISM: Artificial sequence
<220> FEATURE:
<223> OTHER INFORMATION: Alternative Laccase5-R_336" Reverse Primer

<400> SEQUENCE: 60
acttcagttg gtgttcacgg gagg                                     24
```

```
<210> SEQ ID NO 61
<211> LENGTH: 16
<212> TYPE: PRT
<213> ORGANISM: Artificial sequence
<220> FEATURE:
<223> OTHER INFORMATION: RfLacA/B conserved leader peptide

<400> SEQUENCE: 61

Met Leu Pro Cys Val Leu Leu Ala Cys Ala Ile Gly Val Ala Ser Ala
1               5                   10                  15

<210> SEQ ID NO 62
<211> LENGTH: 28
<212> TYPE: DNA
<213> ORGANISM: Artificial sequence
<220> FEATURE:
<223> OTHER INFORMATION: RfLacA/B BEV Expression Amplicon Forward Primer

<400> SEQUENCE: 62
tctagaatgt tgccttgcgt cctgcttg                                      28

<210> SEQ ID NO 63
<211> LENGTH: 54
<212> TYPE: DNA
<213> ORGANISM: Artificial sequence
<220> FEATURE:
<223> OTHER INFORMATION: RfLacA/B BEV Expression Amplicon Reverse Primer

<400> SEQUENCE: 63
cggccgttag tgatgatggt gatgatgacc tccgttggtg ttcacgggag gtgt         54

<210> SEQ ID NO 64
<211> LENGTH: 20
<212> TYPE: DNA
<213> ORGANISM: Artificial sequence
<220> FEATURE:
<223> OTHER INFORMATION: RfLacc-EXP-F1_52663 Primer

<400> SEQUENCE: 64
aatcaaactg ggtgctttgg                                               20

<210> SEQ ID NO 65
<211> LENGTH: 20
<212> TYPE: DNA
<213> ORGANISM: Artificial sequence
<220> FEATURE:
<223> OTHER INFORMATION: RfLacc-EXP-R1_52664 Primer

<400> SEQUENCE: 65
aacttgatga tcgcgtagcc                                               20
```